(12) United States Patent
Kilaas et al.

(10) Patent No.: US 10,364,217 B2
(45) Date of Patent: Jul. 30, 2019

(54) CHEMICAL COMPOUNDS

(71) Applicant: ResMan AS, Ranheim (NO)

(72) Inventors: Lars Kilaas, Trondheim (NO); Erland Nordgard, Trondheim (NO); Anne Dalager Dyrli, Trondheim (NO)

(73) Assignee: ResMan AS, Ranheim (NO)

( * ) Notice: Subject to any disclaimer, the term of this patent is extended or adjusted under 35 U.S.C. 154(b) by 223 days.

(21) Appl. No.: 15/023,424

(22) PCT Filed: Sep. 29, 2014

(86) PCT No.: PCT/NO2014/050179
§ 371 (c)(1),
(2) Date: Mar. 21, 2016

(87) PCT Pub. No.: WO2015/047105
PCT Pub. Date: Apr. 2, 2015

(65) Prior Publication Data
US 2016/0214930 A1    Jul. 28, 2016

(30) Foreign Application Priority Data

Sep. 30, 2013    (NO) .................................. 20131305

(51) Int. Cl.
| | |
|---|---|
| *C09K 8/68* | (2006.01) |
| *C07C 309/10* | (2006.01) |
| *E21B 47/10* | (2012.01) |
| *C07C 69/76* | (2006.01) |
| *C07C 43/205* | (2006.01) |

(Continued)

(52) U.S. Cl.
CPC .......... *C07C 309/10* (2013.01); *C07C 43/202* (2013.01); *C07C 43/2055* (2013.01); *C07C 43/225* (2013.01); *C07C 55/02* (2013.01); *C07C 63/307* (2013.01); *C07C 69/40* (2013.01); *C07C 69/42* (2013.01); *C07C 69/44* (2013.01);

(Continued)

(58) Field of Classification Search
None
See application file for complete search history.

(56) References Cited

U.S. PATENT DOCUMENTS

| | | | |
|---|---|---|---|
| 6,337,380 B1 * | 1/2002 | Sasaki | .............. C08F 212/14 430/522 |
| 2006/0252927 A1 * | 11/2006 | Yamamoto | .......... C09B 47/0678 540/129 |

(Continued)

FOREIGN PATENT DOCUMENTS

NO    333424    1/2010

OTHER PUBLICATIONS

Tugcu N. et al., Synthesis and characterization of high affinity, low molecular-mass displacers for anion exchange chromatography, Ind. Eng. Chem Res. 2002, 41 6482-6492. (Year: 2002).*

(Continued)

*Primary Examiner* — John J Figueroa
(74) *Attorney, Agent, or Firm* — Wenderoth, Lind & Ponack, L.L.P.

(57) ABSTRACT

The present invention relates to novel compounds of poly-functionalized polyethylene and polypropylene glycols, their synthesis and their use, in particular as tracers in applications related to oil and gas production, and especially as specific markers of various target fluids.

18 Claims, 25 Drawing Sheets

Figure 1:
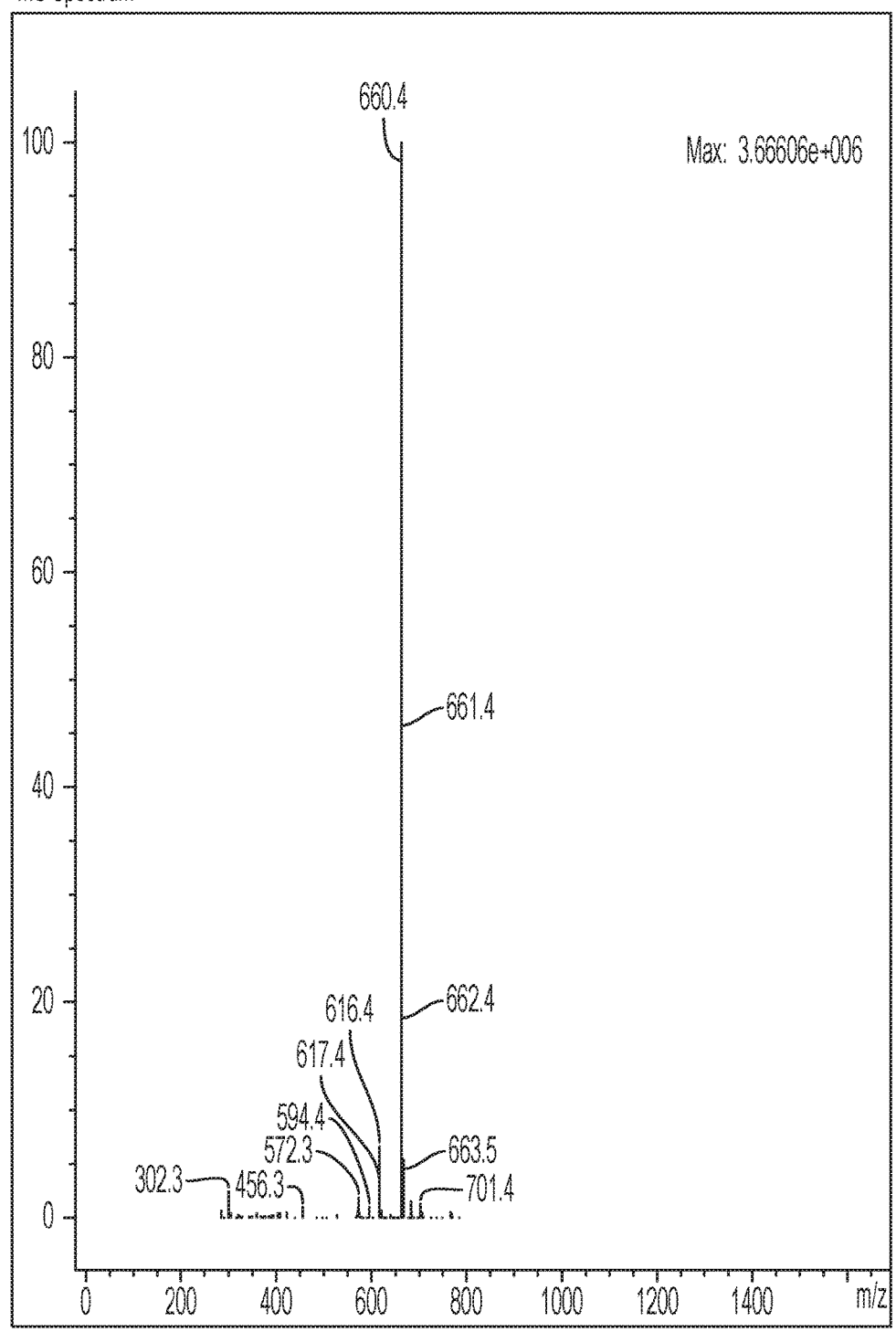

(51) Int. Cl.
  C07C 69/42 (2006.01)
  C07C 55/02 (2006.01)
  C07C 63/307 (2006.01)
  C07C 43/20 (2006.01)
  G01N 33/28 (2006.01)
  C07C 69/40 (2006.01)
  C07C 69/44 (2006.01)
  C07C 43/225 (2006.01)

(52) U.S. Cl.
  CPC ............ C07C 69/76 (2013.01); C09K 8/68 (2013.01); E21B 47/1015 (2013.01); G01N 33/2882 (2013.01)

(56) References Cited

U.S. PATENT DOCUMENTS

2009/0111049 A1* 4/2009 Oya .................. B41C 1/1008
  430/271.1
2010/0006750 A1 1/2010 Zahlsen et al.

OTHER PUBLICATIONS

Sci Finder Search dated Apr. 19, 2016 including journal article references dating 2008-2015. (Year: 2016).*
Torsten, Hegmartn et al., "Liquid crystalline paracyclophanes and ansa compounds—series of polyether macrocycles incorporating diacetylene, phenyl, biphenyl, p-terphenyl and 2,5-diphenyl-1,3,4,-thiadiazole rigid cores", Journal of Materials Chemistry, vol. 15, No. 10, Jan. 1, 2005, p. 1025, XP055165434.
International Search Report dated Feb. 6, 2015 in International Application No. PCT/NO2014/050179.
International Preliminary Report on Patentability dated Dec. 22, 2015 in International Application No. PCT/NO2014/050179.
Written Opinion of the International Preliminary Examining Authority dated Dec. 3, 2015 in International Application No. PCT/NO2014/050179.
Norwegian Search Report dated Feb. 18, 2014 in Norwegian patent application No. 20131305 (with English translation).
Yahui Feng et al., "Efficient Syntheses and Complexation Studies of Diacetylene-Containing Macrocyclic Polyethers", European Journal of Organic Chemistry, vol. 2011, No. 3, Nov. 26, 2010, pp. 562-568, XP055165340.
Guixia, Hu et al., "Water-Soluble Chiral Polyisocyanides Showing Thermoresponsive Behavior", Macromolecules, vol. 46, No. 3, Feb. 12, 2013, p. 1124-1132, XP055165361.
Seiji Shinkai et al., "Redox-Switched Crown Ethers, Cyclic-Acyclic Interconversion Coupled with Redox between Dithiol and Disulfide", J. Org. Chem., Jan. 1, 1984, pp. 3440-3442, XP055165353.
Von Dominique Armspach et al., "Selbstorganisation von Catenanen mit Cyclodextrineinheiten", Angewandte Chemie (International Ed. in English), vol. 105, No. 6, Jun. 1, 1993, pp. 944-948, XP055165433.
Von Pier Lucio Anelli et al., "Selbstassoziierender [2]-Pseudorotaxane", Angewandte Chemie (International Ed. in English), vol. 103, No. 8, Aug. 1, 1991, pp. 1052-1054, XP055165430.
Torsten, Hegmann et al., "Liquid crystalline paracyclophanes and ansa compounds—series of polyether macrocycles incorporating diacetylene, phenyl, biphenyl, p-terphenyl and 2,5-diphenyl-1,3,4,-thiadiazole rigid cores", Journal of Materials Chemistry, vol. 15, No. 10, Jan. 1, 2005, p. 1025, XP055165434.
Ahmed Saleh A et al., "Synthesis of Oligo (ethylene glycol) toward 44-mer", The Journal of Organic Chemistry, American Chemical Society, US, vol. 71, Jan. 1, 2006, pp. 9884-9886, XP002664232.
Perec, V. et al., "Self-Assembly of Janus Dendrimers into Uniform Dendrimersomes and Other Complex Architectures", Science, 2010, vol. 328, pp. 1009-1014.
Document which shows the connection between reference Perec, V. et al.

* cited by examiner

CHEMICAL COMPOUNDS

The present invention relates to novel compounds of polyfunctionalized polyethylene and polypropylene glycols, their synthesis and their use, in particular as tracers in applications related to oil and gas production, and especially as specific markers of various target fluids.

U.S. Pat. No. 6,545,769 B2 (WO 0181914) discloses a method for monitoring hydrocarbon and water production from different production zones/sections in a hydrocarbon reservoir by placing specific tracers in different zones/section of a reservoir. The tracers are detected downstream as they are produced from the well as indication of specific events in the reservoir. The tracers may be perfluorinated hydrocarbons, oligonucleotides with special functional groups, fluorescent, phosphorescent, magnetic particles or fluids, colored particles, DNA or microorganisms.

US 2010/0006750 A1 discloses a tracer system comprising a tracer compound for a fluid system containing one or more poyether alcohol compounds. The one or more polyether alcohol compound is truly monodisperse (have unique molecular weights) and comprises one or more functional groups (which will modify its solubility properties as required for the purpose). These compounds are linear polyether alcohols with different end groups attached to the PEG or PPG main chain. In order to be used as tracers, and low detection limits, the main chain of PEG or PPG should constitute of at least 4 glycol units and preferable 6 glycol units.

There is a further need for compounds as tracers in many areas. Examples are tracing of downstream effluents from oil and gas reservoirs, industrial and other discharges, leak detection, pollution studies, natural waterflow analysis, sewer and stormwater drainage analysis, in vivo tracing of body fluids during medication and diagnostic methods, tracing of food, animal feed and industrial products to trace their origin and others.

The compounds of the present application have not been described in nor indicated as tracers or otherwise synthesized in the prior art.

The present invention has surprisingly revealed the possibility to use truly monosized PEG and PPG derivatives of chain lengths down to two, which is cheap and commercial available, coupled to a core unit and in that way enhance the response, enhance separation and signal/detection, in e.g. LC/MS analytical setups, and hence give rise to monitor these compounds in very low concentrations e.g. ppb-ppq-levels. Even better (lower) detection limits may be obtained when compounds described in the present invention are analyzed when positive or negative ions are formed with the compounds through adducts and the adducts analyzed using e.g. LC/MS techniques. In this way two separate di-ethylene glycol derivatives attached to a core unit may exhibit the same low detection limit as for derivatives described in US 2010/0006750 A1, and in this way a totally new class of molecules can be used as chemical tracers.

The subject matter of the present invention are PEG or PPG based molecules constitute of a core unit with 2-4 monosized PEG or PPG based derivatives attached to the this core unit. The new compounds described in the present invention could either be linear, "V" or "star-shaped" and have various conformations in space. These compounds can further, in a post modification step or during the initial synthesis, be functionalized to modify its physical, chemical and analytical properties like for instance its solubility, surface adherence properties, bioavailability and detectability. In this way the tracers can be tailored for a number of different applications while maintaining their basic general structural backbone.

The possibility for use of molecules with a relative large molecular weight, combined with use of variable core units having various possible interchangeable substituents, implies that a large number of possible unique tracers with distinct molecular weights and properties can be synthesized and used for different applications. Depending on their specific structure, the molecules can be made quite stable and able to survive harsh and variable conditions like high temperature, high pressure, and large variations in pH and brine environments often found in oil and gas reservoirs. The good stability of tracers are also very important in order not to degrade due to different completion fluids and chemicals added during the production phase. The good stability of the compounds also means that they can be detected for a long time. Functionalization of the described derivatives expands the possibility of detection using available analytical tools like mass spectrometry (coupled with GC/HPLC etc), colorimetric, fluorescence radiation etc.

Use of short PEG units or PPG units or a combination of these derivatives connected to proper defined core units, makes it possible to generate a large number of unique molecules e.g. as tracer, having the same high analytical LC/MS response as long PEG units or PPG units, and hence extending the total number of suitable tracer candidates.

It is also surprisingly observed that the analytical response may be additionally increased for aromatic core units with substituents in ortho position to each other. By placing the substituents in -ortho, -meta, -para or having other special geometry, the degree of mono, di or multivalent ions generated in the MS is altered and hence there is possible to tailor the best response for a given molecule to achieve specific identification and low limit of detection.

The invention also makes use of the similarity of reaction steps for the different molecules, enabling an easy optimization of the reaction pathways for generating a large number of unique molecules, and the compounds may be produced in high yields and high purity.

By introducing various combinations of parts of the molecule and or introduction of bulky segments (chemical groups/moieties) the leak-out can be controlled to obtain the optimal release for various set of conditions.

This new design for generating oil and water soluble compounds also minimize the possibility to generate "homolog" molecules that differs in molecular weight by a factor of 44 (one PEG unit) or 58 (one PPG unit), and were the "homologs" are introduced either by impurities in the monosized PEG and PPG derivatives used in the synthesis, or by degradation of reagents and intermediates during synthesis. The possibility of coupling two identical homologs, present as impurities in reagents, onto the same core compound are very minor and results in very low, often neglectable concentrations (less than 1%), hence very low concentration of each of the other unique compounds are obtained as impurities in the synthesis.

The prior art discloses use of linear monosized polyethers generating a linear chain backbone with different end groups. When synthesizing these types of compounds, the presence of "homolog" reagents will give rice to the corresponding "homologue" final product in a concentration equal to the impurities. The use of core units, substituents and reaction pathways as described in the present invention, eliminates this disadvantage and hence are more versatile for generating large number of unique molecules of high purity and very good (low) detection limits. The combination of the various parts of the compound contributes to the properties needed to obtain suitable functionality for the various tracer applications.

Control of adsorption of both water and oil soluble compounds to e.g. formation or other parts present in a well together with very low limit of detection, makes these compounds especially suitable for permanent inflow monitoring in hydrocarbon producers. The stability of the compounds makes it possible to detect the compounds for years and decades after their injection or location (placement).

For use as unique chemical tracers, and in cases where the "homologue" tracer is deliberately used as one of several unique tracers in a wellbore, it is not preferable to have such same "homologues" in higher concentrations than 1%, originating from impurities and not from release of the real installed tracer.

For marking of fluids for permanent inflow monitoring, the combination of two or more compounds with tailored properties, either similar or different, could be implemented in a solid or degradable material, such as a polymer, ceramic, sand, shale, or onto completion equipment, tools or pipe and constitute a release system. The tracer system could also consist of other additives in combination with various compounds disclosed in the invention.

The compounds disclosed in the invention is also especially suitable for use related to oil production due to the method of detection related to extraction from well fluids and detection in level of ppb-ppq.

The compounds disclosed in the invention is also is also especially suitable for use as markers of fluids in combination with well and reservoir flow models and simulators for interpretation of inflow due to their large number of unique compounds combined with their comparable properties in the application and low level of detection.

DETAILED DESCRIPTION OF THE INVENTION

The invention relates to a compound characterized by the following generic structure:

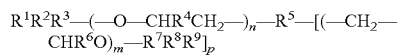

wherein the core unit $R^5$ is further connected to 2-4 units by carbon, ether or ester bonds;
$R^4$ and $R^6$ is H or —$CH_3$ to give PEG or PPG chains;
n and m are integers between 2 and 12 in which n could be the same or different from m;
p is an integer between 1 and 3 depending on $R^5$;
$R^3$ and $R^7$ are aliphatic or aromatic hydrocarbon or aralkyl moieties with 2-40 carbon coupled to the PEG units or the PPG units by an ester or ether bond;
$R^1$, $R^2$, $R^8$ and $R^9$ are all H or identical or different hydrophilic functional groups preferably carboxylic, sulfonic or phosphonic acid groups;
or salts, hydrates and solvates thereof,
with the exception of 1,2-bis(2-(2-(benzyloxy)ethoxy)ethoxy)benzene.

Preferably the invention relates to a compound above, wherein n and m are integers between 3 and 12.

Preferably the core $R^5$ unit consists of C, O and H atoms, but may also comprise S, P, X, M, N atoms in the form of (S)ulfonic acid groups, sulfonic acid salt thereof (SM), (P)hosphonic acid groups and salts thereof (PM), halogen atoms (X), and (N)itrogen containing groups.

Preferably the core $R^5$ unit is selected from aryl or aralkyl units with from 3 to 30 carbon atoms which also may contain one or more ether functions and/or ester functions; or branched or linear alkyl units with from 3 to 12 carbon atoms which also may contain one or more ether functions and/or ester functions.

More preferably the core $R^5$ unit is selected from aryl or aralkyl units with from 3 to 24 carbon atoms which also may contain one or more ether functions and/or ester functions or branched; or linear alkyl units with from 3 to 12 carbon atoms which also may contain one or more ether functions and/or ester functions Specifically more preferably the core $R^5$ unit is selected from aryl or aralkyl units with from 3 to 15 carbon atoms which also may contain one or more ether functions and/or ester functions or branched; or linear alkyl units with from 3 to 12 carbon atoms which also may contain one or more ether functions and/or ester functions The core $R^5$ can be selected from the group consisting of:

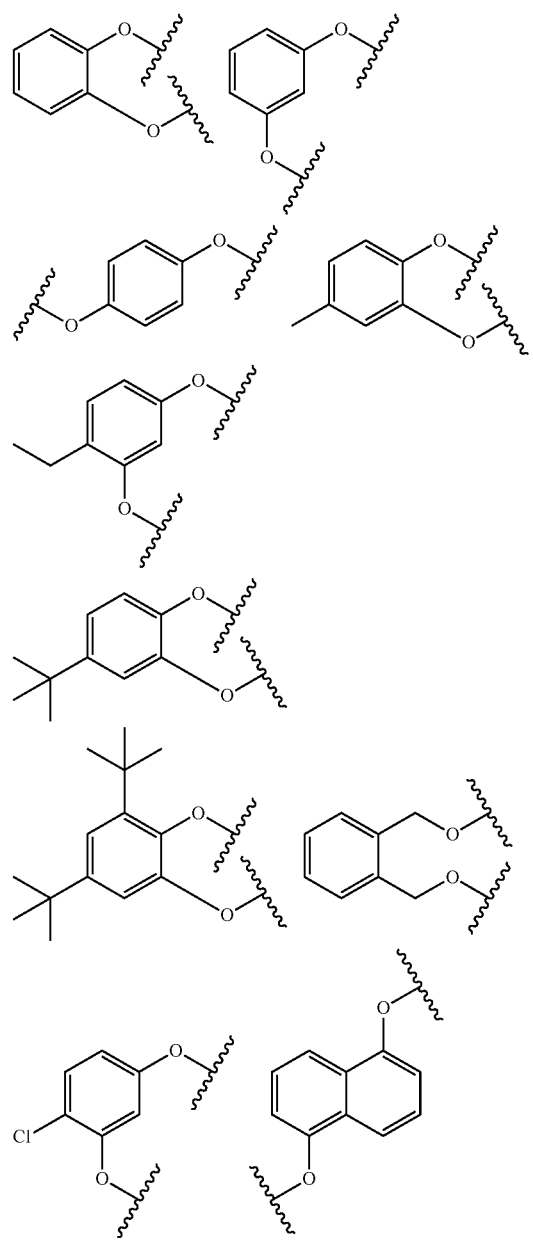

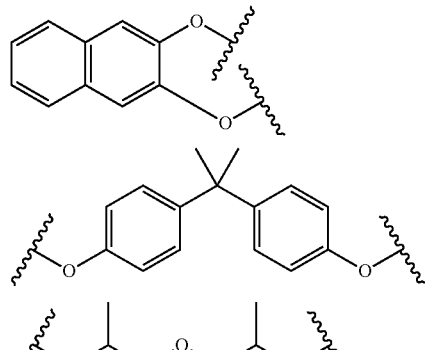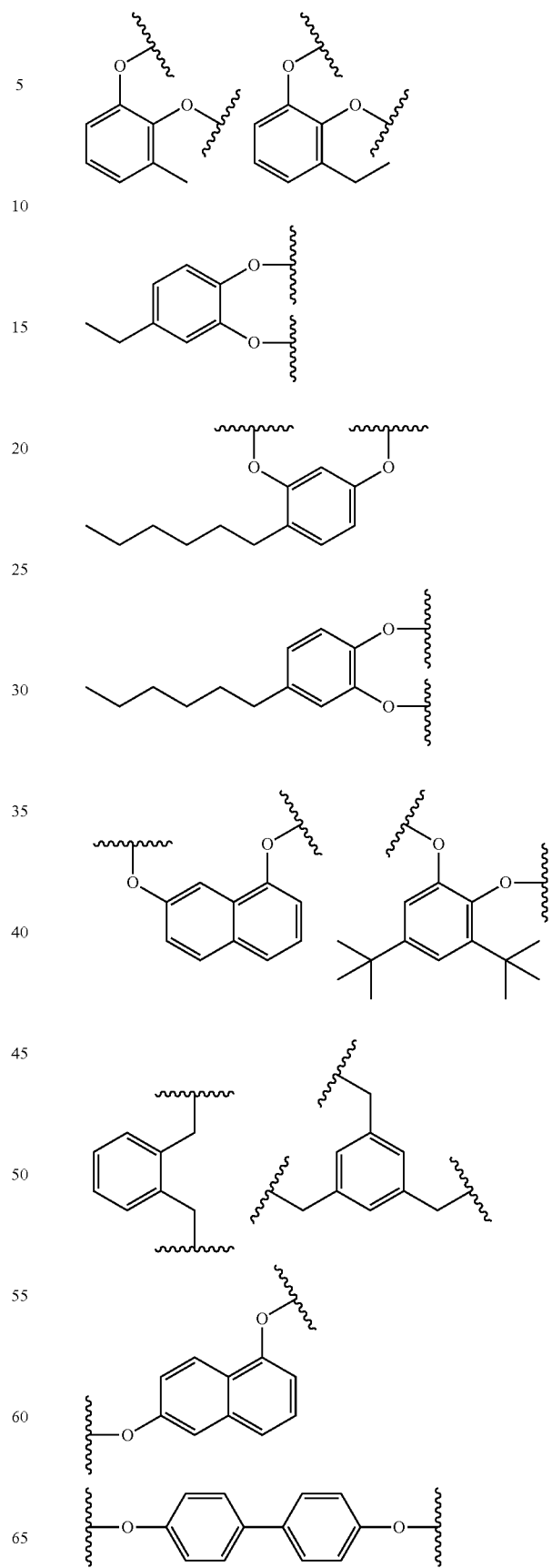

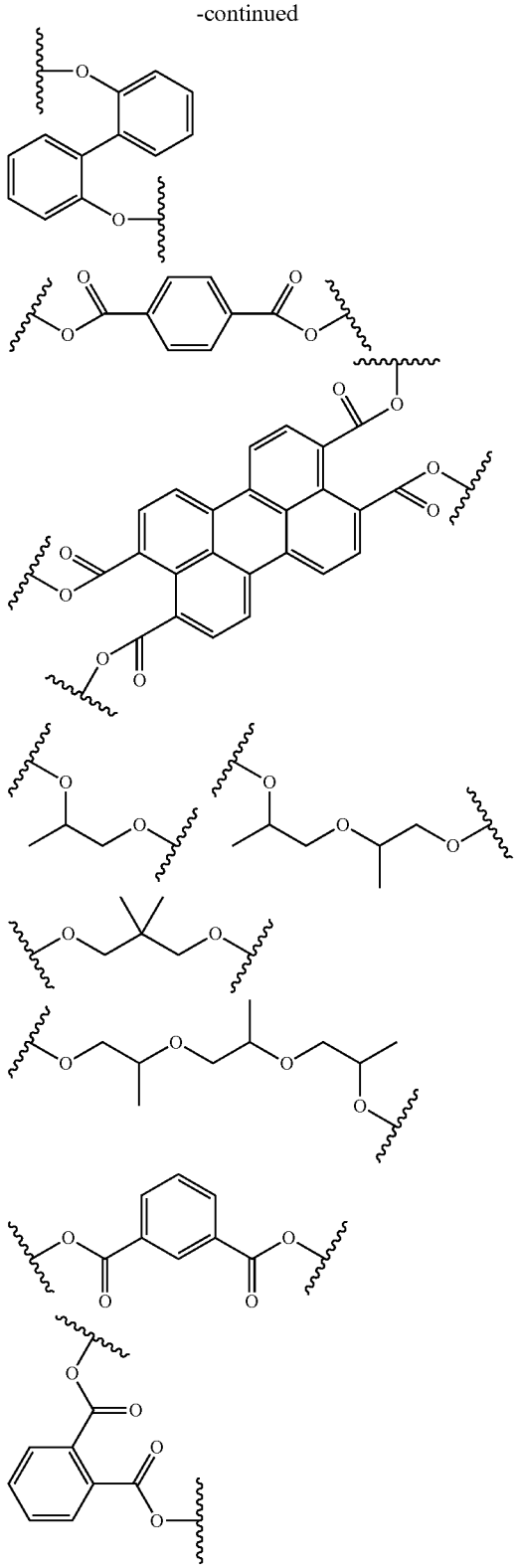

The above compounds may optionally be substituted by additional functional groups to enhance their detection as tracers by various detection methods like gas chromatography (GC), liquid chromatography (LC), mass spectrometry (MS) or a combination thereof, ultraviolet and visible spectroscopy, infrared and Raman spectroscopy, nuclear magnetic resonance (NMR) and detection of radiation coupled with suitable separation techniques like liquid column chromatography. The hydrophilicity of water soluble tracers having hydrophobic substituents can be altered by introducing sulfonic acid or sulfonic acid salts in the core molecule R5. In that way the solubility and the physicochemical properties of the tracers can be tailor made for the purpose.

The number of available oil soluble tracers can be increased by substituting the core molecule $R^5$ with halogens (X) and different types of linear or branched alkyl substituents in various positions

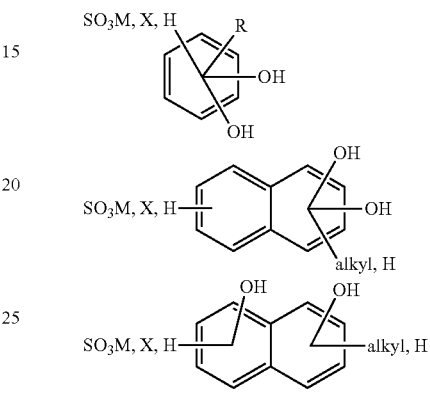

The above identified compounds can be selected from the list found in the examples.

The invention also relates to a composition containing one or more compounds as defined above and one or more additional constituents like solvents, diluents, surfactants, adsorbents, stabilizers and/or formulated into tablets or capsules.

The invention also relates to a compound characterized by the following generic structure

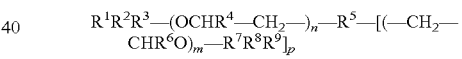

wherein the core unit $R^5$ is further connected to 2-4 units by carbon, ether or ester bonds;

$R^4$ and $R^6$ is H or $-CH_3$ to give PEG or PPG chains;

n and m are integers between 2 and 12 in which n could be the same or different from m;

p is an integer between 1 and 3 depending on $R^5$;

$R^3$ and $R^7$ are aliphatic or aromatic hydrocarbon or aralkyl moieties with 2-40 carbon coupled to the PEG units or the PPG units by an ester or ether bond;

$R^1$, $R^2$, $R^8$ and $R^9$ are all H or identical or different hydrophilic functional groups preferably carboxylic, sulfonic or phosphonic acid groups; or salts, hydrates and solvates thereof; or a composition containing one or more of these compounds and one or more additional constituents like solvents, diluents, surfactants, adsorbents, stabilizers and/or formulated into tablets or capsules;

for the use as a tracer.

The invention also relates to a compound or a composition as defined above for use as tracers in release systems.

The invention also relates to a compound or a composition as defined above for inflow monitoring during oil and gas production.

The invention also relates to a compound or a composition as defined above, wherein the components are detected topside after release from oil and gas wells.

The invention also relates to a compound or a composition as defined above, wherein the components are detected topside after release from oil and gas wells by LCMS, GCMS or a combination thereof.

Experimental

The LC-MS method development and analyses were performed on an Agilent 1100/1200 Series LC/MSD system (Agilent Technologies Inc., Palo Alto, Calif., USA). The system consists of a G1322A/G1379B mobile phase degassing unit, a G1311A quaternary pump with gradient mixer for up to four mobile phase constituents/G1312B binary pump with gradient mixer for up to two mobile phase constituents, a G1376A/G1367C autosampler, a G1330A/G1312B thermostat, a G1316A/G1316B column thermostat and a G1946D/G6130A single quadrupole mass spectrometer. Any equivalent LC-MS system may be used.

Scans were run using electrospray ionization in positive mode. 40% of a 50 mmolar solution of ammoniumacetate in acetonitrile (60%). 0.2 ml flow and direct injection without column separation.

Synthesis

The following synthetic pathways are to be regarded as examples on how to prepare the intermediates and end products including the examples of the application. The synthesis are well known to a person skilled in the art and the details like molar ratios, stoichiometry, solvents, volumes, temperatures, bases etc. can be varied to optimize the yields and purity.

The general synthesis procedures described in the present invention is meant to be examples, but should not be restricted to. The tosylation reaction may be replaced by a mesylation reaction or other activation reaction steps known to people skilled in the art. Further, the present compounds may be synthesized by e.g. addition reactions, condensation reactions or substitution reactions not shown in the examples Synthesis of Oil-Soluble Compounds The general synthesis is outlined in Scheme 2. Monotosylates, where n is an integer number from 1 to 8, are synthesized as in Scheme 1 or are commercially available.

Scheme 1

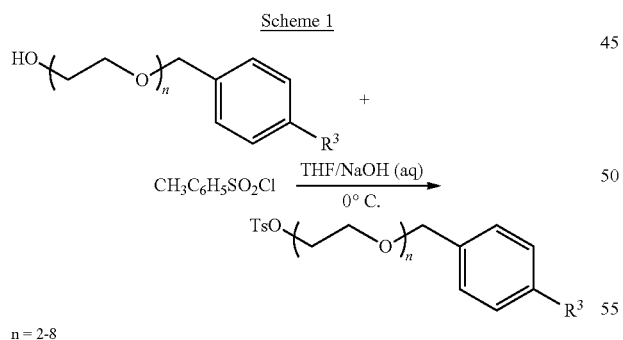

n = 2-8

Tosylation—General Procedure

NaOH (108 g, 2.70 mol) was dissolved in H$_2$O (1320 mL) and added a solution of monobenzyl-PEG4 (200 g, 0.703 mol) in THF (1200 mL). The mixture was cooled to 0° C. and added a solution of para-toluenesulfonyl chloride (228 g, 1.20 mol) in THF (800 mL) over 2 h. The white suspension was stirred at 0° C. for another 30 min, before THF was removed under vacuum (rotary evaporator, 40° C.). DCM (1500 mL) and H$_2$O (1500 mL) were added, the mixture was stirred for 5 min, and the phases were separated. The aqueous phase was extracted with DCM (2×1500 mL), and the combined organic extracts were dried (Na$_2$SO$_4$), filtered and concentrated (rotary evaporator, 40° C.) to give the product (320 g) as a pale yellow oil.

Scheme 2

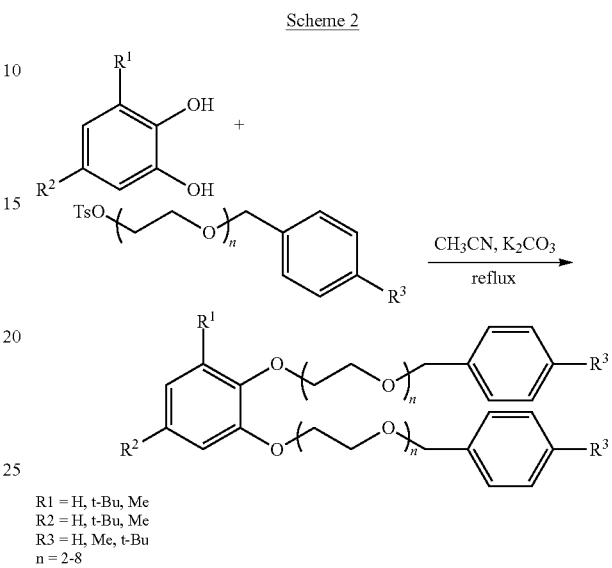

R1 = H, t-Bu, Me
R2 = H, t-Bu, Me
R3 = H, Me, t-Bu
n = 2-8

Scheme 2 is also relevant for examples wherein 1,3,5-trihydroxybenzene, 2,2-bis(4-hydroxyphenyl)propane, 2,3-dihydroxynaphtalene or 1,5-dihydrxonaphtalene are the core molecules (R$^5$) and compounds wherein 3-phenylbenzyl and 2-methylnaphtalane are the terminating groups.

General Procedure of Ether Compounds

A mixture of K$_2$CO$_3$ (4.5 eq) in MeCN (800 ml/mol) was heated to reflux. A mixture of the catechol (1 eq) and the tosylate (2.2 eq) in MeCN (1400 ml/mol catechol) was slowly added, and the reflux was continued for 4 days. After cooling the temperature to 50 degrees, ethanolamine (25 ml/mol tosylate) was added and the mixture was refluxed for another 2 h. It was then cooled to room temperature, and diluted with 1 vol CH$_2$Cl$_2$. The salts were filtered off and washed with some CH$_2$Cl$_2$. After removal of the solvents, the residue is dissolved in CH$_2$Cl$_2$ and washed with 1M HCl (aq) (2×), and with water, then dried (Na$_2$SO$_4$) and concentrated in vacuo.

Procedures for examples of oil-soluble compounds with substituted resorcinol in the core molecule (R5) is outlined in Scheme 3:

Scheme 3

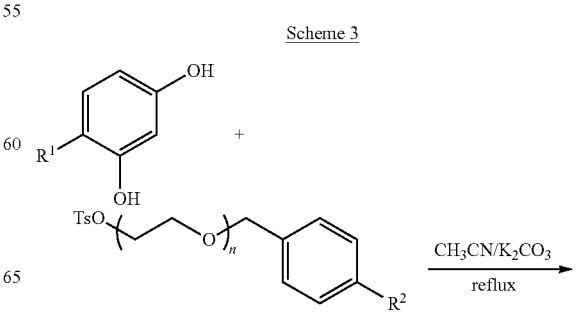

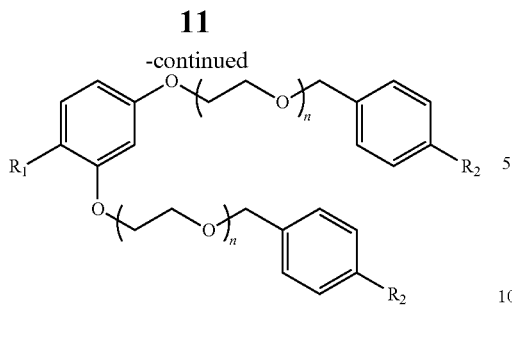

R1 = H, Et, Cl
R2 = H, Me
n = 2-8

Figure 12:
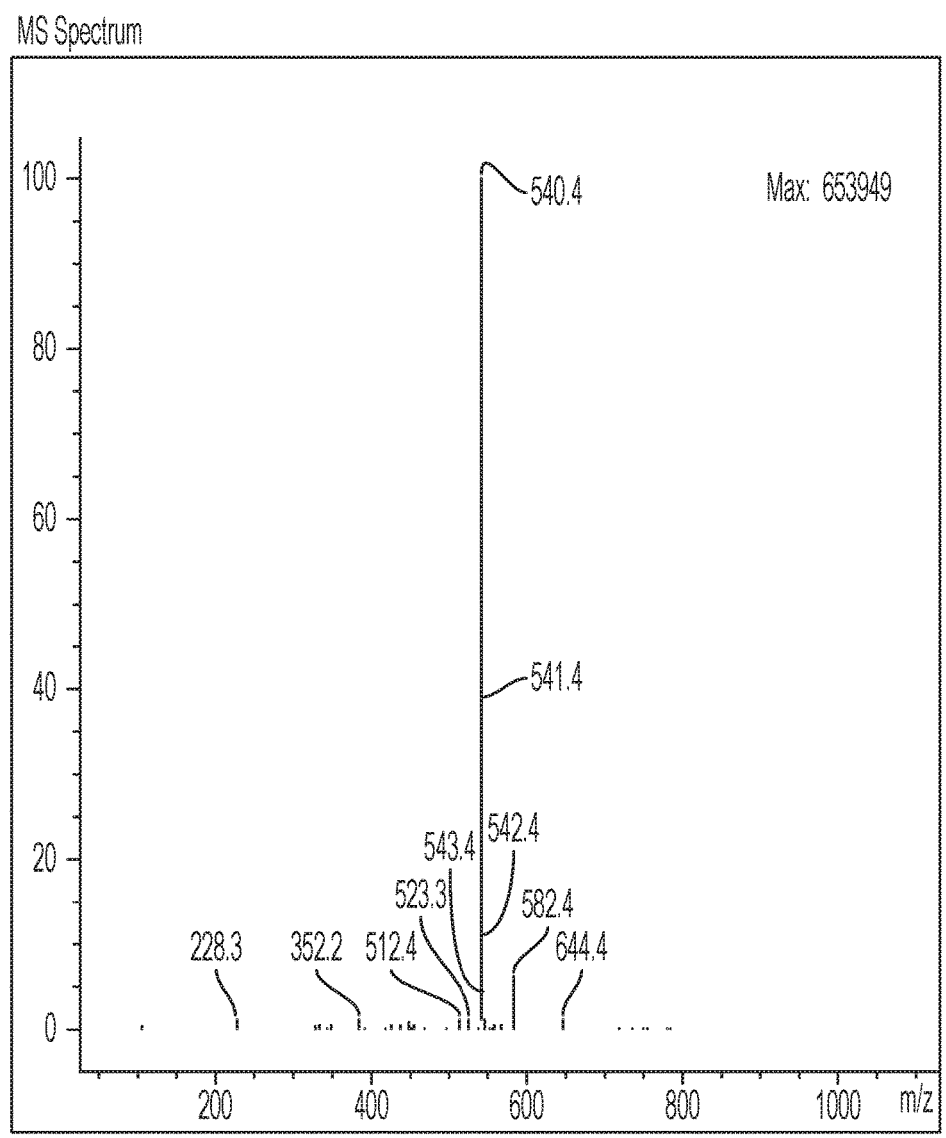

The following specific procedures are provided as examples for the synthesis of oil-soluble compounds found among the examples:

4,4'-((((((((4-ethyl-1,3-phenylene)bis(oxy))bis(ethane-2,1-diyl))bis(oxy))bis(ethane-2,1-diyl))bis(oxy))bis(methylene))bis(methylbenzene), example 11 and MS data in FIG. 12

A mixture of $K_2CO_3$ (21.46 g) in MeCN (143 ml) was heated to reflux. A mixture of the 4-chloro resorcinol (4.76 g) and the tosylate (30.12 g) in MeCN (56 ml) was slowly added, and the reflux was continued for 4 days. After cooling the temperature to 50 degrees, ethanolamine (2.90 ml) was added and the mixture was refluxed for another 2 h. It was then cooled to room temperature, and diluted with 258 ml $CH_2Cl_2$. The salts were filtered off and washed with $CH_2Cl_2$. After removal of the solvents, the residue is dissolved in $CH_2Cl_2$ (200 ml) and washed with 1M HCl (aq) (2×200 ml), and with water, then dried ($Na_2SO_4$) and concentrated in vacuo to give 16.6 g (92% yield) as a brown liquid.

Figure 13:
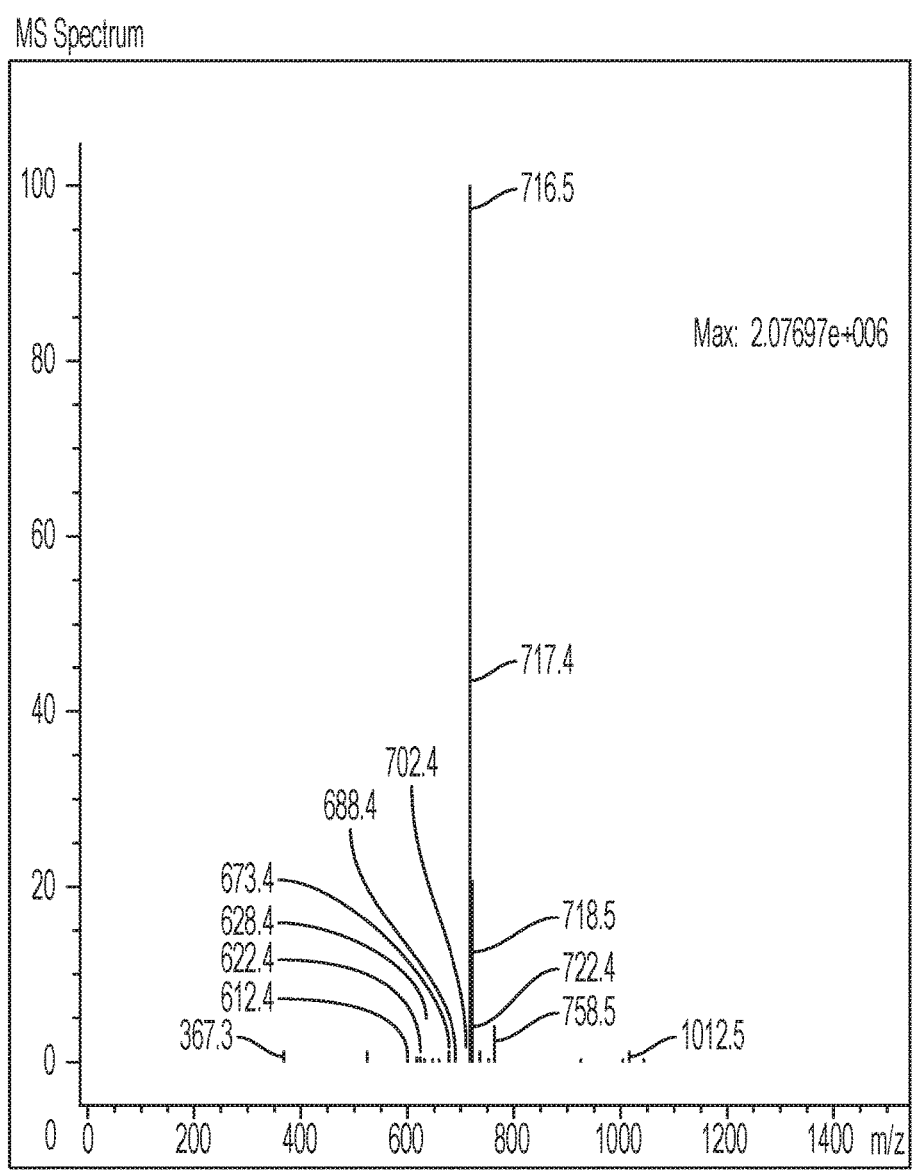

13,13'-((4-ethyl-1,3-phenylene)bis(oxy))bis(1-(p-tolyl)-2,5,8,11-tetraoxatridecane) Example 12 and MS Data in FIG. 13

A mixture of $K_2CO_3$ (17.68 g) in MeCN (102 ml) was heated to reflux. A mixture of the 4-chloro resorcinol (4.09 g) and the tosylate (30.82 g) in MeCN (40 ml) was slowly added, and the reflux was continued for 4 days. After cooling the temperature to 50 degrees, ethanolamine (2.39 ml) was added and the mixture was refluxed for another 2 h. It was then cooled to room temperature, and diluted with 197 ml $CH_2Cl_2$. The salts were filtered off and washed with $CH_2Cl_2$. After removal of the solvents, the residue is dissolved in $CH_2Cl_2$ (200 ml) and washed with 1M HCl (aq) (2×200 ml), and with water, then dried ($Na_2SO_4$) and concentrated in vacuo to give 17.2 g (86% yield) as an orange liquid.

Figure 14:
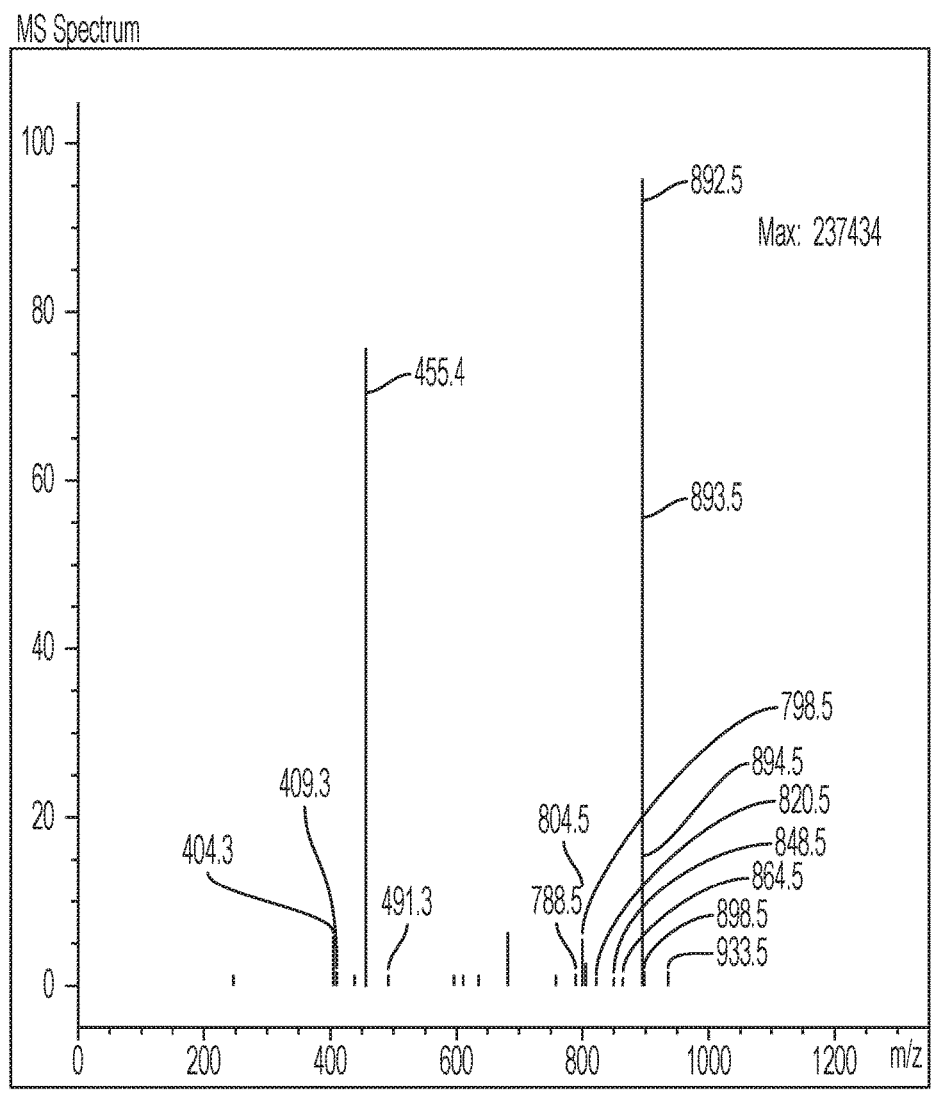

19,19'-((4-ethyl-1,3-phenylene)bis(oxy))bis(1-(p-tolyl)-2,5,8,11,14,17-hexaoxanonadecane), example 13 and MS data in FIG. 14

A mixture of $K_2CO_3$ (17.8 g) in MeCN (103 ml) was heated to reflux. A mixture of the 4-chloro resorcinol (3.95 g) and the tosylate (37.07 g) in MeCN (40 ml) was slowly added, and the reflux was continued for 4 days. After cooling the temperature to 50 degrees, ethanolamine (2.40 ml) was added and the mixture was refluxed for another 2 h. It was then cooled to room temperature, and diluted with 204 ml $CH_2Cl_2$. The salts were filtered off and washed with $CH_2Cl_2$. After removal of the solvents, the residue is dissolved in $CH_2Cl_2$ (200 ml) and washed with 1M HCl (aq) (2×200 ml), and with water, then dried ($Na_2SO_4$) and concentrated in vacuo to give 22.5 g (90% yield) as an orange liquid.

Figure 15:
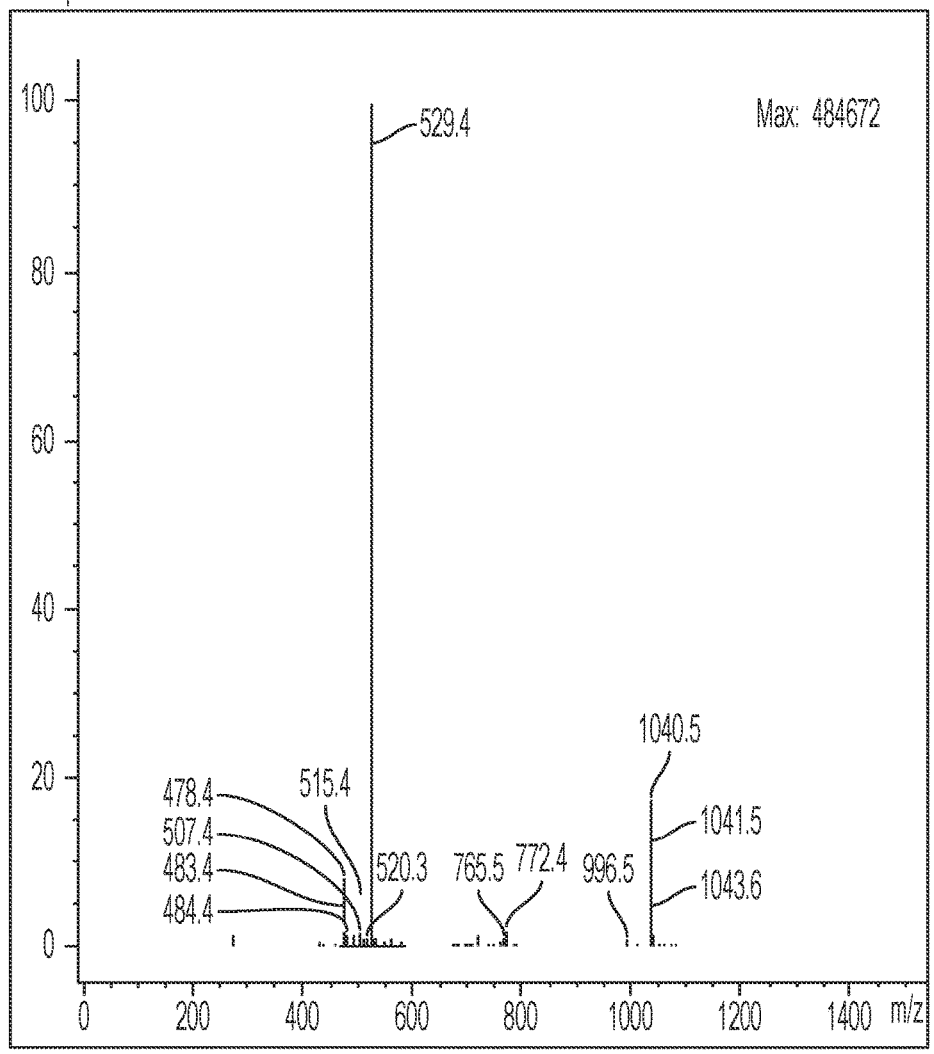

25,25'-((4-ethyl-1,3-phenylene)bis(oxy))bis(1-phenyl-2,5,8,11,14,17,20,23-octaoxapentacosane), example 14 and MS data in FIG. 15

A mixture of $K_2CO_3$ (15.22 g) in MeCN (88 ml) was heated to reflux. A mixture of the 4-chloro resorcinol (3.38 g) and the tosylate (36.05 g) in MeCN (34 ml) was slowly added, and the reflux was continued for 4 days. After cooling the temperature to 50 degrees, ethanolamine (2.05 ml) was added and the mixture was refluxed for another 2 h. It was then cooled to room temperature, and diluted with 179 ml $CH_2Cl_2$. The salts were filtered off and washed with $CH_2Cl_2$. After removal of the solvents, the residue is dissolved in $CH_2Cl_2$ (200 ml) and washed with 1M HCl (aq) (2×200 ml), and with water, then dried ($Na_2SO_4$) and concentrated in vacuo to give 24.3 g (97% yield) as an orange liquid.

Figure 16:
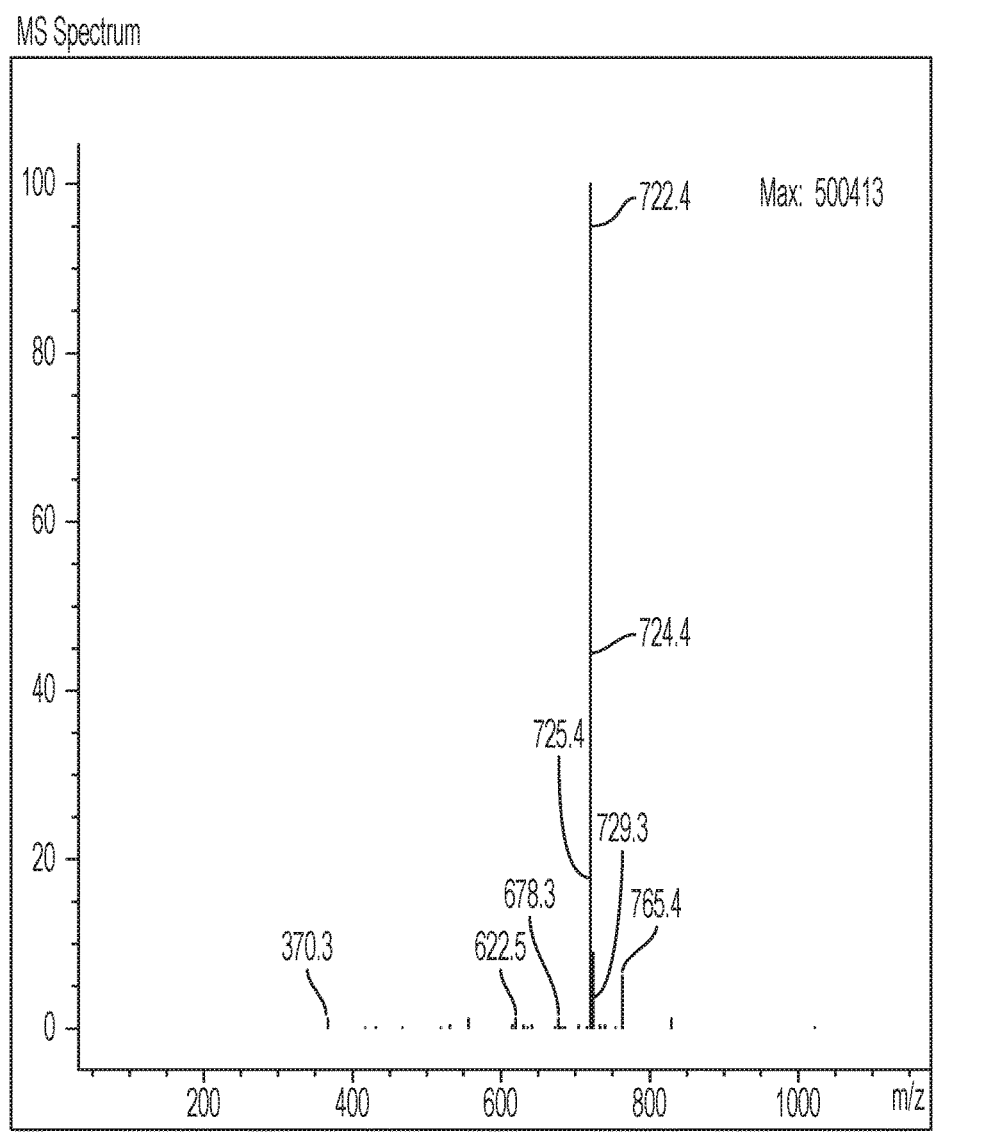

13,13'-((4-chloro-1,3-phenylene)bis(oxy))bis(1-(p-tolyl)-2,5,8,11-tetraoxatridecane), Example 15 and MS Data in FIG. 16

A mixture of $K_2CO_3$ (17.68 g) in MeCN (102 ml) was heated to reflux. A mixture of the 4-chloro resorcinol (4.09 g) and the tosylate (30.82 g) in MeCN (40 ml) was slowly added, and the reflux was continued for 4 days. After cooling the temperature to 50 degrees, ethanolamine (2.39 ml) was added and the mixture was refluxed for another 2 h. It was then cooled to room temperature, and diluted with 197 ml $CH_2Cl_2$. The salts were filtered off and washed with $CH_2Cl_2$. After removal of the solvents, the residue is dissolved in $CH_2Cl_2$ (200 ml) and washed with 1M HCl (aq) (2×200 ml), and with water, then dried ($Na_2SO_4$) and concentrated in vacuo to give 17.2 g (86% yield) as an orange liquid.

Synthesis of Water-Soluble Compounds

A general procedure for a 2-step reaction for water-soluble compounds is outlined in Scheme 4. The procedure is also valid for compounds wherein dihydroxynaphtalene or substituted resorcinol are the core molecules.

Scheme 4

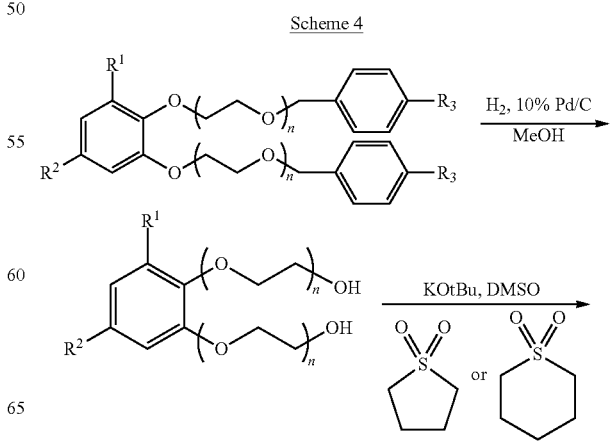

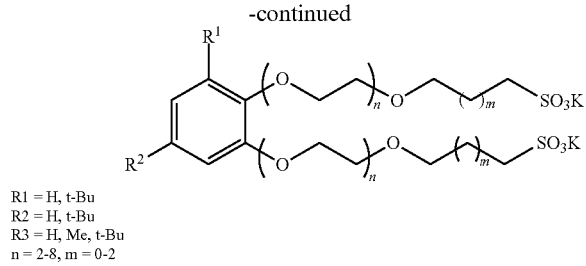

R1 = H, t-Bu
R2 = H, t-Bu
R3 = H, Me, t-Bu
n = 2-8, m = 0-2

Hydrogenation

To a 10% solution of the oil soluble intermediate in methanol in an argon-flushed flask, about 5% (based on oil soluble intermediate mass) of 10% Pd(C) is added. The flask is flushed with hydrogen, and the mixture is stirred vigorously overnight. It is then filtered through a plug of celite and then concentrated in vacuo to give the diol in almost quantitative yield.

Sutton Reaction

The diol is dissolved in DMSO, and 2.4 eq. KOtBu is added. The mixture is then heated to 40 C under vacuum for 2 h in order to evaporate the tBuOH formed. After cooling to room temperature, 2.4 eq. 1,3-propanesultone in some DMSO is added. The mixture is then stirred at 60 C overnight before the DMSO is removed in vacuo (ca. 12 mbar/90 C). The residue is dissolved in a minimal amount of methanol, and the product is precipitated by addition of 5 vol acetone. The product is isolated by centrifugation, washed with some acetone, and then dried in vacuo. Yields vary depending on product structure, and amount of DMSO and methanol present during precipitation. By concentrating the mother-liquor and repeating the precipitation, a second crop may be obtained, resulting in acceptable yield of the RGTW.

Alternative Sulton Reaction

A solution of the diol (3.0 g, 6.5 mmol, 1 equiv.) and 1,3-propanesultone (2.17 g, 17.8 mmol, 2.7 equiv.) in THF (6 mL) was warmed to 60° C. and added a solution of KOtBu (2.01 g, 17.9 mmol, 2.7 equiv.) in THF (14 mL) over 15 min. Additional THF (10 mL) was added to help stirring. The resulting suspension was cooled to rt and stirred over night.

THF was removed under vacuum after 20 h at rt. The resulting solid was dissolved in minimal amounts of MeOH (150 mL) under reflux. The solution was poured into acetone (450 mL) to result in a cloudy mass not possible to isolate by filtration. The solvent was removed under vacuum, and the resulting solid was analyzed by HPLC. Any type of sultone may be used as reagent for introducing e.g. sulfonic acid functionality and useful properties such as steric effects.

General Procedure of Ester Compounds

Synthesis of ester based compounds through reactions of alcohols and acid chlorides is shown below. The detail description is for synthesis of tris(1-phenyl-2,5,8,11-tetraoxatridecan-13-yl) benzene-1,3,5-tricarboxylate. However the same general procedure, adjusted only with respect to stoichiometry, can be used to synthesize similar mono, di or tetra substituted aromatic esters from corresponding acid chlorides or di-esters of non-aromatic acid chlorides.

Scheme 5

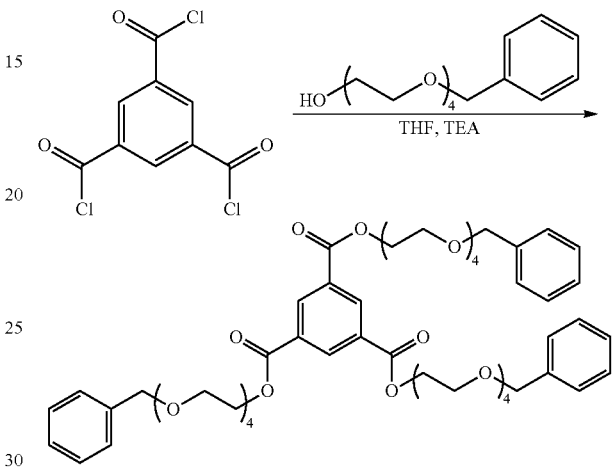

A three neck round bottle (100 ml) equipped with a stirrer and thermometer was loaded with THF (3.6 ml) and then TEA (0.89 g, 8.81 mmol) was added under stirring for 2 min. While stirring a solution of tetra ethylene glycol-monobenzyl ether (3.00 g, 8.81 mmol) in dry THF (3 ml) was added. The reaction was stirred for 30 min. at room temperature, and then cooled to 0° C. A solution of 1,3,5-benzene-tricarbonyltrichloride (0.73 g, 2.75 mmol) in dry THF (1 ml) was drop-wise added in a rate not allowing the reaction temperature to exceed 27° C. After addition the reaction mixture was stirred for another 2.5 hours, then centrifuged at 4000 rpm for 10 min. The THF phase was isolated, precipitate washed with THF (2×10 ml) and the combined THF phase was concentrated under reduced pressure. The residual oil was extracted with water (3×10 ml, pH=6.7), organic phase dried with anhydrous sodiumsulphate and concentrated under reduced pressure to give the product (yield 81%). The pure product was obtained by flash chromatography (MS spectrum for the respectively crude and purified product are shown in MS spectrum nr 3 and 4.

A general synthesis method for etherification of propylene glycol derivatives, here shown by use of di-propyleneglycol is found in scheme 6.

Scheme 6

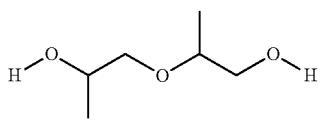

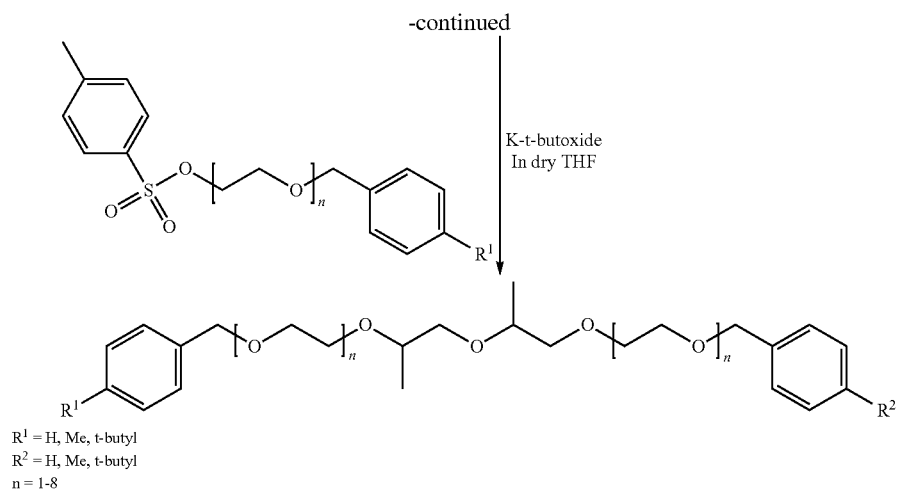

R¹ = H, Me, t-butyl
R² = H, Me, t-butyl
n = 1-8

Figure 22:
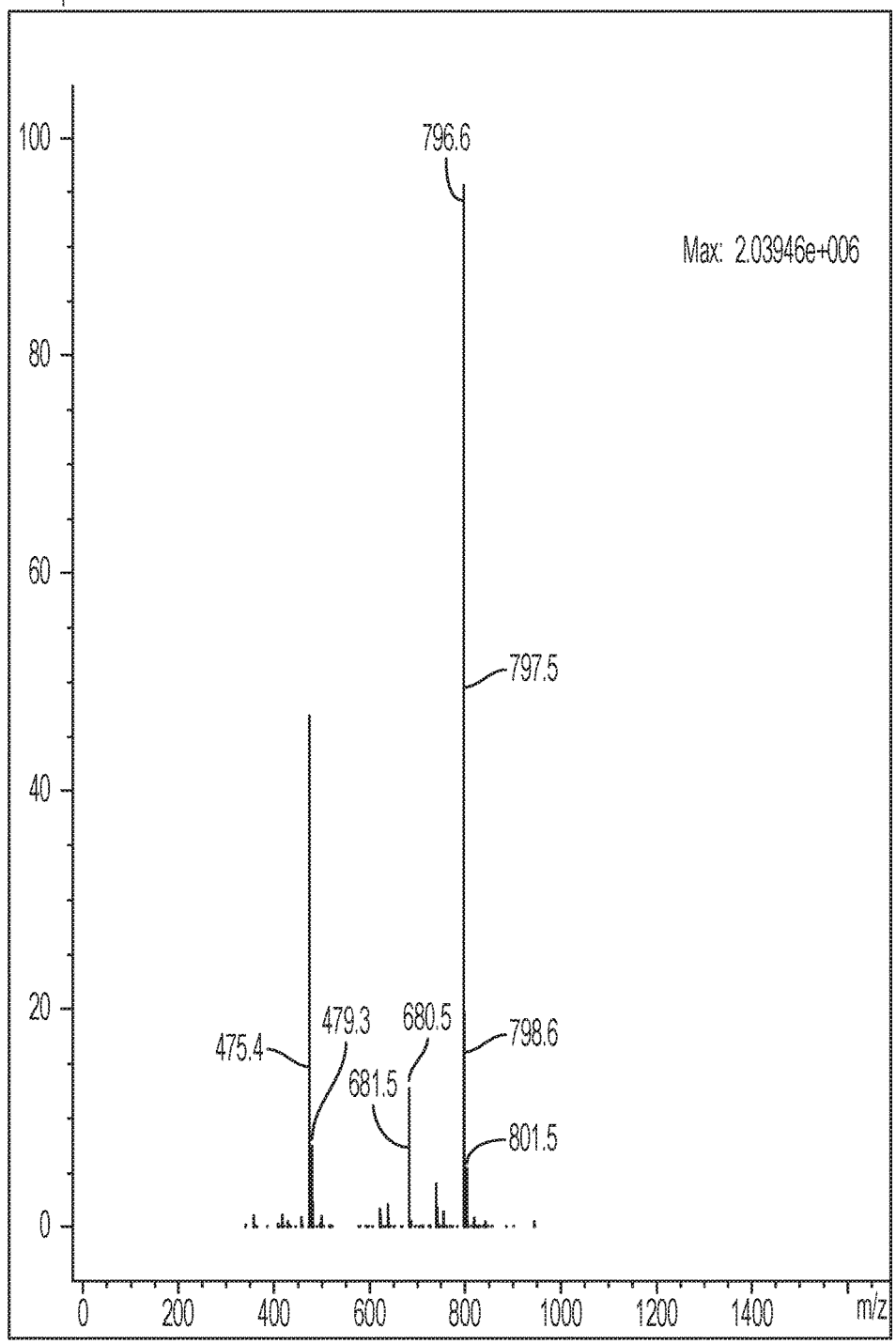

1,33-bis(4-(tert-butyl)phenyl)-15,19-dimethyl-2,5,8,11,14,17,20,23,26,29,32-undecaoxatritriacontane was synthesized according to scheme 6 where $R^1=R^2$=t-butyl and n=4. A thermostat regulated glass reactor equipped with mechanical stirrer was loaded with a slurry of potassium-t-butoxide (2.51 g, 22.36 mmol) in dry THF (10 ml). At 20° C., a solution of di-propylene glycol (1.5 g, 11.18 mmol) in dry THF (10 ml) was dropwise added, and the reaction mixture was stirred over night at room 20° C. The solvent and the formed t-butanole was removed by evaporation at 83° C. under stirring. At 22° C., dry THF (20 ml) was added to gain a new fine slurru. While stirring at 3° C., a solution of t-butyl benzyl-tetra ethyleneglycol-mono tosylate (11.5 g) in dry THF (50 ml) was dropwise added and the reaction mixture was further stirred at room temperature over night. The reaction mixture was filtrated and the oil phase concentrated under reduced pressure to give the product. MS spectrum no 22 is shown in FIG. 22, example 21

A general synthesis method for etherfication of alpha, alpha'-Dibromo-o-xylenederivatives is found in scheme 7.

Scheme 7

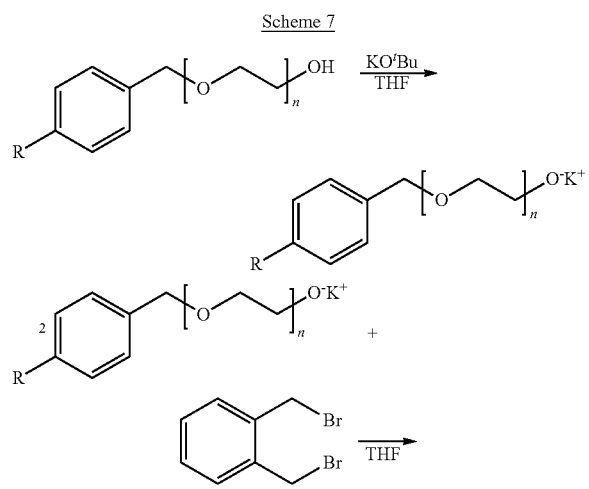

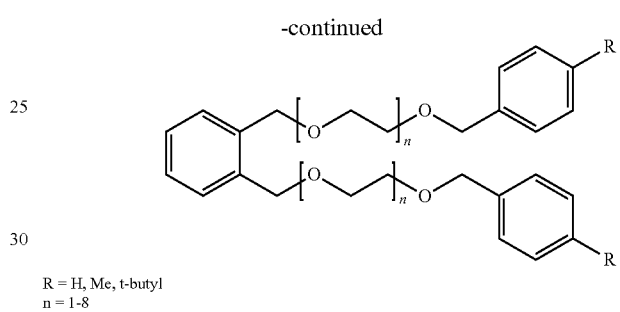

R = H, Me, t-butyl
n = 1-8

1,2-bis(15-(4-(tert-butyl)phenyl)-2,5,8,11,14-pentaoxapentadecyl)benzene was synthesized according to scheme 7 where R=t-butyl and n=4. KOtBu (20.0 g, 178 mmol) was dissolved in THF (200 m) and tetraethylene glycol mono (tertbuthyl)benzyl ether (60 g, 176 mmol) in THF (50 ml) was added dropwise. After 1 hour THF (together with formed tBuOH) was removed in vacuo, and another 200 ml THF was added. 1,2-bis(bromomethyl)benzene (23 g, 87 mmol) in THF (100 ml) was then added slowly.

Figure 19:
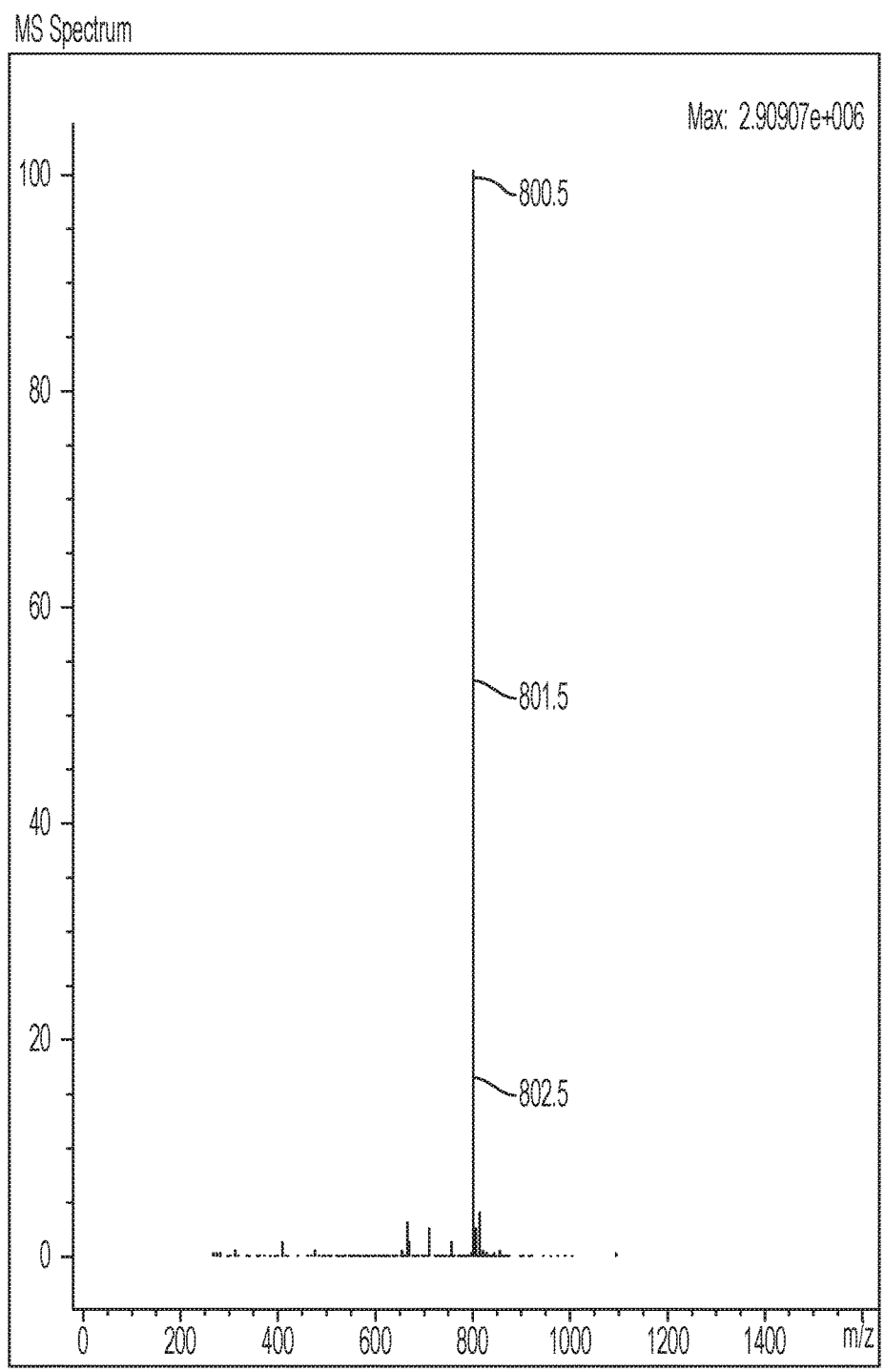

After one night, the reaction mixture was filtered, evaporated, and partitioned between methylene chloride and water. The aqueous phase was extracted with more dichloromethane, and the combined organic phases were dried ($Na_2SO_4$) and evaporated to give 61.0 g product. MS spectrum no 19 is shown in FIG. 19, example 18.

1,2-bis(15-phenyl-2,5,8,11,14-pentaoxapentadecyl)benzene was synthesized according to scheme 7 where R=t-butyl and n=4. KOtBu (21 g, 187 mmol) was dissolved in THF (200 m) and tetraethylene glycol monobenzyl ether (52 g, 182 mmol) in THF (50 ml) was added dropwise. After 1 hour THF (together with formed tBuOH) was removed in vacuo, and another 200 ml THF was added. 1,2-bis(bromomethyl)benzene (24 g, 90 mmol) in THF (100 ml) was then added slowly.

Figure 20:
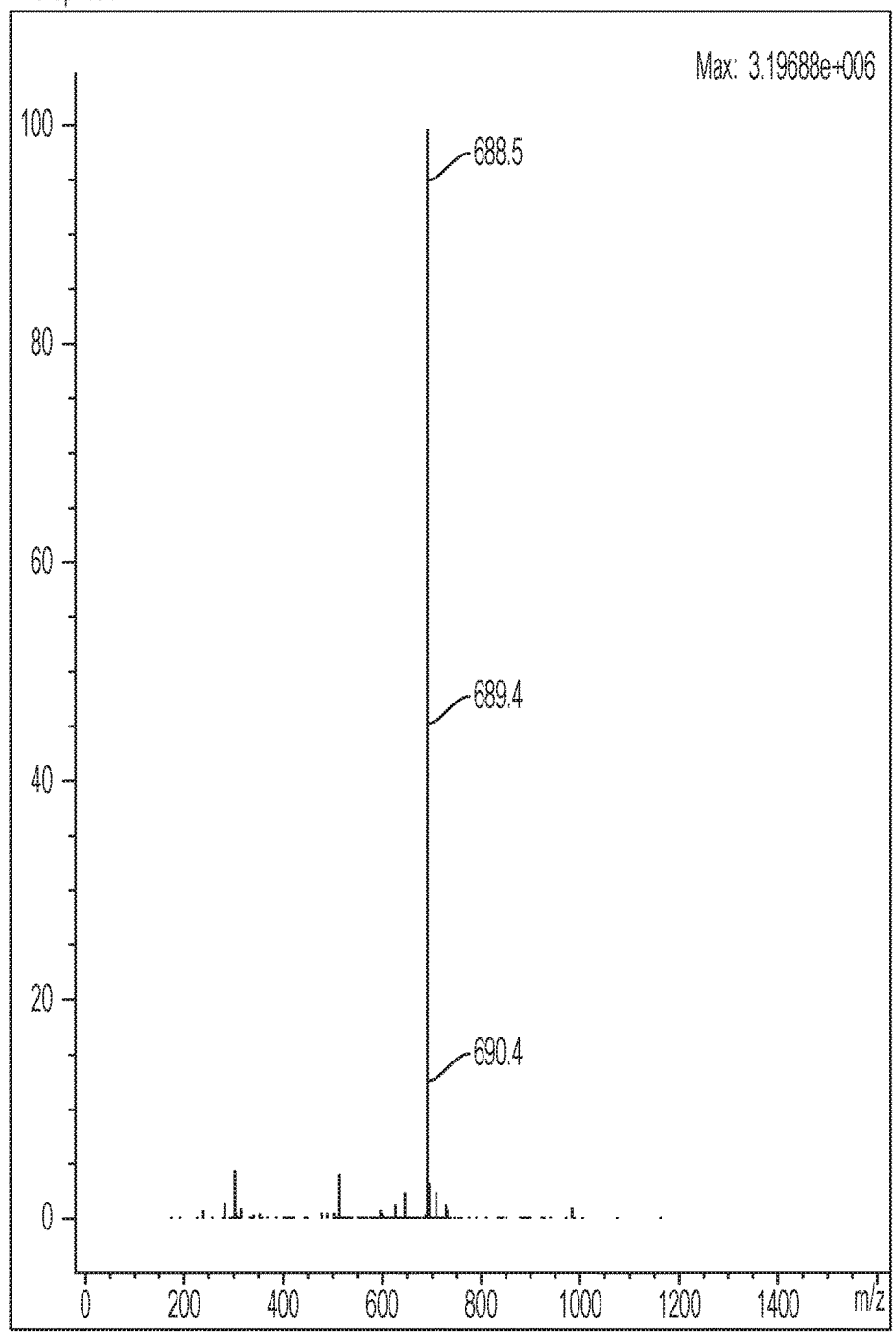

After one night, the reaction mixture was filtered, evaporated, and partitioned between methylene chloride and water. The aqueous phase was extracted with more dichloromethane, and the combined organic phases were dried ($Na_2SO_4$) and evaporated to give 60.0 g product. MS spectrum no 20 is shown in FIG. 20, example 19.

1,2-bis(27-phenyl-2,5,8,11,14,17,20,23,26-nonaoxaheptacosyl)benzene was synthesized according to scheme 7 where $R^1$=H and n=8. KOtBu (11.78 g, 105 mmol) was dissolved in THF (200 m) and octaethylene glycol monobenzyl ether (46.0 g, 100 mmol) in THF (50 ml) was added dropwise. After 15 min THF (together with formed tBuOH) was removed in vacuo, and another 200 ml THF was added. 1,2-bis(bromomethyl)benzene (13.2 g, 50 mmol) in THF (50 ml) was then added slowly.

Figure 21:
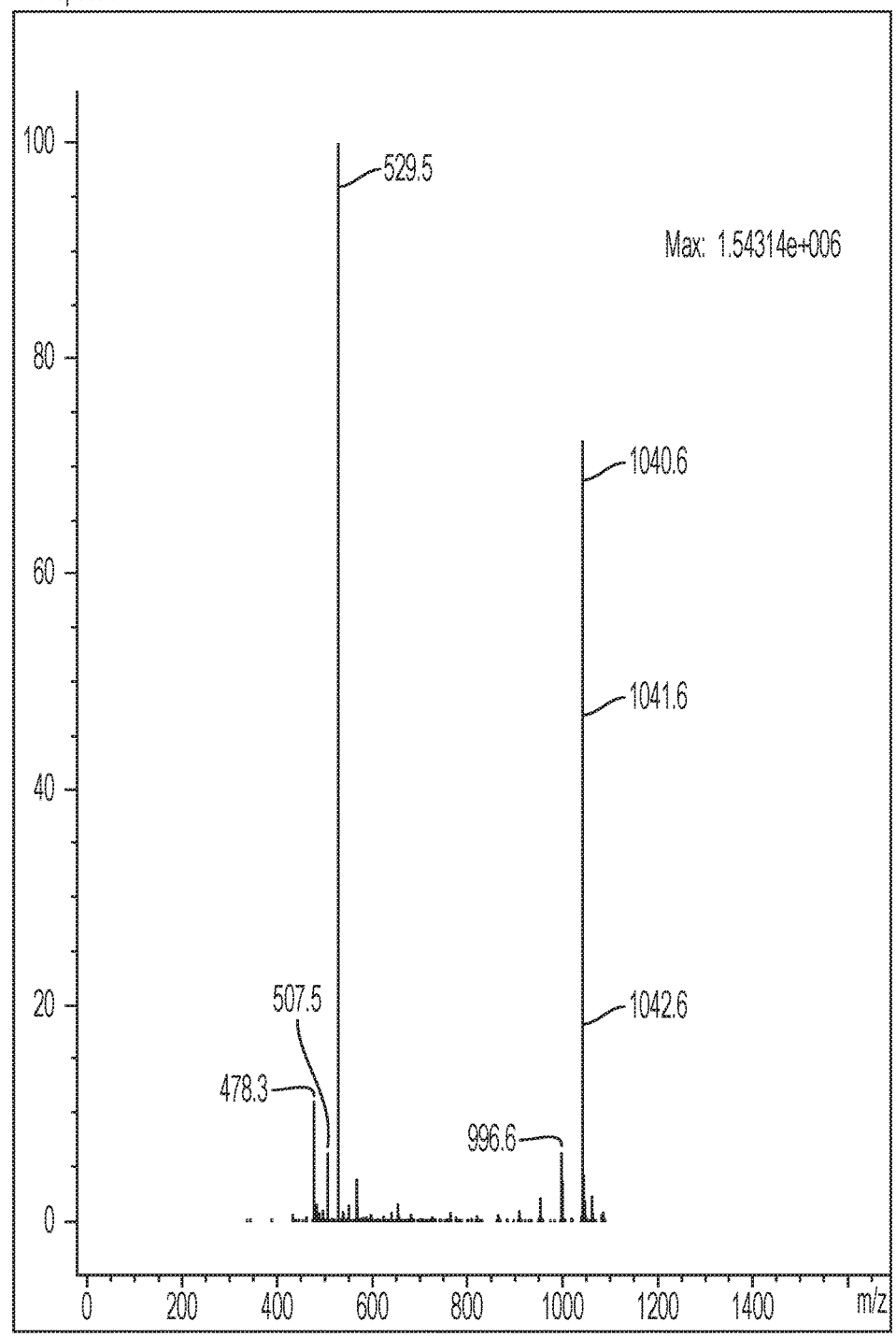

After one night, the reaction mixture was filtered, evaporated, and partitioned between methylene chloride and water. The aqueous phase was extracted with more dichloromethane, and the combined organic phases were dried (Na$_2$SO$_4$) and evaporated to give 41.2 g product. MS spectrum no 21 is shown in FIG. 21, example 20

A general synthesis method for etherification of 1,4-dihydroxybutane derivatives, here shown bus reaction with 1,4-di-hydroxybutane (scheme 8)

Scheme 8

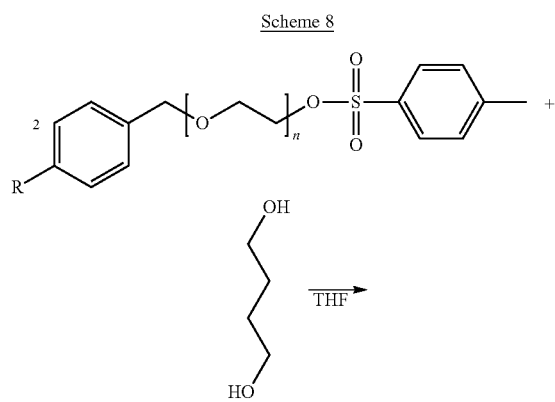

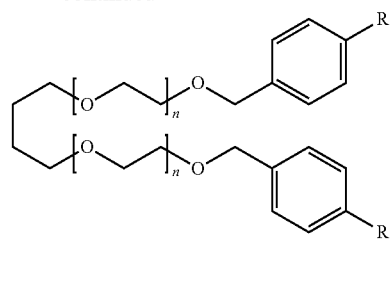

R = H, Me, t-butyl
n = 1-8

1,32-diphenyl-2,5,8,11,14,19,22,25,28,31-decaoxadotriacontane was synthesized according to scheme 8 where R$^1$=H and n=4. 1,4-butandiol (200 mg, 2.2 mmol) was dissolved THF (5 mL) and KOtBu (500 mg, 4.5 mmol) dissolved in 5 mL THF was added slowly. After 1 hour tosyl tetraethylene glycol monobenzyl ether (2 g, 4.56 mmol) in THF (10 ml) was added dropwise. After 1 hour THF was removed in vacuo.

Figure 23:
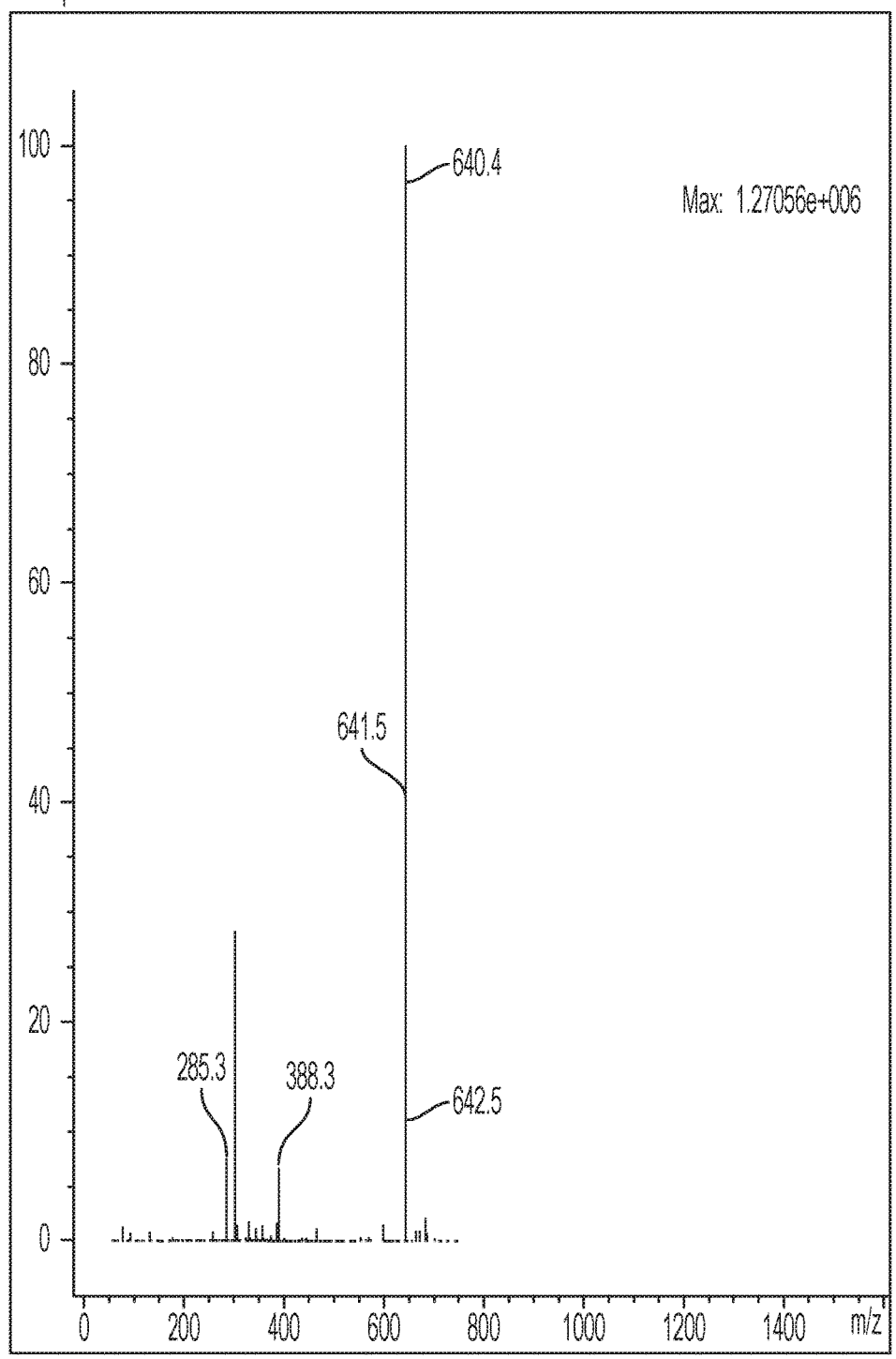

After one night, the reaction mixture was filtered, evaporated, and partitioned between methylene chloride and water. The aqueous phase was extracted with more dichloromethane, and the combined organic phases were dried (Na$_2$SO$_4$) and evaporated to give 500 mg product. MS spectrum no 23 is shown in FIG. 23, example 22.

A general synthesis method for etherification of 1,3,5-tris-(Hydroxymethyl)benzene derivatives (scheme 9)

Scheme 9

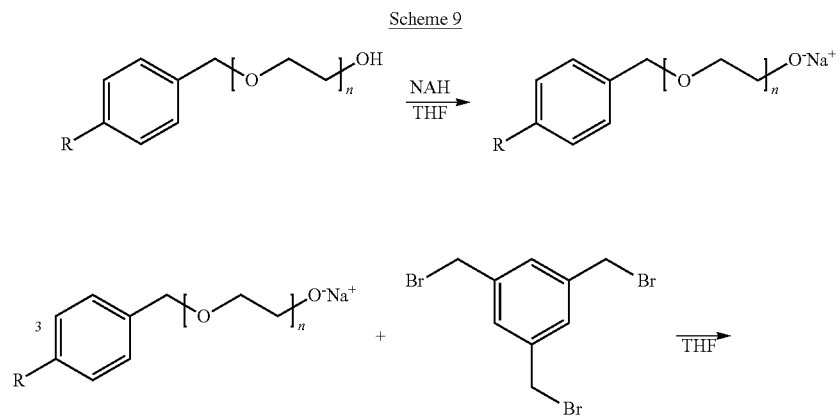

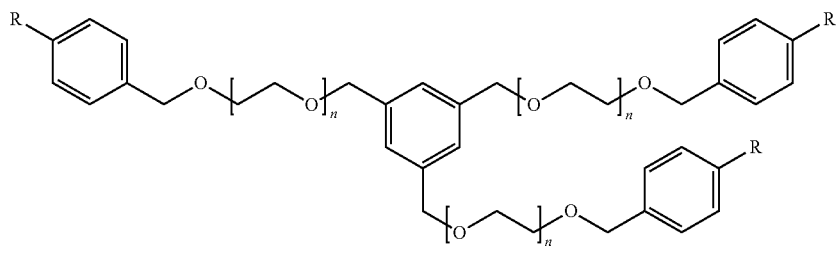

R = H, Me, t-butyl
n = 1-8

1,3,5-tris(15-phenyl-2,5,8,11,14-pentaoxapentadecyl) benzene was synthesized according to scheme 9 where R=H and n=4. In an argon-flushed flask, sodium hydride (50% in oil, 3.6 g, 75 mmol) was washed twice with cyclohexane to remove the oil. THF (200 ml) was added, followed by tetraethylene glycol monobenzyl ether (17.04 g, 60 mmol). The mixture was heated to 40 degrees C. until the evolution of gas diminished. A solution of 1,3,5-tris(bromomethyl) benzene (7.13 g, 20 mmol) in THF (50 ml) was added dropwise, and the reaction continued at 40 degrees C.

Figure 24:
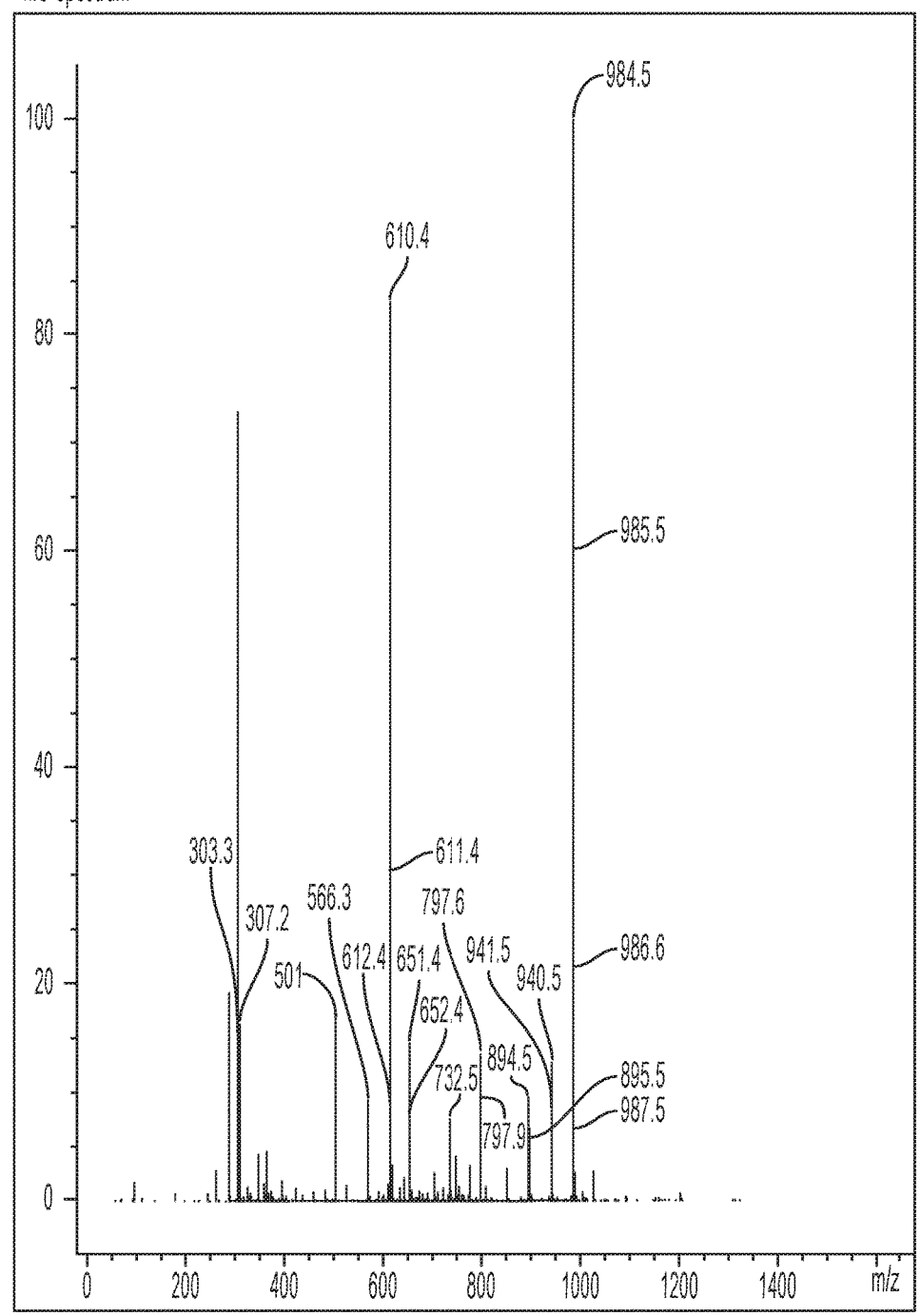

After two nights, the reaction mixture was filtered, concentrated in vacuo, and partitioned between water and dichloromethane. The organic phase was dried and concentrated to give the product. MS spectrum no 24 is shown in FIG. 24, example 23.

1,3,5-tris(27-phenyl-2,5,8,11,14,17,20,23,26-nonaoxaheptacosyl)benzene was synthesized according to scheme 9 where R=H and n=8. In an argon-flushed flask, sodium hydride (50% in oil, 3.6 g, 75 mmol) was washed twice with cyclohexane to remove the oil. THF (200 ml) was added, followed by octaethylene glycol monobenzyl ether (27.6 g, 60 mmol). The mixture was heated to 40 degrees C. until the evolution of gas diminished. A solution of 1,3,5-tris(bromomethyl)benzene (7.13 g, 20 mmol) in THF (50 ml) was added dropwise, and the reaction continued at 40 degrees C.

Figure 25:
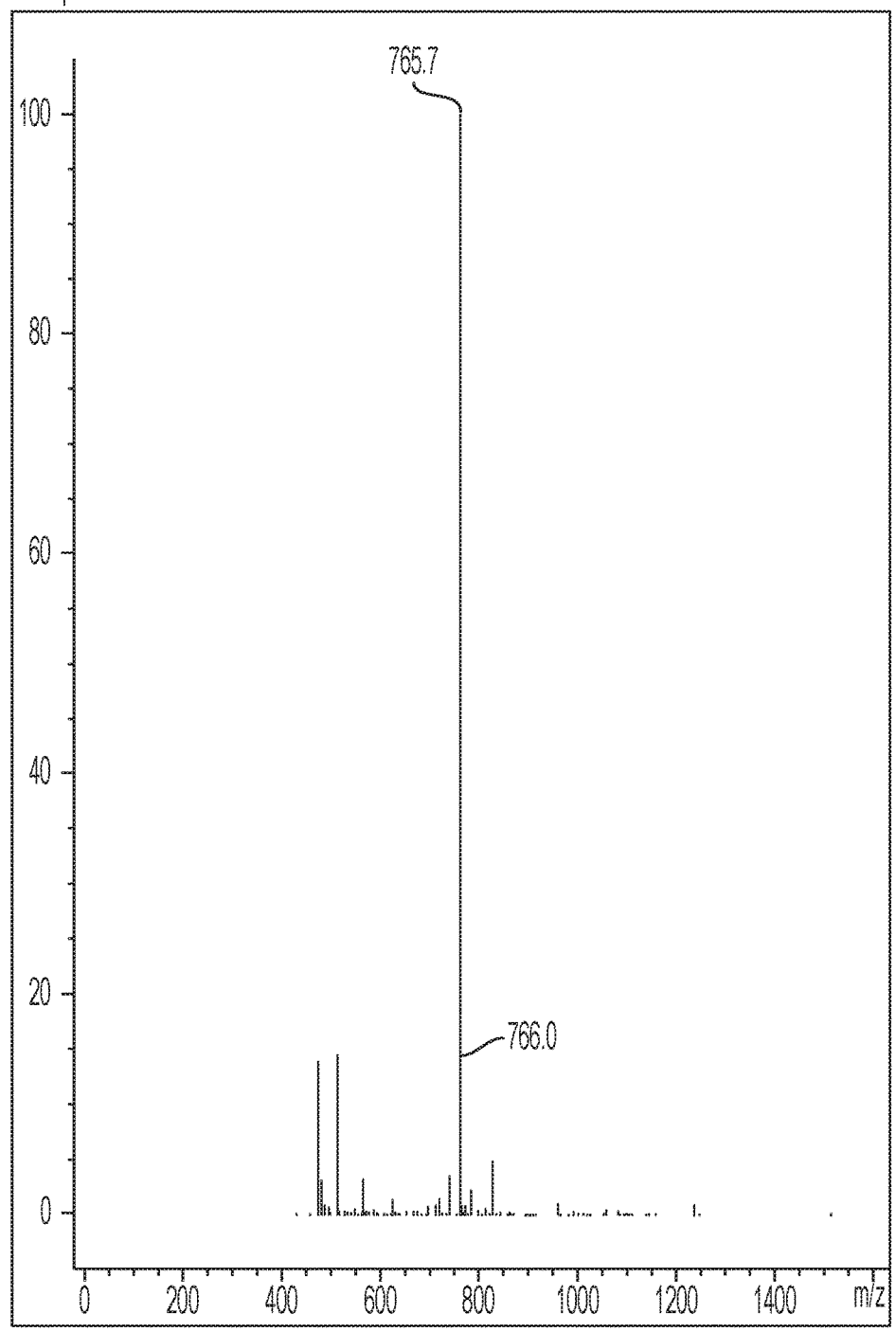

After two nights, the reaction mixture was filtered, concentrated in vacuo, and partitioned between water and dichloromethane. The organic phase was dried and concentrated to give the product. MS spectrum no 25 is shown in FIG. 25, example 24.

LIST OF FIGURES

FIG. 1 MS scan of product 1,2-bis((1-phenyl-2,5,8,11-tetraoxatridecan-13-yl)oxy)benzene obtained from synthesis in example 1

Figure 2:
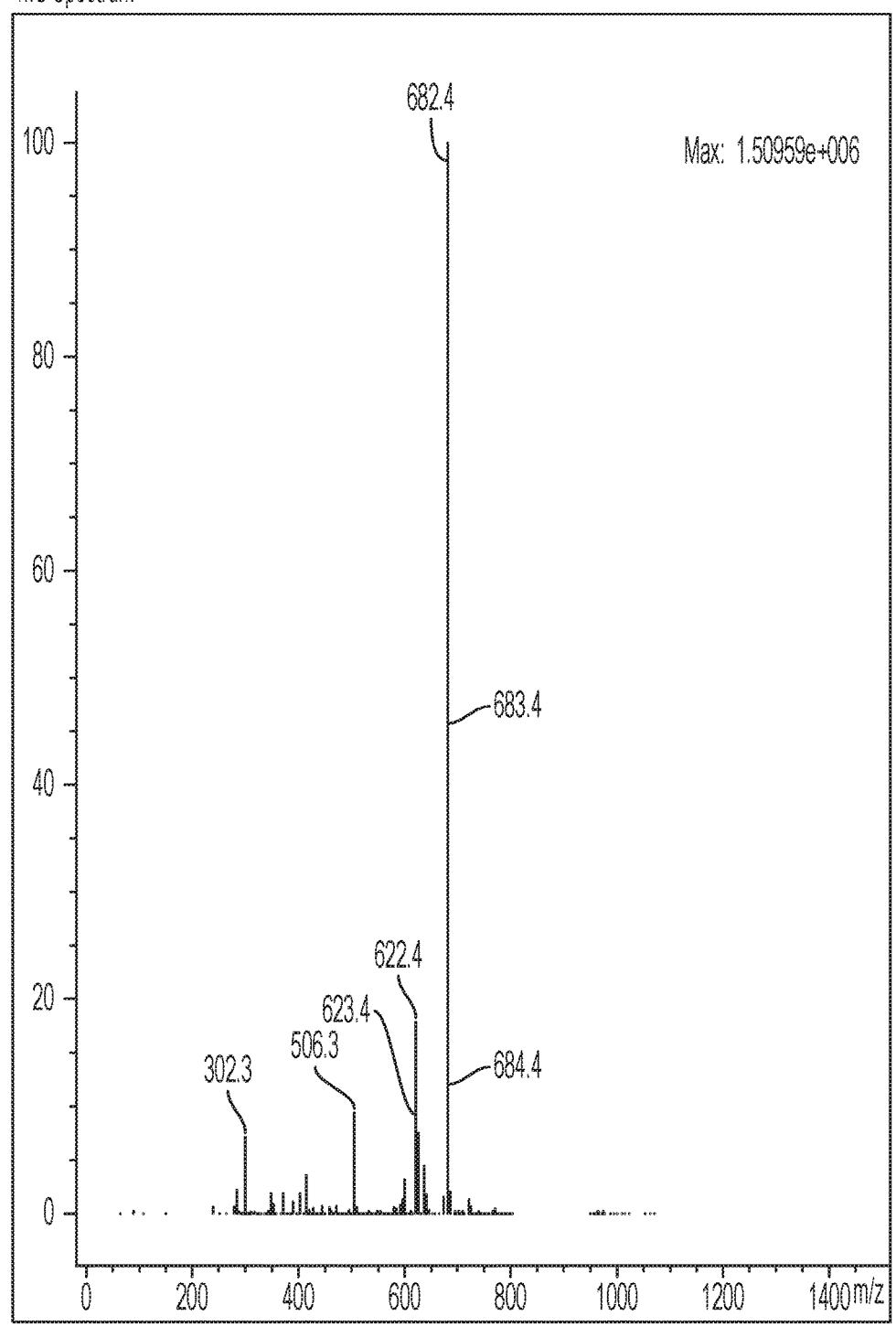

FIG. 2 MS scan of product bis(1-phenyl-2,5,8,11-tetraoxatridecan-13-yl) glutarate obtained from synthesis in example 2

Figure 3:
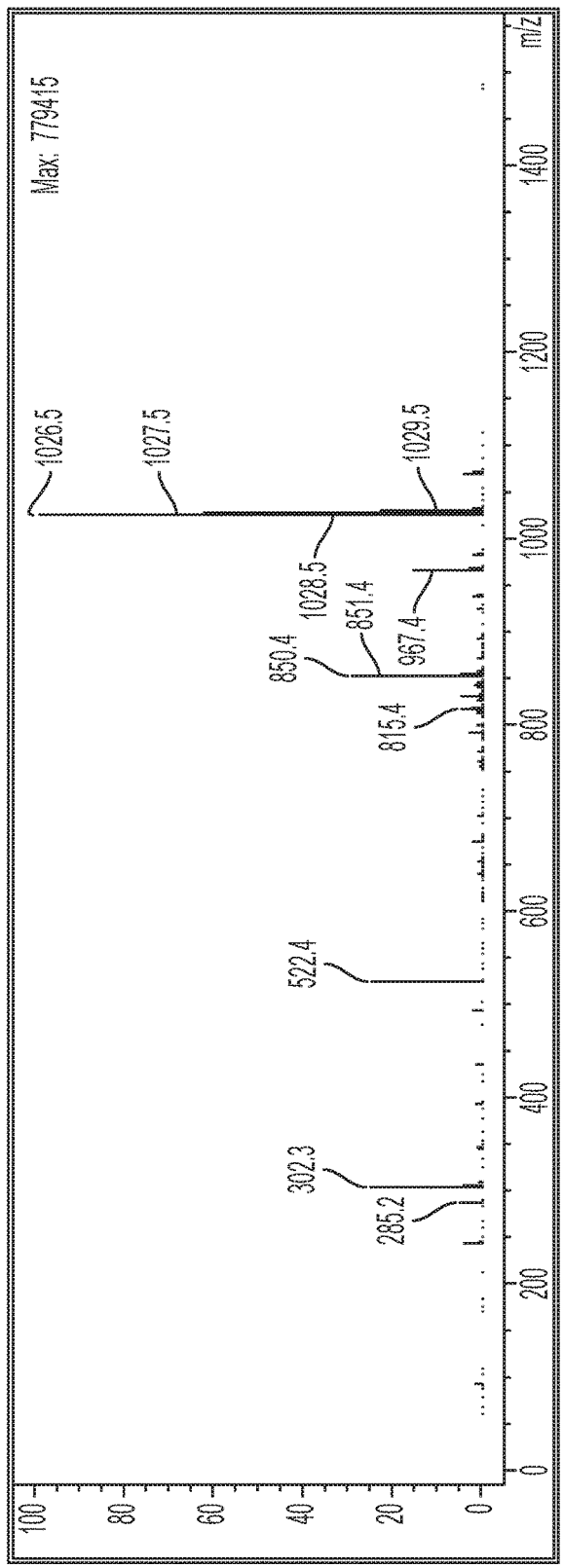

FIG. 3 MS scan of crude product tris(1-phenyl-2,5,8,11-tetraoxatridecan-13-yl) benzene-1,3,5-tricarboxylate obtained from synthesis in example 3

Figure 4:
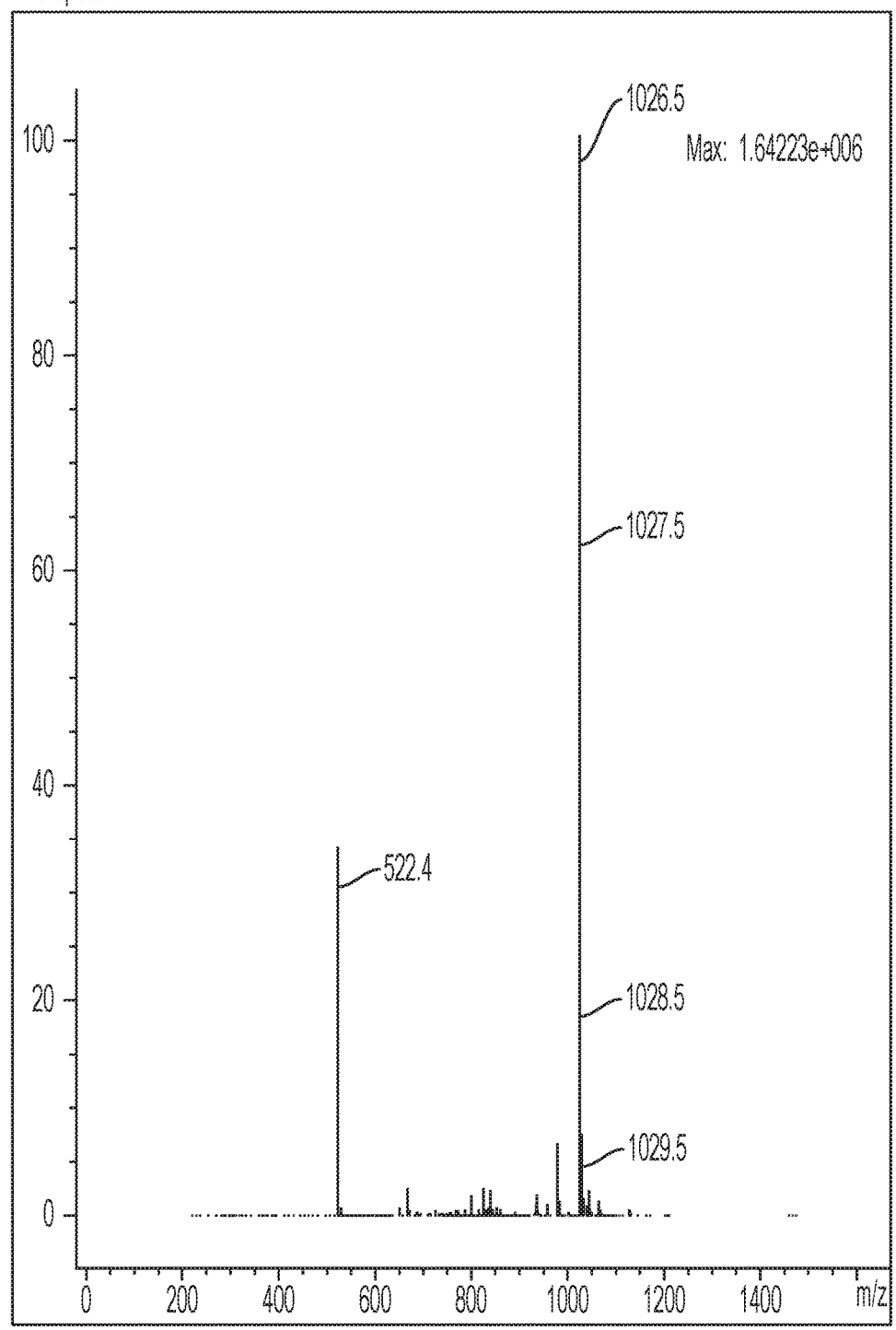

FIG. 4 MS scan of purified product tris(1-phenyl-2,5,8,11-tetraoxatridecan-13-yl) benzene-1,3,5-tricarboxylate obtained from synthesis in example 3

Figure 5:
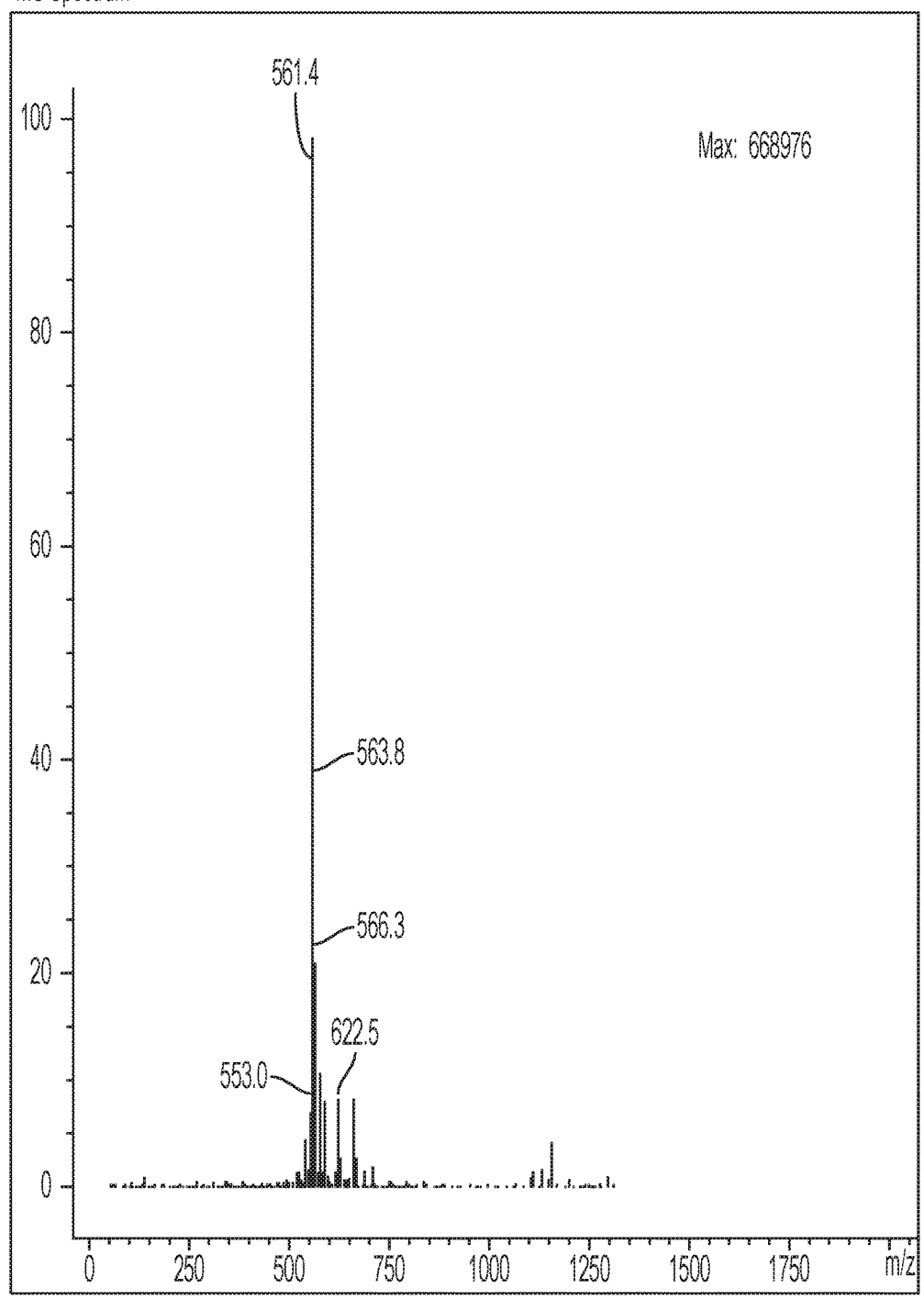

FIG. 5 MS scan of product 1,1'-(1,2-henylenebis(oxy)) bis(3,6,9,12,15,18,21,24-octaoxaoctacosane-28-sulfonic acid) obtained from synthesis in example 4

Figure 6:
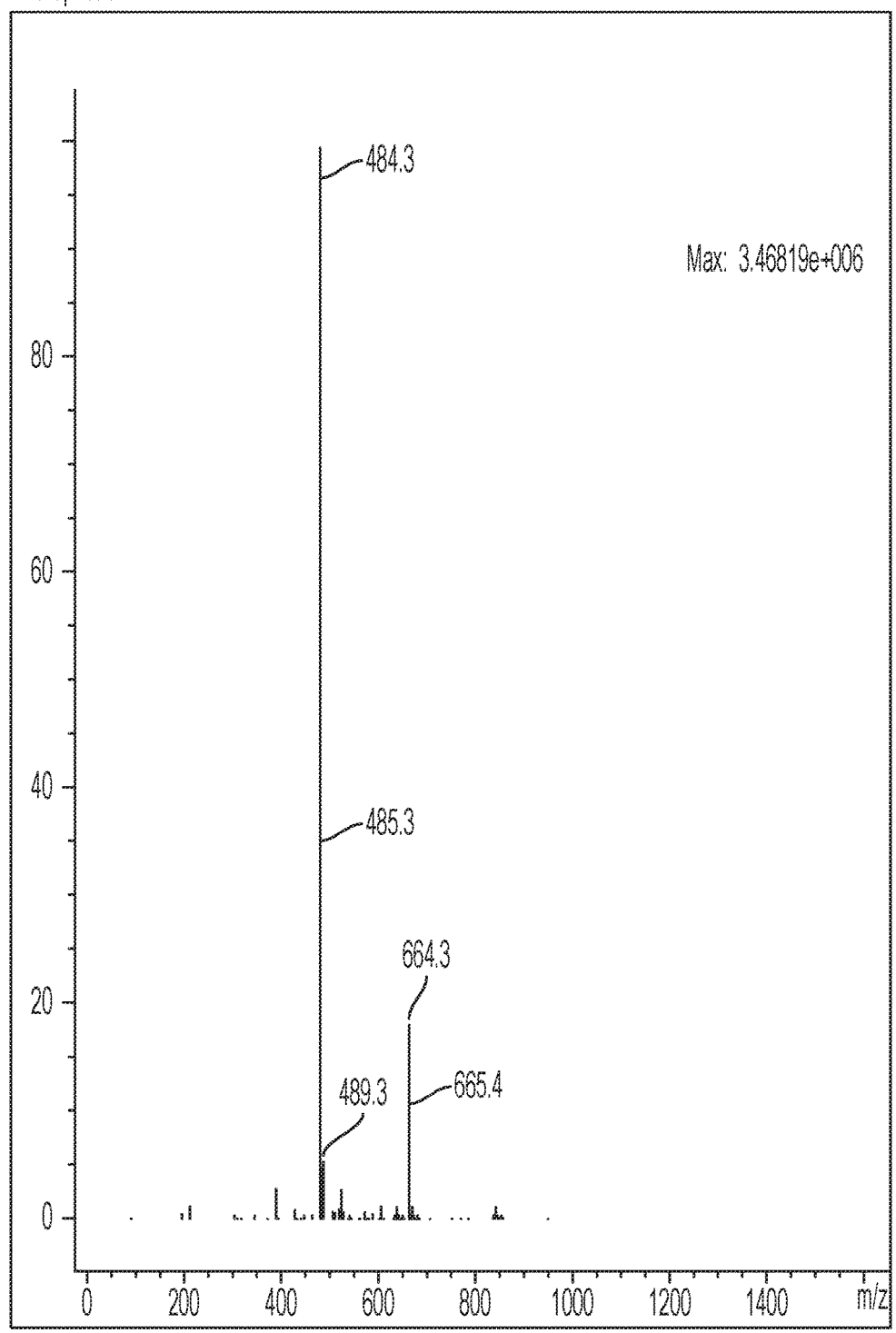

FIG. 6 MS scan of product 1,2-bis(2-(2-(benzyloxy) ethoxy)ethoxy)benzene obtained from synthesis in example 5

Figure 7:
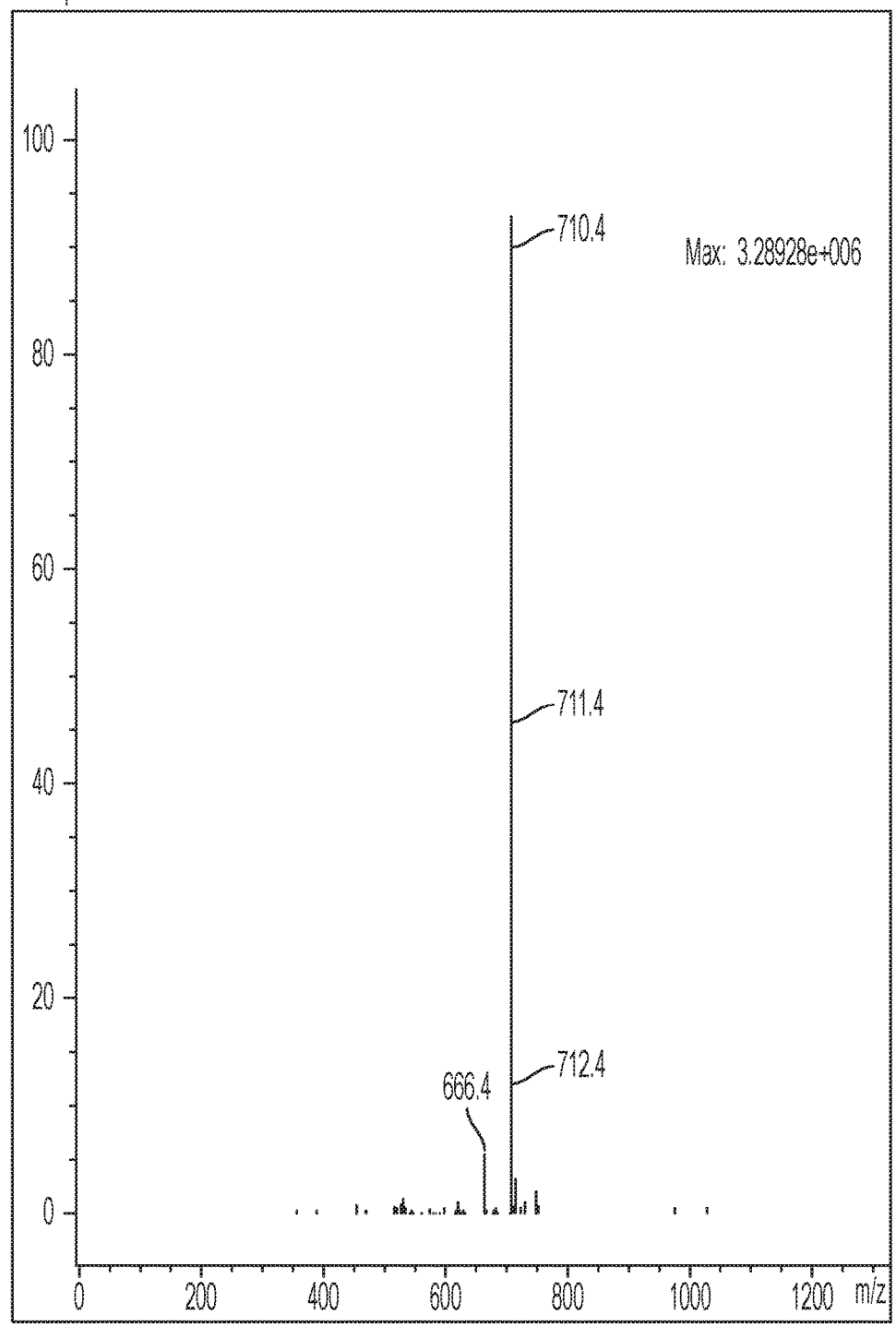

FIG. 7 MS scan of product 2,3-bis((1-phenyl-2,5,8,11-tetraoxatridecan-13-yl)oxy)naphthalene obtained from synthesis in example 6

Figure 8:
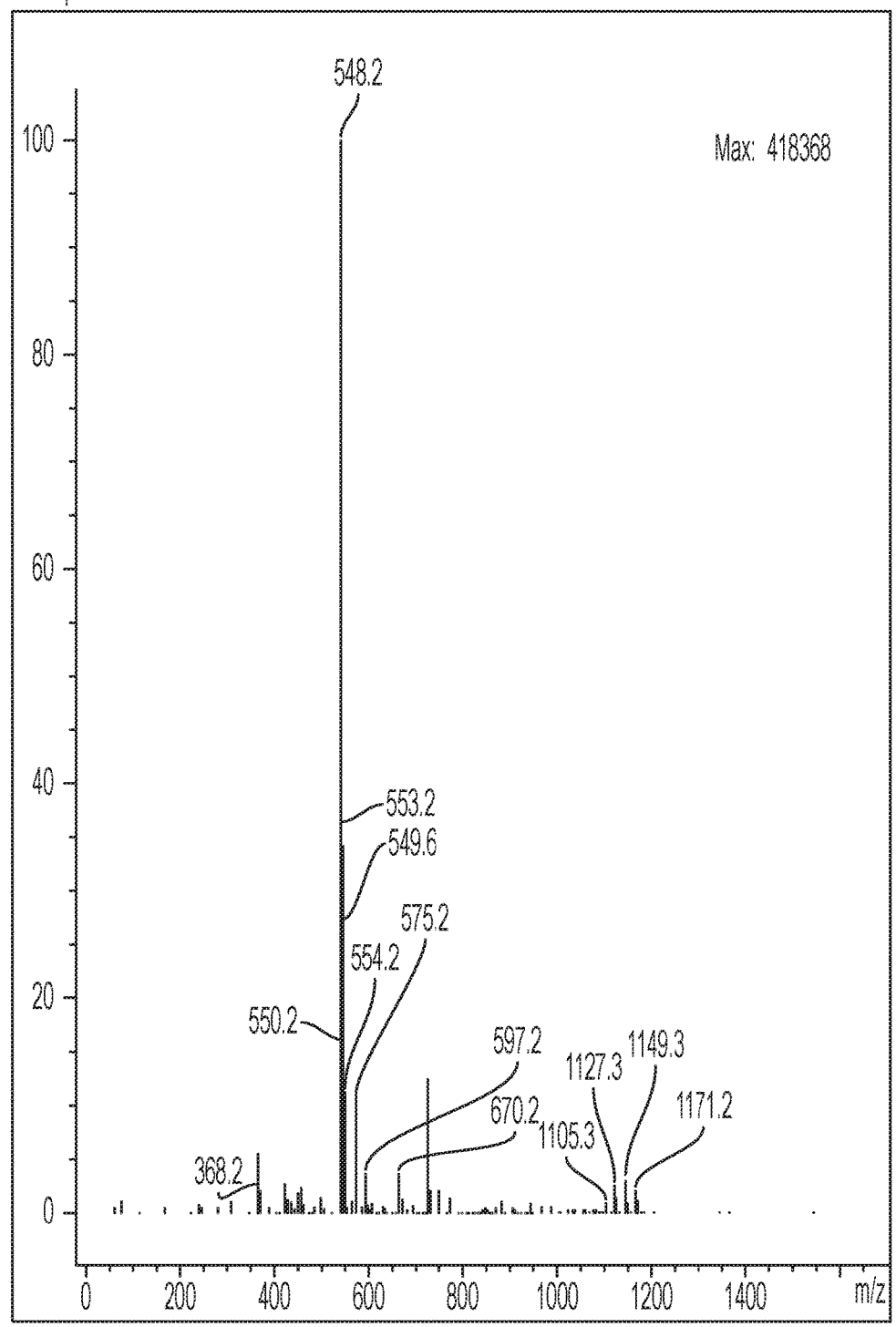

FIG. 8 MS scan of product potassium 3,3'-(((((1,2-phenylenebis(oxy)) bis(ethane-2,1-diyl))bis(oxy))bis(ethane-2,1-diyl))bis(oxy))bis(propane-1-sulfonate) obtained from synthesis in example 7

Figure 9:
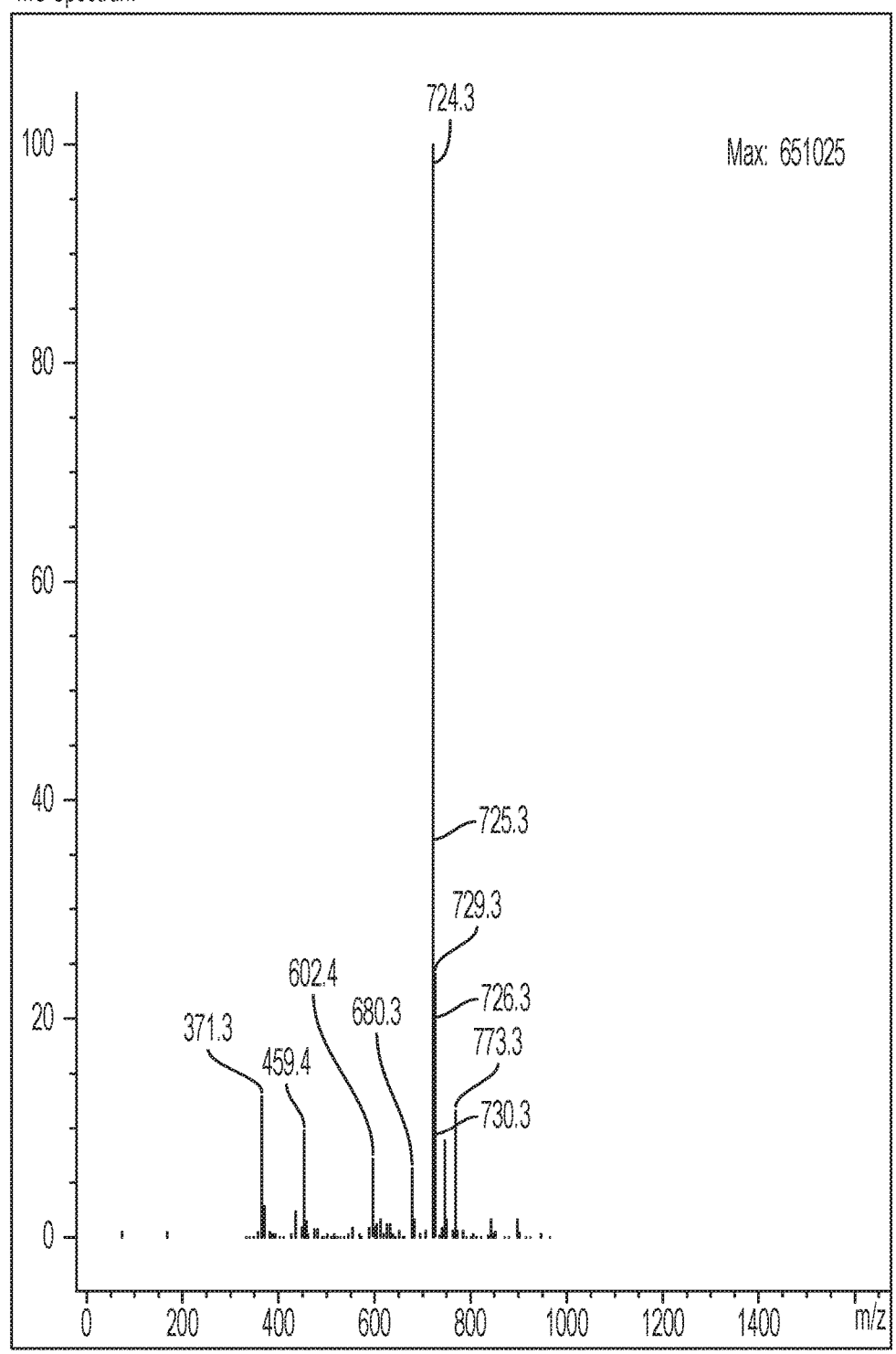

FIG. 9 MS scan of product potassium 1,1'-(1,2-phenylenebis(oxy))bis(3,6,9,12-tetraoxapentadecane-15-sulfonate) obtained from synthesis in example 8

Figure 10:
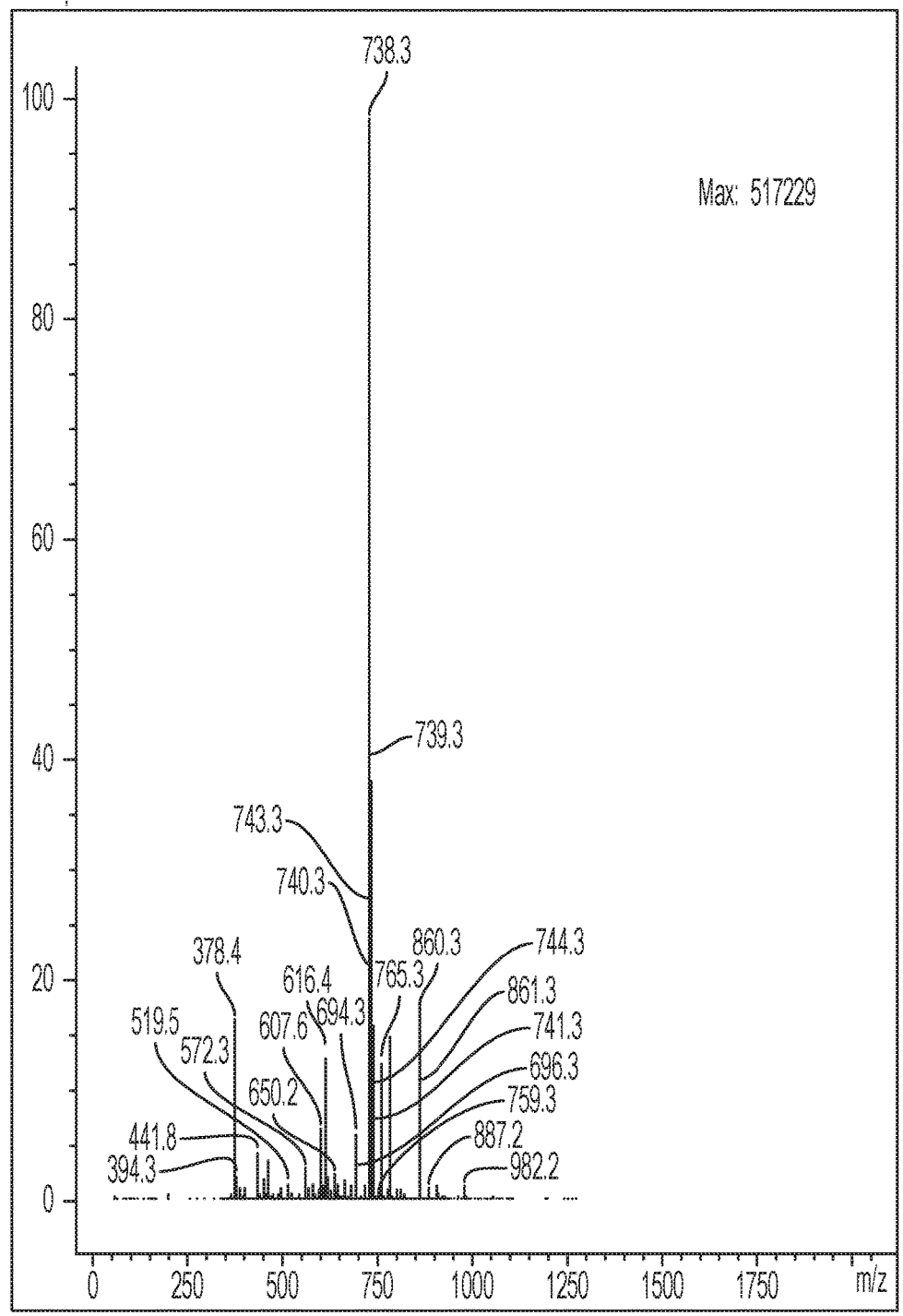

FIG. 10 MS scan of product potassium 1,1'-((4-methyl-1,2-phenylene)bis(oxy))bis(3,6,9,12-tetraoxapentadecane-15-sulfonate) obtained from synthesis in example 9

Figure 11:
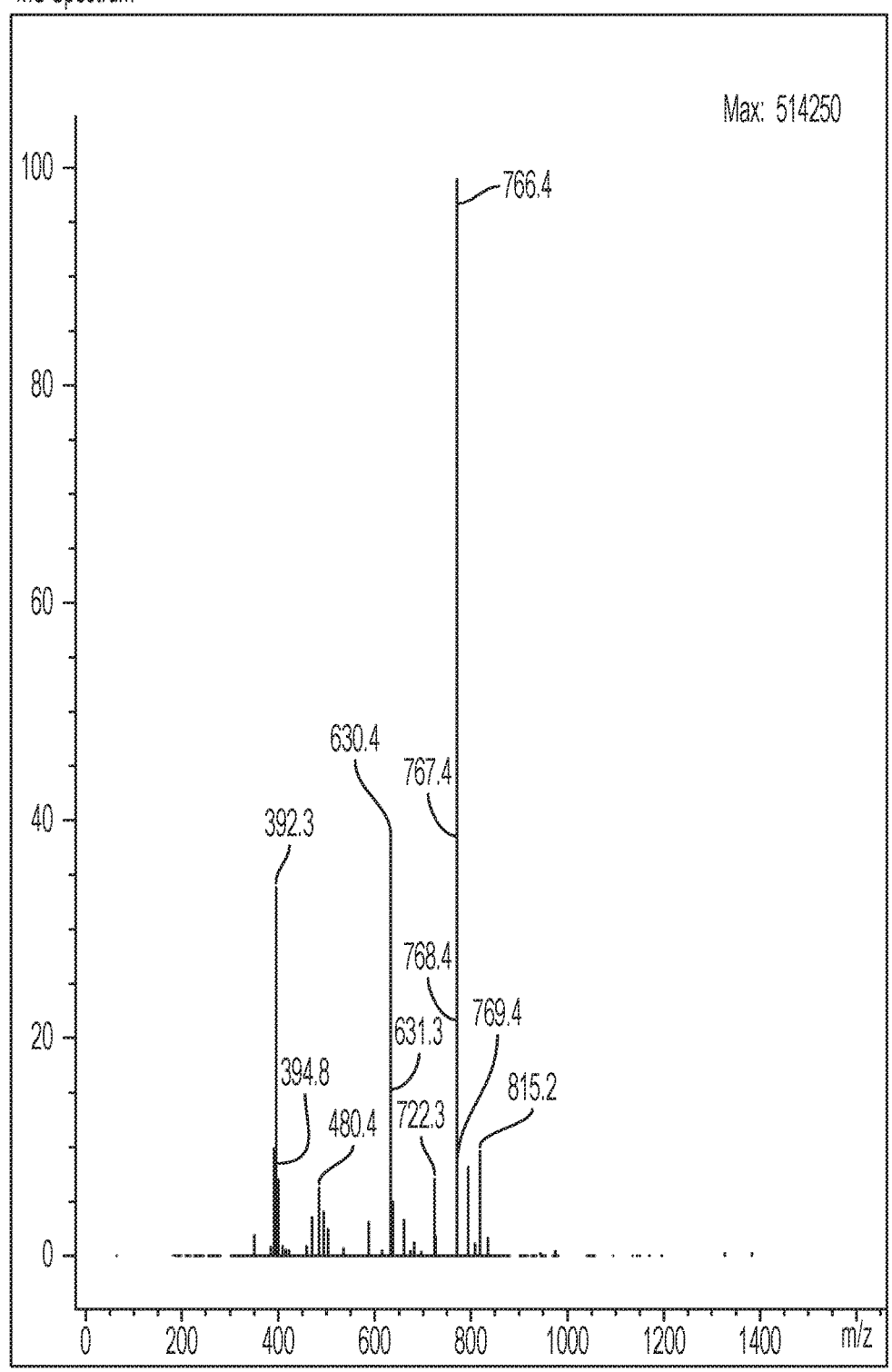

FIG. 11 MS scan of product potassium 1,1'-((4-methyl-1,2-phenylene)bis(oxy))bis(3,6,9,12-tetraoxahexadecane-16-sulfonate) obtained from synthesis in example 10

FIG. 12 MS scan of product 4,4'-((((((4-ethyl-1,3-phenylene)bis(oxy))bis(ethane-2,1-diyl))bis(oxy))bis(ethane-2,1-diyl))bis(oxy))bis(methylene))bis(methylbenzene) obtained from synthesis in example 11

FIG. 13 MS scan of product 13,13'-((4-ethyl-1,3-phenylene)bis(oxy))bis(1-(p-tolyl)-2,5,8,11-tetraoxatridecane) obtained from synthesis in example 12

FIG. 14 MS scan of product 19,19'-((4-ethyl-1,3-phenylene)bis(oxy))bis(1-(p-tolyl)-2,5,8,11,14,17-hexaoxanonadecane) obtained from synthesis in example 13

FIG. 15 MS scan of product 25,25'-((4-ethyl-1,3-phenylene)bis(oxy))bis(1-phenyl-2,5,8,11,14,17,20,23-octaoxapentacosane) obtained from synthesis in example 14

FIG. 16 MS scan of product 13,13'-((4-chloro-1,3-phenylene)bis(oxy))bis(1-(p-tolyl)-2,5,8,11-tetraoxatridecane) obtained from synthesis in example 15

Figure 17:
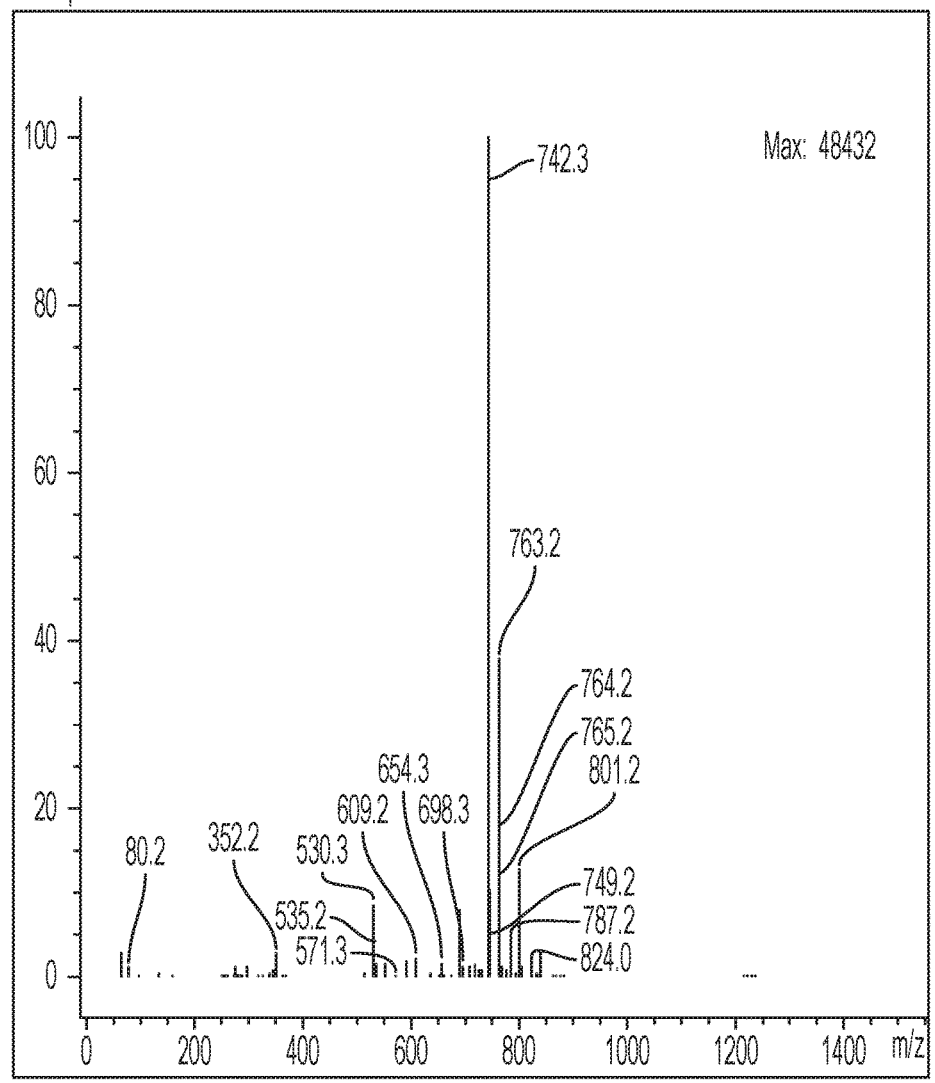

FIG. 17 MS scan of product potassium 4,4'-((((((4-methyl-1,2-phenylene)bis(oxy))bis(ethane-2,1-diyl))bis (oxy))bis(ethane-2,1-diyl))bis(oxy))bis(1-phenylbutane-2-sulfonate) obtained from synthesis in example 16

Figure 18:
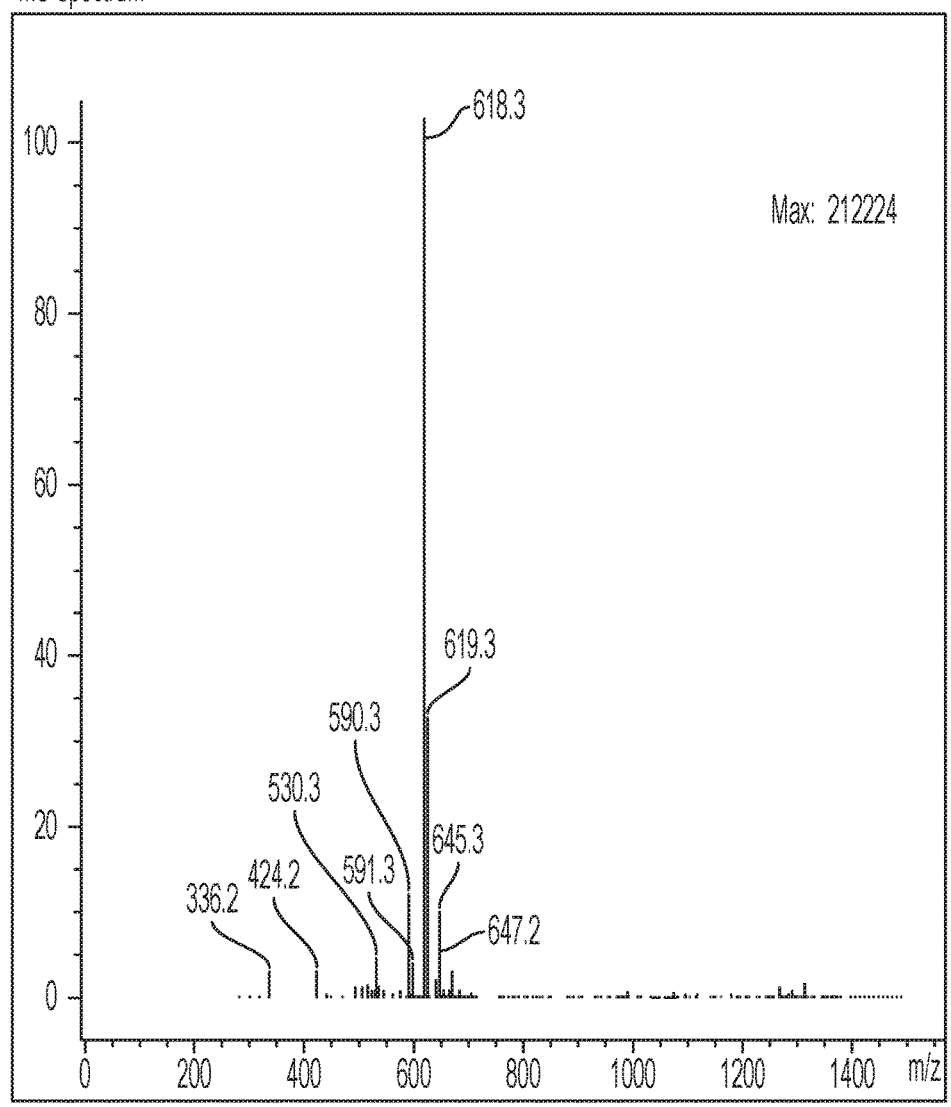

FIG. 18 MS scan of product potassium 1,1'-((((((4-methyl-1,2-phenylene)bis(oxy))bis(ethane-2,1-diyl))bis (oxy))bis(ethane-2,1-diyl))bis(oxy))bis(pentane-3-sulfonate) obtained from synthesis in example 17

FIG. 19 MS scan of product potassium 1,2-bis(15-(4-(tert-butyl)phenyl)-2,5,8,11,14-pentaoxapentadecyl)benzene obtained from synthesis in example 18

FIG. 20 MS scan of product potassium 1,2-bis(15-phenyl-2,5,8,11,14-pentaoxapentadecyl)benzene obtained from synthesis in example 19

FIG. 21 MS scan of product potassium 1,2-bis(27-phenyl-2,5,8,11,14,17,20,23,26-nonaoxaheptacosyl)benzene obtained from synthesis in example 20

FIG. 22 MS scan of product potassium 1,33-bis(4-(tert-butyl)phenyl)-15,19-dimethyl-2,5,8,11,14,17,20,23,26,29, 32-undecaoxatritriacontane obtained from synthesis in example 21

FIG. 23 MS scan of product potassium 1,32-diphenyl-2, 5,8,11,14,19,22,25,28,31-decaoxadotriacontane obtained from synthesis in example 22

FIG. 24 MS scan of product potassium 1,3,5-tris(15-phenyl-2,5,8,11,14-pentaoxapentadecyl)benzene obtained from synthesis in example 23

FIG. 25 MS scan of product potassium 1,3,5-tris(27-phenyl-2,5,8,11,14,17,20,23,26-nonaoxaheptacosyl)benzene obtained from synthesis in example 24

EXAMPLES

The examples given are only illustrations within the scope of the claims and not intended to limit the scope of the invention. The general synthetic schemes are described above. All the MS spectra are run from FAC/AMAC buffers and hence all the masses are represented by the ammonia adduct M+18 (for single ions) and (M+36)/2 for double ions. The MS is regular scans using electrospray ionization and positive mode settings.

Example 1

Synthesis According to Scheme 1 and 2.
MS Spectrum No 1.

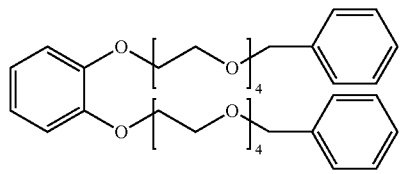

1,2-bis((1-phenyl-2,5,8,11-tetraoxatridecan-13-yl)oxy)benzene

Example 2

Synthesis According to Scheme 5.
MS Spectrum No 2.

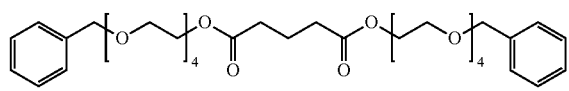

Bis(1-phenyl-2,5,8,11-tetraoxatridecan-13-yl) glutarate

Example 3

Synthesis According to Scheme 5.
MS Spectrum No. 3 of Reaction Mixture and MS Spectrum No. 4 of Purified Product No 4.

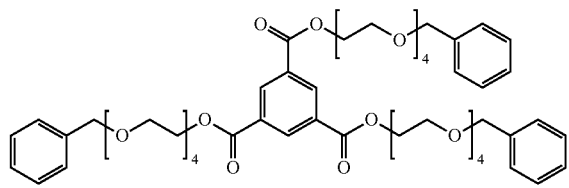

tris(1-phenyl-2,5,8,11-tetraoxatridecan-13-yl) benzene-1,3,5-tricarboxylate

Example 4

Synthesis According to Scheme 1, 2 and 4
MS Spectrum No 5

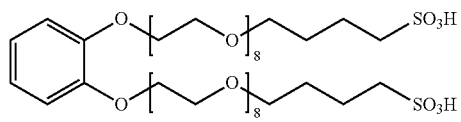

1,1'-(1,2-phenylenebis(oxy))bis(3,6,9,12,15,18,21,24-octaoxaoctacosane-28-sulfonic acid)

Example 5

Synthesis According to Scheme 1 and 2
MS Spectrum No 6

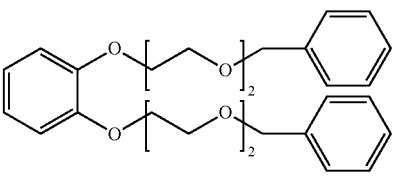

1,2-bis(2-(2-(benzyloxy)ethoxy)ethoxy)benzene

Example 6

Synthesis According to Scheme 1 and 2
MS Spectrum No 7

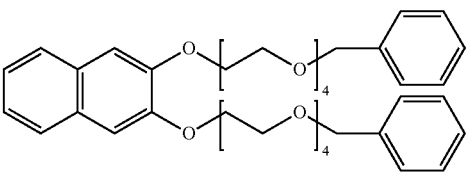

2,3-bis((1-phenyl-2,5,8,11-tetraoxatridecan-13-yl)oxy)naphthalene

Example 7

Synthesis According to Schemes 1, 2 and 4
MS Spectrum No 8

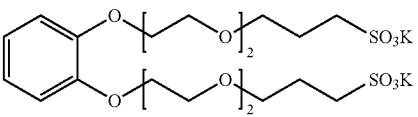

Potassium 3,3'-(((((1,2-phenylenebis(oxy))bis(ethane-2,1-diyl))bis(oxy))bis(ethane-2,1-diyl))bis(oxy))bis(propane-1-sulfonate)

Example 8

Synthesis According to Schemes 1, 2 and 4
MS Spectrum No 9

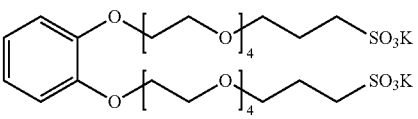

Potassium 1,1'-(1,2-phenylenebis(oxy))bis(3,6,9,12-tetraoxapentadecane-15-sulfonate)

Example 9

Synthesis According to Schemes 1, 2 and 4
MS Spectrum No 10

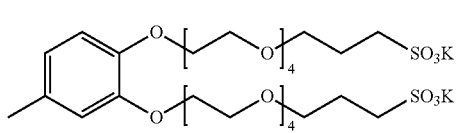

Potassium 1,1'-((4-methyl-1,2-phenylene)bis(oxy))bis(3,6,9,12-tetraoxapentadecane-15-sulfonate)

Example 10

Synthesis According to Schemes 1, 2 and 4
MS Spectrum No 11

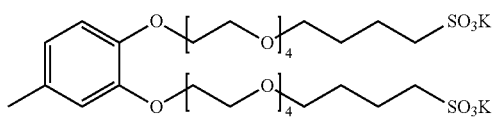

Potassium 1,1'-((4-methyl-1,2-phenylene)bis(oxy))bis(3,6,9,12-tetraoxahexadecane-16-sulfonate)

Example 11

Synthesis According to Schemes 1 and 3
MS Spectrum No 12

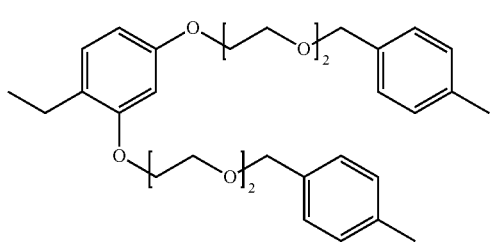

4,4'-(((((((4-ethyl-1,3-phenylene)bis(oxy))bis(ethane-2,1-diyl))bis(oxy))bis(ethane-2,1-diyl))bis(oxy))bis(methylene))bis(methylbenzene)

Example 12

Synthesis According to Schemes 1 and 3
MS Spectrum No 13

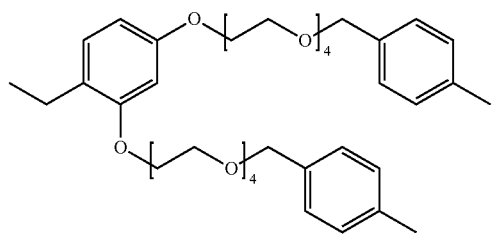

13,13'-((4-ethyl-1,3-phenylene)bis(oxy))bis(1-(p-tolyl)-2,5,8,11-tetraoxatridecane)

Example 13

Synthesis According to Schemes 1 and 3
MS Spectrum No 14

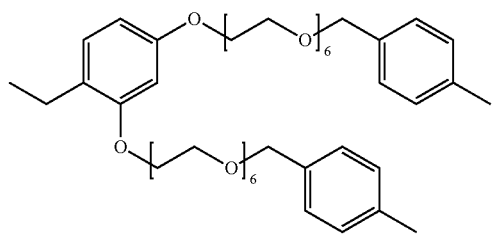

19,19'-((4-ethyl-1,3-phenylene)bis(oxy))bis(1-(p-tolyl)-2,5,8,11,14,17-hexaoxanonadecane)

Example 14

Synthesis According to Schemes 1 and 3
MS Spectrum No 15

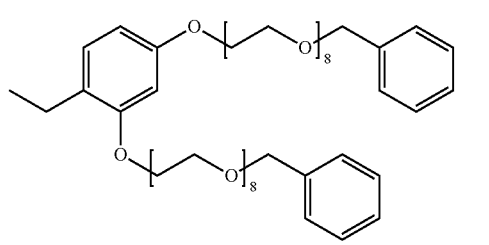

25,25'-((4-ethyl-1,3-phenylene)bis(oxy))bis(1-phenyl-2,5,8,11,14,17,20,23-octaoxapentacosane)

Example 15

Synthesis According to Schemes 1 and 3
MS Spectrum No 16

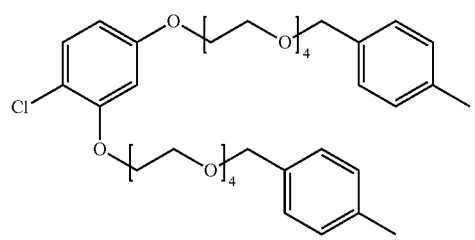

13,13'-((4-chloro-1,3-phenylene)bis(oxy))bis(1-(p-tolyl)-2,5,8,11-tetraoxatridecane)

Example 16

Synthesis According to Schemes 1, 2 and 4
MS Spectrum No 17

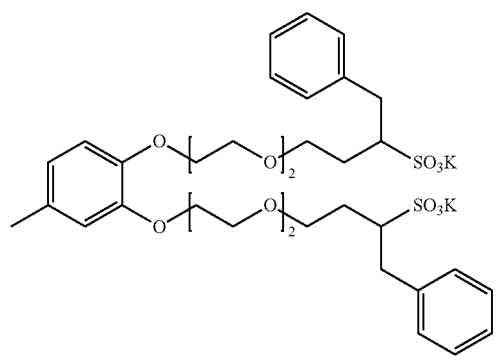

Potassium 4,4'-(((((4-methyl-1,2-phenylene)bis(oxy))bis(ethane-2,1-diyl))bis(oxy))bis(ethane-2,1-diyl))bis(oxy))bis(1-phenylbutane-2-sulfonate)

Example 17

Synthesis According to Schemes 1, 2 and 4
MS Spectrum No 18

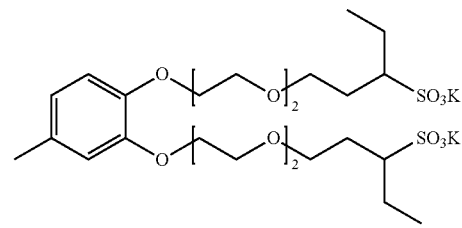

Potassium 1,1'-(((((4-methyl-1,2-phenylene)bis(oxy))bis(ethane-2,1-diyl))bis(oxy))bis(ethane-2,1-diyl))bis(oxy))bis(pentane-3-sulfonate)

Example 18

Synthesis According to Schemes 1 and 7
MS Spectrum No 19

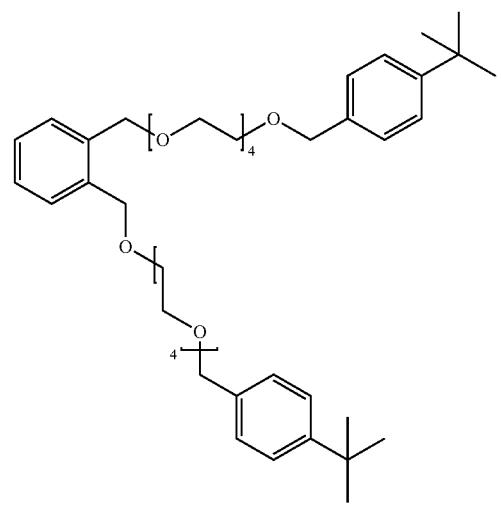

1,2-bis(15-(4-(tert-butyl)phenyl)-2,5,8,11,14-pentaoxapentadecyl)benzene

Example 19

Synthesis According to Schemes 1 and 7
MS Spectrum No 20

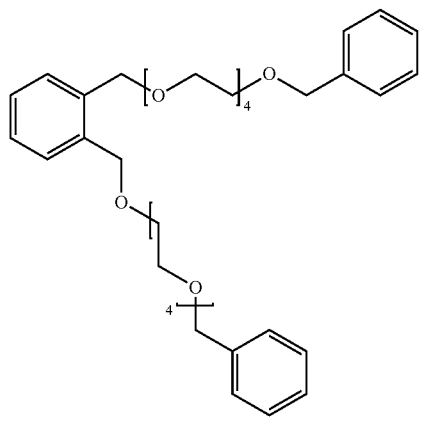

1,2-bis(15-phenyl-2,5,8,11,14-pentaoxapentadecyl)benzene

Example 20

Synthesis According to Schemes 1 and 7
MS Spectrum No 21

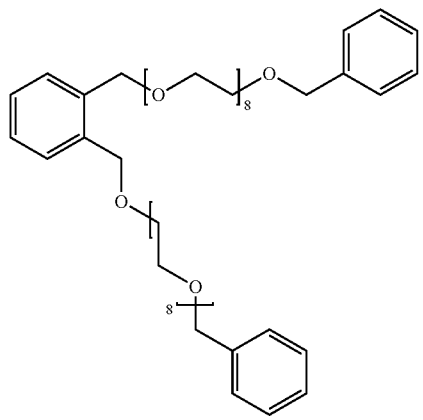

1,2-bis(27-phenyl-2,5,8,11,14,17,20,23,26-nonaoxaheptacosyl)benzene

Example 21

Synthesis According to Schemes 1 and 6
MS Spectrum No 22

1,33-bis(4-(tert-butyl)phenyl)-15,19-dimethyl-2,5,8,11,14,17,20,23,26,29,32-undecaoxatritriacontane

Example 22

Synthesis According to Schemes 1 and 8
MS Spectrum No 23

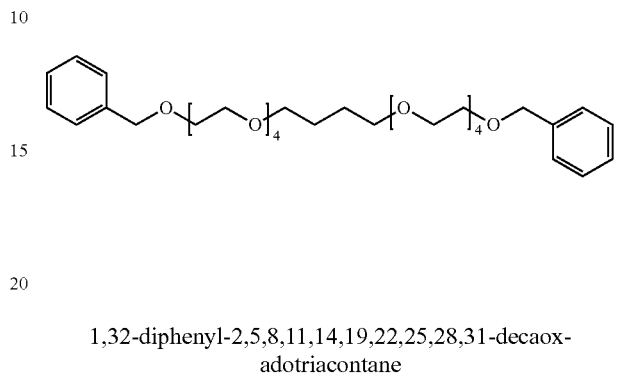

1,32-diphenyl-2,5,8,11,14,19,22,25,28,31-decaoxadotriacontane

Example 23

Synthesis According to Schemes 1 and 9
MS Spectrum No 24

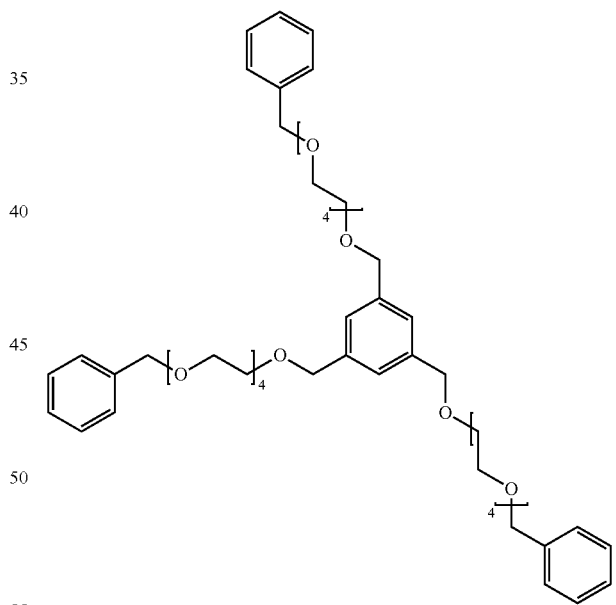

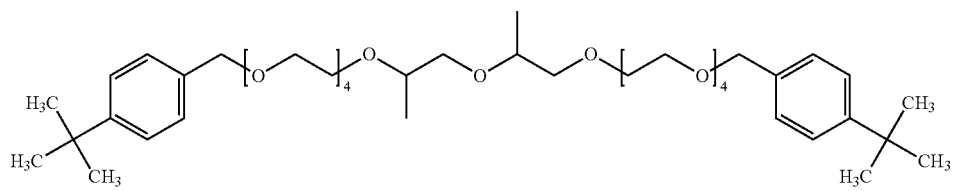

1,3,5-tris(15-phenyl-2,5,8,11,14-pentaoxapentade-cyl)benzene

Example 24

Synthesis According to Schemes 1 and 9
MS Spectrum No 25

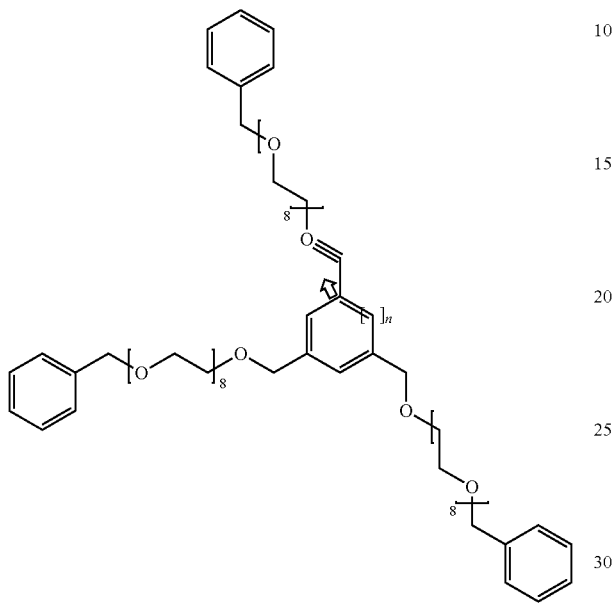

1,3,5-tris(27-phenyl-2,5,8,11,14,17,20,23,26-non-aoxaheptacosyl)benzene

The table below is an overview of synthesized compounds and their main mass peak(s) $(m+n*18/n*z)$, where n=number of ion charges, as a $NH_4$-M adducts. The observed molecular adducts are used for product identifications in LC-MS analysis. The 24 examples above can be found in the table with reference in the third column and the fourth column refers to the synthetic methods used and described earlier in scheme 1-9.

| | Chemical name | Ex. No. | Scheme no. | m/z. as $NH_4$ adduct |
|---|---|---|---|---|
| 1 | 1,2-bis(2-(2-(benzyloxy)ethoxy)ethoxy)benzene | 5 | 1.2 | 484.3 |
| 2 | 1,2-bis(2-(2-(2-(benzyloxy)ethoxy)ethoxy)ethoxy)benzene | | 1.2 | 572.3 |
| 3 | 1,2-bis((1-phenyl-2,5,8,11-tetraoxatridecan-13-yl)oxy)benzene | 1 | 1.2 | 660.4 |
| 4 | 1,2-bis((1-phenyl-2,5,8,11,14-pentaoxahexadecan-16-yl)oxy)benzene | | 1.2 | 748.5 |
| 5 | 1,2-bis((1-phenyl-2,5,8,11,14,17-hexaoxanonadecan-19-yl)oxy)benzene | | 1.2 | 836.5 |
| 6 | 1,2-bis((1-phenyl-2,5,8,11,14,17,20,23-octaoxapentacosan-25-yl)oxy)benzene | | 1.2 | 1012.6/ 515.4 |
| 7 | 1,2-bis(2-(2-((4-methylbenzyl)oxy)ethoxy)ethoxy)benzene | | 1.2 | 512.4 |
| 8 | 1,2-bis(2-(2-(2-((4-methylbenzyl)oxy)ethoxy)ethoxy)ethoxy)benzene | | 1.2 | 600.4 |
| 9 | 1,2-bis((1-(p-tolyl)-2,5,8,11-tetraoxatridecan-13-yl)oxy)benzene | | 1.2 | 688.5 |
| 10 | 1,2-bis((1-(p-tolyl)-2,5,8,11,14-pentaoxahexadecan-16-yl)oxy)benzene | | 1.2 | 776.4 |
| 11 | 1,2-bis((1-(p-tolyl)-2,5,8,11,14,17-hexaoxanonadecan-19-yl)oxy)benzene | | 1.2 | 864.5 |
| 12 | 1,2-bis((1-(4-(tert-butyl)phenyl)-2,5,8,11-tetraoxatridecan-13-yl)oxy)benzene | | 1.2 | 772.5 |

-continued

| | Chemical name | Ex. No. | Scheme no. | m/z. as NH$_4$ adduct |
|---|---|---|---|---|
| 13 | 1,2-bis((1-(4-(tert-butyl)phenyl)-2,5,8,11,14,17,20,23-octaoxapentacosan-25-yl)oxy)benzene | | 1.2 | 1124.7/ 571.5 |
| 14 | 1,2-bis(2-(2-(naphthalen-2-ylmethoxy)ethoxy)ethoxy)benzene | | 1.2 | 584.4 |
| 15 | 1,2-bis((1-(naphthalen-2-yl)-2,5,8,11,14,17-hexaoxanonadecan-19-yl)oxy)benzene | | 1.2 | 936.4 |
| 16 | 1,3-bis((1-phenyl-2,5,8,11-tetraoxatridecan-13-yl)oxy)benzene | | 1.3 | 660.4 |
| 17 | 1,4-bis((1-phenyl-2,5,8,11-tetraoxatridecan-13-yl)oxy)benzene | | 1.3 | 660.4 |
| 18 | (((((((4-methyl-1,2-phenylene)bis(oxy))bis(ethane-2,1-diyl))bis(oxy))bis(ethane-2,1-diyl))bis(oxy))bis(methylene))dibenzene | | 1.2 | 498.4 |
| 19 | (((((((((4-methyl-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))dibenzene | | 1.2 | 586.3 |
| 20 | 13,13'-((4-methyl-1,2-phenylene)bis(oxy))bis(1-phenyl-2,5,8,11-tetraoxatridecane) | | 1.2 | 674.5 |
| 21 | 16,16'-((4-methyl-1,2-phenylene)bis(oxy))bis(1-phenyl-2,5,8,11,14-pentaoxahexadecane) | | 1.2 | 762.5 |
| 22 | 19,19'-((4-methyl-1,2-phenylene)bis(oxy))bis(1-phenyl-2,5,8,11,14,17-hexaoxanonadecane) | | 1.2 | 850.6 |
| 23 | 25,25'-((4-methyl-1,2-phenylene)bis(oxy))bis(1-phenyl-2,5,8,11,14,17,20,23-octaoxapentacosane) | | 1.2 | 1026.5/ 522.4 |
| 24 | 4,4'-(((((((4-methyl-1,2-phenylene)bis(oxy))bis(ethane-2,1-diyl))bis(oxy))bis(ethane-2,1-diyl))bis(oxy))bis(methylene))bis(methylbenzene) | | 1.2 | 526.4 |
| 25 | 4,4'-(((((((((4-methyl-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))bis(methylbenzene) | | 1.2 | 614.4 |
| 26 | 13,13'-((4-methyl-1,2-phenylene)bis(oxy))bis(1-(p-tolyl)-2,5,8,11-tetraoxatridecane) | | 1.2 | 702.5 |
| 27 | 16,16'-((4-methyl-1,2-phenylene)bis(oxy))bis(1-(p-tolyl)-2,5,8,11,14-pentaoxahexadecane) | | 1.2 | 790.5 |
| 28 | 19,19'-((4-methyl-1,2-phenylene)bis(oxy))bis(1-(p-tolyl)-2,5,8,11,14,17-hexaoxanonadecane) | | 1.2 | 878.6 |
| 29 | 4,4'-(((((((4-ethyl-1,3-phenylene)bis(oxy))bis(ethane-2,1-diyl))bis(oxy))bis(ethane-2,1-diyl))bis(oxy))bis(methylene))bis(methylbenzene) | 11 | 1.3 | 540.5 |
| 30 | 13,13'-((4-ethyl-1,3-phenylene)bis(oxy))bis(1-(p-tolyl)-2,5,8,11-tetraoxatridecane) | 12 | 1.3 | 716.4 |
| 31 | 19,19'-((4-ethyl-1,3-phenylene)bis(oxy))bis(1-(p-tolyl)-2,5,8,11,14,17-hexaoxanonadecane) | 13 | 1.3 | 892.5/ 455.4 |
| 32 | (((((((4-(tert-butyl)-1,2-phenylene)bis(oxy))bis(ethane-2,1-diyl))bis(oxy))bis(ethane-2,1-diyl))bis(oxy))bis(methylene))dibenzene | | 1.2 | 540.3 |
| 33 | (((((((((4-(tert-butyl)-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))dibenzene | | 1.2 | 628.5 |
| 34 | 13,13'-((4-(tert-butyl)-1,2-phenylene)bis(oxy))bis(1-phenyl-2,5,8,11-tetraoxatridecane) | | 1.2 | 416.5 |
| 35 | 16,16'-((4-(tert-butyl)-1,2-phenylene)bis(oxy))bis(1-phenyl-2,5,8,11,14-pentaoxahexadecane) | | 1.2 | 804.5 |
| 36 | 19,19'-((4-(tert-butyl)-1,2-phenylene)bis(oxy))bis(1-phenyl-2,5,8,11,14,17-hexaoxanonadecane) | | 1.2 | 892.6 |
| 37 | 25,25'-((4-(tert-butyl)-1,2-phenylene)bis(oxy))bis(1-phenyl-2,5,8,11,14,17,20,23-octaoxapentacosane) | | 1.2 | 1068.5/ 543.5 |
| 38 | 4,4'-(((((((4-(tert-butyl)-1,2-phenylene)bis(oxy))bis(ethane-2,1-diyl))bis(oxy))bis(ethane-2,1-diyl))bis(oxy))bis(methylene))bis(methylbenzene) | | 1.2 | 568.4 |
| 39 | 4,4'-(((((((((4-(tert-butyl)-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))bis(methylbenzene) | | 1.2 | 656.6 |
| 40 | 13,13'-((4-(tert-butyl)-1,2-phenylene)bis(oxy))bis(1-(p-tolyl)-2,5,8,11-tetraoxatridecane) | | 1.2 | 744.5 |
| 41 | 16,16'-((4-(tert-butyl)-1,2-phenylene)bis(oxy))bis(1-(p-tolyl)-2,5,8,11,14-pentaoxahexadecane) | | 1.2 | 832.5 |
| 42 | 19,19'-((4-(tert-butyl)-1,2-phenylene)bis(oxy))bis(1-(p-tolyl)-2,5,8,11,14,17-hexaoxanonadecane) | | 1.2 | 920.6 |
| 43 | 25,25'-((4-(tert-butyl)-1,2-phenylene)bis(oxy))bis(1-(4-(tert-butyl)phenyl)-2,5,8,11,14,17,20,23-octaoxapentacosane) | | 1.2 | 1180.8/ 599.5 |
| 44 | 19,19'-((4-(tert-butyl)-1,2-phenylene)bis(oxy))bis(1-(naphthalen-2-yl)-2,5,8,11,14,17-hexaoxanonadecane) | | 1.2 | 992.5 |

-continued

| | Chemical name | Ex. No. | Scheme no. | m/z. as NH₄ adduct |
|---|---|---|---|---|
| 45 | (((((((3,5-di-tert-butyl-1,2-phenylene)bis(oxy))bis(ethane-2,1-diyl))bis(oxy))bis(ethane-2,1-diyl))bis(oxy))bis(methylene))dibenzene | | 1.2 | 596.5 |
| 46 | 13,13'-((3,5-di-tert-butyl-1,2-phenylene)bis(oxy))bis(1-phenyl-2,5,8,11-tetraoxatridecane) | | 1.2 | 772.6 |
| 47 | 19,19'-((3,5-di-tert-butyl-1,2-phenylene)bis(oxy))bis(1-phenyl-2,5,8,11,14,17-hexaoxanonadecane) | | 1.2 | 948.6 |
| 48 | 25,25'-((3,5-di-tert-butyl-1,2-phenylene)bis(oxy))bis(1-phenyl-2,5,8,11,14,17,20,23-octaoxapentacosane) | | 1.2 | 1124.7/ 571.5 |
| 49 | 13,13'-((3,5-di-tert-butyl-1,2-phenylene)bis(oxy))bis(1-(4-(tert-butyl)phenyl)-2,5,8,11-tetraoxatridecane) | | 1.2 | 884.6 |
| 50 | 25,25'-((3,5-di-tert-butyl-1,2-phenylene)bis(oxy))bis(1-(4-(tert-butyl)phenyl)-2,5,8,11,14,17,20,23-octaoxapentacosane) | | 1.2 | 1236.8/ 627.5 |
| 51 | 1,2-bis(15-phenyl-2,5,8,11,14-pentaoxapentadecyl)benzene | | 1.7 | 688.2 |
| 52 | 1,2-bis(27-phenyl-2,5,8,11,14,17,20,23,26-nonaoxaheptacosyl)benzene | | 1.7 | 1040.6 |
| 53 | 1,2-bis(15-(4-(tert-butyl)phenyl)-2,5,8,11,14-pentaoxapentadecyl)benzene | 18 | 1.7 | 800.5 |
| 54 | 4,4'-(((((((4-chloro-1,3-phenylene)bis(oxy))bis(ethane-2,1-diyl))bis(oxy))bis(ethane-2,1-diyl))bis(oxy))bis(methylene))bis(methylbenzene) | | 1.3 | 546.2 |
| 55 | 13,13'-((4-chloro-1,3-phenylene)bis(oxy))bis(1-(p-tolyl)-2,5,8,11-tetraoxatridecane) | 15 | 1.3 | 722.4 |
| 56 | 1,5-bis((1-phenyl-2,5,8,11-tetraoxatridecan-13-yl)oxy)naphthalene | | 1.2 | 710.4 |
| 57 | 2,3-bis(2-(2-(benzyloxy)ethoxy)ethoxy)naphthalene | | 1.2 | 534.3 |
| 58 | 2,3-bis(2-(2-(2-(benzyloxy)ethoxy)ethoxy)ethoxy)naphthalene | | 1.2 | 622.5 |
| 59 | 2,3-bis((1-phenyl-2,5,8,11-tetraoxatridecan-13-yl)oxy)naphthalene | 6 | 1.2 | 710.4 |
| 60 | 2,3-bis((1-phenyl-2,5,8,11,14-pentaoxahexadecan-16-yl)oxy)naphthalene | | 1.2 | 798.4 |
| 61 | 2,3-bis((1-phenyl-2,5,8,11,14,17-hexaoxanonadecan-19-yl)oxy)naphthalene | | 1.2 | 886.4 |
| 62 | 2,3-bis((1-phenyl-2,5,8,11,14,17,20,23-octaoxapentacosan-25-yl)oxy)naphthalene | | 1.2 | 1062.5/ 540.4 |
| 63 | 2,3-bis(2-(2-((4-methylbenzyl)oxy)ethoxy)ethoxy)naphthalene | | 1.2 | 562.4 |
| 64 | 2,3-bis(2-(2-(2-((4-methylbenzyl)oxy)ethoxy)ethoxy)ethoxy)naphthalene | | 1.2 | 650.4 |
| 65 | 2,3-bis((1-(p-tolyl)-2,5,8,11-tetraoxatridecan-13-yl)oxy)naphthalene | | 1.2 | 738.4 |
| 66 | 2,3-bis((1-(p-tolyl)-2,5,8,11,14-pentaoxahexadecan-16-yl)oxy)naphthalene | | 1.2 | 826.4 |
| 67 | 2,3-bis((1-(p-tolyl)-2,5,8,11,14,17-hexaoxanonadecan-19-yl)oxy)naphthalene | | 1.2 | 914.6 |
| 68 | 13,13'-((propane-2,2-diylbis(4,1-phenylene))bis(oxy))bis(1-(p-tolyl)-2,5,8,11-tetraoxatridecane) | | 1.2 | 806.4 |
| 69 | 19,19'-((propane-2,2-diylbis(4,1-phenylene))bis(oxy))bis(1-(p-tolyl)-2,5,8,11,14,17-hexaoxanonadecane) | | 1.2 | 982.5/ 500.5 |
| 70 | 1,33-bis(4-(tert-butyl)phenyl)-15,19-dimethyl-2,5,8,11,14,17,20,23,26,29,32-undecaoxatritriacontane | 21 | 1.6 | 796.6 |
| 71 | 1,32-diphenyl-2,5,8,11,14,19,22,25,28,31-decaoxadotriacontane | 22 | 1.8 | 640.5 |
| 72 | 1,56-diphenyl-2,5,8,11,14,17,20,23,26,31,34,37,40,43,46,49,52,55-octadecaoxahexapentacontane | | 1.8 | 992.6 |
| 73 | bis(1-phenyl-2,5,8,11-tetraoxatridecan-13-yl) succinate | | 5 | 668.4 |
| 74 | bis(1-(4-(tert-butyl)phenyl)-2,5,8,11-tetraoxatridecan-13-yl) succinate | | 5 | 780.5 |
| 75 | bis(1-(4-(tert-butyl)phenyl)-2,5,8,11,14,17,20,23-octaoxapentacosan-25-yl) succinate | | 5 | 1132.6/ 575.5 |
| 76 | bis(1-phenyl-2,5,8,11-tetraoxatridecan-13-yl) glutarate | 2 | 5 | 682.4 |
| 77 | bis(1-phenyl-2,5,8,11,14,17,20,23-octaoxapentacosan-25-yl) glutarate | | 5 | 1034.5/ 526.4 |
| 78 | bis(1-(4-(tert-butyl)phenyl)-2,5,8,11-tetraoxatridecan-13-yl) glutarate | | 5 | 794.5 |
| 79 | bis(1-phenyl-2,5,8,11-tetraoxatridecan-13-yl) adipate | | 5 | 696.4 |
| 80 | 1,3,5-tris((1-(4-(tert-butyl)phenyl)-2,5,8,11-tetraoxatridecan-13-yl)oxy)benzene | | 1.2 | 1110.7 |
| 81 | 1,3,5-tris(15-phenyl-2,5,8,11,14-pentaoxapentadecyl)benzene | 24 | 1.9 | 984.5 |

-continued

| | Chemical name | Ex. No. | Scheme no. | m/z. as $NH_4$ adduct |
|---|---|---|---|---|
| 82 | 1,3,5-tris(27-phenyl-2,5,8,11,14,17,20,23,26-nonaoxaheptacosyl)benzene | 25 | 1.9 | 765.6 |
| 83 | tris(1-phenyl-2,5,8,11-tetraoxatridecan-13-yl) benzene-1,3,5-tricarboxylate | 3 | 5 | 1026.4 |
| 84 | potassium 3,3'-((((((1,2-phenylenebis(oxy))bis(ethane-2,1-diyl))bis(oxy))bis(ethane-2,1-diyl))bis(oxy))bis(propane-1-sulfonate) | 7 | 1.2.4 | 548.2 |
| 85 | potassium 3,3'-(((((((1,2-phenylenebis(oxy))bis(ethane-2,1-diyl))bis(oxy))bis(ethane-2,1-diyl))bis(oxy))bis(ethane-2,1-diyl))bis(oxy))bis(propane-1-sulfonate) | | 1.2.4 | 636.3 |
| 86 | potassium 1,1'-(1,2-phenylenebis(oxy))bis(3,6,9,12-tetraoxapentadecane-15-sulfonate) | 8 | 1.2.4 | 724.3 |
| 87 | potassium 1,1'-(1,2-phenylenebis(oxy))bis(3,6,9,12,15,18-hexaoxahenicosane-21-sulfonate) | | 1.2.4 | 900.3/ 459.2 |
| 88 | potassium 1,1'-(1,2-phenylenebis(oxy))bis(3,6,9,12,15,18,21,24-octaoxaheptacosane-27-sulfonate) | | 1.2.4 | 1076.8/ 547.4 |
| 89 | potassium 4,4'-((((((1,2-phenylenebis(oxy))bis(ethane-2,1-diyl))bis(oxy))bis(ethane-2,1-diyl))bis(oxy))bis(butane-1-sulfonate) | | 1.2.4 | 567.0 |
| 90 | potassium 1,1'-(1,2-phenylenebis(oxy))bis(3,6,9,12-tetraoxahexadecane-16-sulfonate) | | 1.2.4 | 752.3 |
| 91 | potassium 1,1'-(1,2-phenylenebis(oxy))bis(3,6,9,12,15,18-hexaoxadocosane-22-sulfonate) | | 1.2.4 | 928.3/ 473.3 |
| 92 | potassium 1,1'-(1,2-phenylenebis(oxy))bis(3,6,9,12,15,18,21,24-octaoxaoctacosane-28-sulfonate) | | 1.2.4 | 1104.4/ 561.2 |
| 93 | potassium 3,3'-(((((((4-methyl-1,2-phenylene)bis(oxy))bis(ethane-2,1-diyl))bis(oxy))bis(ethane-2,1-diyl))bis(oxy))bis(propane-1-sulfonate) | | 1.2.4 | 562.3 |
| 94 | potassium 1,1'-((4-methyl-1,2-phenylene)bis(oxy))bis(3,6,9,12-tetraoxapentadecane-15-sulfonate) | 9 | 1.2.4 | 738.1/ 378.3 |
| 95 | potassium 1,1'-((4-methyl-1,2-phenylene)bis(oxy))bis(3,6,9,12,15,18-hexaoxahenicosane-21-sulfonate) | | 1.2.4 | 914.3/ 466.3 |
| 96 | potassium 1,1'-((4-methyl-1,2-phenylene)bis(oxy))bis(3,6,9,12,15,18,21,24-octaoxaheptacosane-27-sulfonate) | | 1.2.4 | 1090.8/ 554.4 |
| 97 | potassium 4,4'-(((((((4-methyl-1,2-phenylene)bis(oxy))bis(ethane-2,1-diyl))bis(oxy))bis(ethane-2,1-diyl))bis(oxy))bis(butane-1-sulfonate) | | 1.2.4 | 590.0 |
| 98 | potassium 1,1'-((4-methyl-1,2-phenylene)bis(oxy))bis(3,6,9,12-tetraoxahexadecane-16-sulfonate) | 10 | 1.2.4 | 766.4 |
| 99 | potassium 1,1'-((4-methyl-1,2-phenylene)bis(oxy))bis(3,6,9,12,15,18-hexaoxadocosane-22-sulfonate) | | 1.2.4 | 942.0/ 480.3 |
| 100 | potassium 1,1'-((4-methyl-1,2-phenylene)bis(oxy))bis(3,6,9,12,15,18,21,24-octaoxaoctacosane-28-sulfonate) | | 1.2.4 | 1118/ 568 |
| 101 | potassium 1,1'-(((((((4-methyl-1,2-phenylene)bis(oxy))bis(ethane-2,1-diyl))bis(oxy))bis(ethane-2,1-diyl))bis(oxy))bis(pentane-3-sulfonate) | 17 | 1.2.4 | 618.3 |
| 102 | potassium 4,4'-(((((((4-methyl-1,2-phenylene)bis(oxy))bis(ethane-2,1-diyl))bis(oxy))bis(ethane-2,1-diyl))bis(oxy))bis(1-phenylbutane-2-sulfonate) | 16 | 1.2.4 | 742.3 |
| 103 | potassium 1,1'-((4-methyl-1,2-phenylene)bis(oxy))bis(28-phenyl-3,6,9,12,15,18,21,24-octaoxaoctacosane-27-sulfonate) | | 1.2.4 | 644.5 |
| 104 | potassium 3,3'-(((((((4-ethyl-1,3-phenylene)bis(oxy))bis(ethane-2,1-diyl))bis(oxy))bis(ethane-2,1-diyl))bis(oxy))bis(propane-1-sulfonate) | | 1.2.4 | 576.3 |
| 105 | potassium 1,1'-((4-ethyl-1,3-phenylene)bis(oxy))bis(3,6,9,12-tetraoxapentadecane-15-sulfonate) | | 1.2.4 | 752.3 |
| 106 | potassium 1,1'-((4-ethyl-1,3-phenylene)bis(oxy))bis(3,6,9,12,15,18-hexaoxahenicosane-21-sulfonate) | | 1.2.4 | 928.3/ 473.3 |

| | Chemical name | Ex. No. | Scheme no. | m/z. as NH$_4$ adduct |
|---|---|---|---|---|
| 107 | potassium 1,1'-((4-ethyl-1,3-phenylene)bis(oxy))bis(3,6,9,12,15,18,21,24-octaoxaheptacosane-27-sulfonate) | | 1.2.4 | 1104.4/ 561.2 |
| 108 | potassium 4,4'-((((((4-ethyl-1,3-phenylene)bis(oxy))bis(ethane-2,1-diyl))bis(oxy))bis(ethane-2,1-diyl))bis(oxy))bis(butane-1-sulfonate) | | 1.2.4 | 604.3 |
| 109 | potassium 1,1'-((4-ethyl-1,3-phenylene)bis(oxy))bis(3,6,9,12-tetraoxahexadecane-16-sulfonate) | | 1.2.4 | 780.3 |
| 110 | potassium 1,1'-((4-ethyl-1,3-phenylene)bis(oxy))bis(3,6,9,12,15,18-hexaoxadocosane-22-sulfonate) | | 1.2.4 | 956.4/ 487.3 |
| 111 | potassium 1,1'-((4-ethyl-1,3-phenylene)bis(oxy))bis(3,6,9,12,15,18,21,24-octaoxaoctacosane-28-sulfonate) | | 1.2.4 | 1132.2/ 575.1 |
| 112 | potassium 3,3'-((((((4-(tert-butyl)-1,2-phenylene)bis(oxy))bis(ethane-2,1-diyl))bis(oxy))bis(ethane-2,1-diyl))bis(oxy))bis(propane-1-sulfonate) | | 1.2.4 | 604.3 |
| 113 | potassium 1,1'-((4-(tert-butyl)-1,2-phenylene)bis(oxy))bis(3,6,9,12-tetraoxapentadecane-15-sulfonate) | | 1.2.4 | 780.4/ 399.4 |
| 114 | potassium 1,1'-((4-(tert-butyl)-1,2-phenylene)bis(oxy))bis(3,6,9,12,15,18-hexaoxahenicosane-21-sulfonate) | | 1.2.4 | 956.5/ 487.4 |
| 115 | potassium 1,1'-((4-(tert-butyl)-1,2-phenylene)bis(oxy))bis(3,6,9,12,15,18,21,24-octaoxaheptacosane-27-sulfonate) | | 1.2.4 | 1132.8/ 575.4 |
| 116 | potassium 4,4'-((((((4-(tert-butyl)-1,2-phenylene)bis(oxy))bis(ethane-2,1-diyl))bis(oxy))bis(ethane-2,1-diyl))bis(oxy))bis(butane-1-sulfonate) | | 1.2.4 | 632.3 |
| 117 | potassium 1,1'-((4-(tert-butyl)-1,2-phenylene)bis(oxy))bis(3,6,9,12-tetraoxahexadecane-16-sulfonate) | | 1.2.4 | 808.5/ 413.4 |
| 118 | potassium 1,1'-((4-(tert-butyl)-1,2-phenylene)bis(oxy))bis(3,6,9,12,15,18-hexaoxadocosane-22-sulfonate) | | 1.2.4 | 984.5/ 501.4 |
| 119 | potassium 1,1'-((4-(tert-butyl)-1,2-phenylene)bis(oxy))bis(3,6,9,12,15,18,21,24-octaoxaoctacosane-28-sulfonate) | | 1.2.4 | 1160/ 589.4 |
| 120 | potassium 1,1'-((3,5-di-tert-butyl-1,2-phenylene)bis(oxy))bis(3,6,9,12-tetraoxapentadecane-15-sulfonate) | | 1.2.4 | 836.4/ 427.4 |
| 121 | potassium 1,1'-((3,5-di-tert-butyl-1,2-phenylene)bis(oxy))bis(3,6,9,12,15,18-hexaoxahenicosane-21-sulfonate) | | 1.2.4 | 1012.5/ 515.4 |
| 122 | potassium 1,1'-((3,5-di-tert-butyl-1,2-phenylene)bis(oxy))bis(3,6,9,12-tetraoxahexadecane-16-sulfonate) | | 1.2.4 | 864.5/ 441.4 |
| 123 | potassium 3,3'-(((((4-chloro-1,3-phenylene)bis(oxy))bis(ethane-2,1-diyl))bis(oxy))bis(ethane-2,1-diyl))bis(oxy))bis(propane-1-sulfonate) | | 1.2.4 | 582.2 |
| 124 | potassium 1,1'-((4-chloro-1,3-phenylene)bis(oxy))bis(3,6,9,12-tetraoxapentadecane-15-sulfonate) | | 1.2.4 | 758.2 |
| 125 | potassium 4,4'-((((((4-chloro-1,3-phenylene)bis(oxy))bis(ethane-2,1-diyl))bis(oxy))bis(ethane-2,1-diyl))bis(oxy))bis(butane-1-sulfonate) | | 1.2.4 | 610.2 |
| 126 | potassium 1,1'-((4-chloro-1,3-phenylene)bis(oxy))bis(3,6,9,12-tetraoxahexadecane-16-sulfonate) | | 1.2.4 | 786.3 |
| 127 | potassium 3,3'-(((((naphthalene-2,3-diylbis(oxy))bis(ethane-2,1-diyl))bis(oxy))bis(ethane-2,1-diyl))bis(oxy))bis(propane-1-sulfonate) | | 1.2.4 | 598.3 |
| 128 | potassium 1,1'-(naphthalene-2,3-diylbis(oxy))bis(3,6,9,12-tetraoxapentadecane-15-sulfonate) | | 1.2.4 | 774.3/ 396.3 |
| 129 | potassium 1,1'-(naphthalene-2,3-diylbis(oxy))bis(3,6,9,12,15,18-hexaoxahenicosane-21-sulfonate) | | 1.2.4 | 950.3/ 484.3 |

-continued

| | Chemical name | Ex. No. | Scheme no. | m/z. as NH₄ adduct |
|---|---|---|---|---|
| 130 | potassium 1,1'-(naphthalene-2,3-diylbis(oxy))bis(3,6,9,12,15,18,21,24-octaoxaheptacosane-27-sulfonate) | | 1.2.4 | 1126.8/ 572.4 |
| 131 | potassium 4,4'-(((((naphthalene-2,3-diylbis(oxy))bis(ethane-2,1-diyl))bis(oxy)bis(ethane-2,1-diyl))bis(oxy))bis(butane-1-sulfonate) | | 1.2.4 | 626.3 |
| 132 | potassium 1,1'-(naphthalene-2,3-diylbis(oxy))bis(3,6,9,12-tetraoxahexadecane-16-sulfonate) | | 1.2.4 | 802 |
| 133 | potassium 1,1'-(naphthalene-2,3-diylbis(oxy))bis(3,6,9,12,15,18-hexaoxadocosane-22-sulfonate) | | 1.2.4 | 978.3/ 498.4 |
| 134 | potassium 1,1'-(naphthalene-2,3-diylbis(oxy))bis(3,6,9,12,15,18,21,24-octaoxaoctacosane-28-sulfonate) | | 1.2.4 | 1154.6/ 586.3 |
| 135 | 1,1'-(1,2-phenylenebis(oxy))bis(3,6,9,12,15,18,21,24-octaoxaoctacosane-28-sulfonic acid) | 4 | 1.2.4 | 1104.4/ 561.2 |
| 136 | 25,25'-((4-ethyl-1,3-phenylene)bis(oxy))bis(1-phenyl-2,5,8,11,14,17,20,23-octaoxapentacosane) | 14 | 1.2 | 1104.4/ 561.4 |
| 137 | potassium 1,1'-((4-methyl-1,2-phenylene)bis(oxy))bis(3,6,9,12-tetraoxaheptadecane-15-sulfonate) | | 1.2.4 | 794.4/ 406.3 |
| 138 | 1,2-bis((1-(naphthalen-2-yl)-2,5,8,11-tetraoxatridecan-13-yl)oxy)benzene | | 1.2 | 760.4 |
| 139 | 2,2'-(((((((4-(tert-butyl)-1,2-phenylene)bis(oxy))bis(ethane-2,1-diyl))bis(oxy))bis(ethane-2,1-diyl))bis(oxy))bis(methylene))dinaphthalene | | 1.2 | 640.4 |
| 140 | 13,13'-((4-(tert-butyl)-1,2-phenylene)bis(oxy))bis(1-(naphthalen-2-yl)-2,5,8,11-tetraoxatridecane) | | 1.2 | 816.4 |

The invention claimed is:

1. A compound of the following formula:

$$R^1R^2R^3-(-O-CHR^4CH_2-)_n-R^5-[(-CH_2-CHR^6O)_m-R^7R^8R^9]_p,$$

wherein:

$R^5$ is selected from the group consisting of:

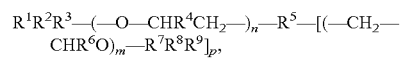

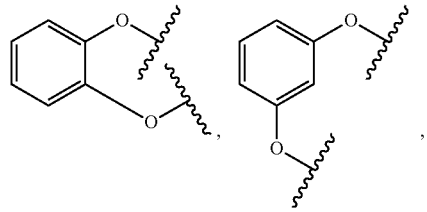

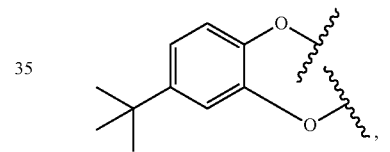

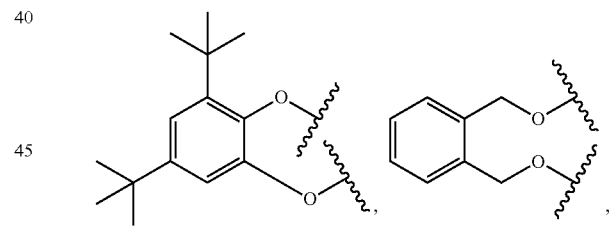

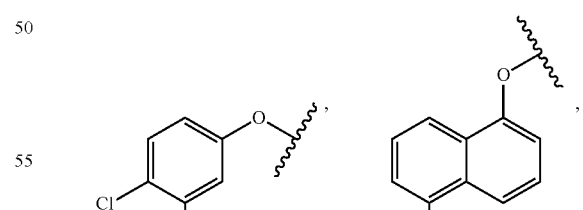

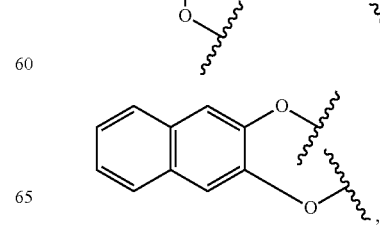

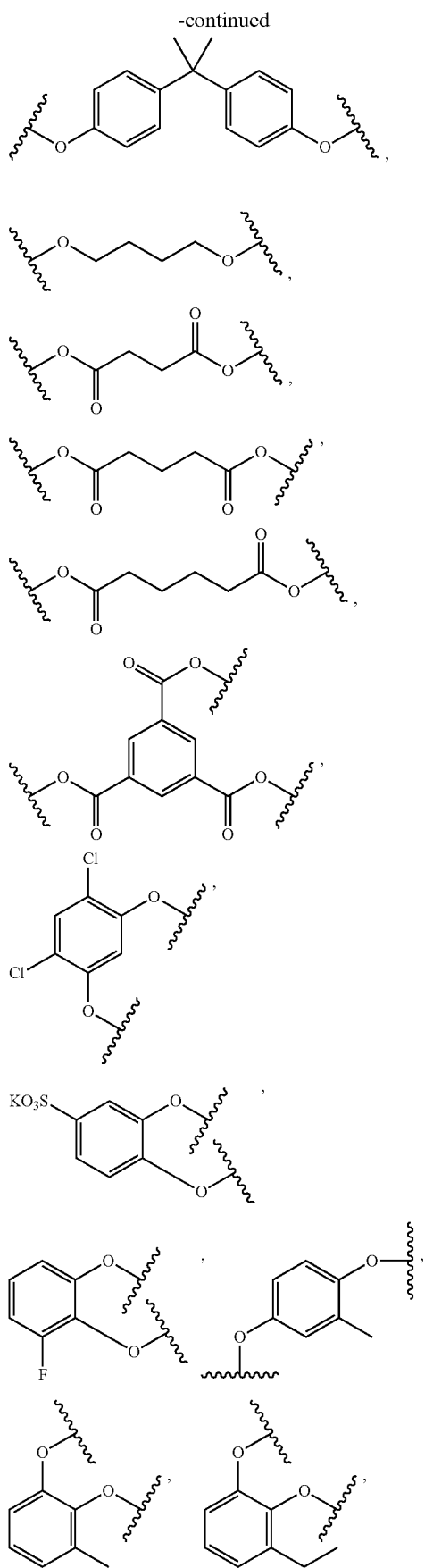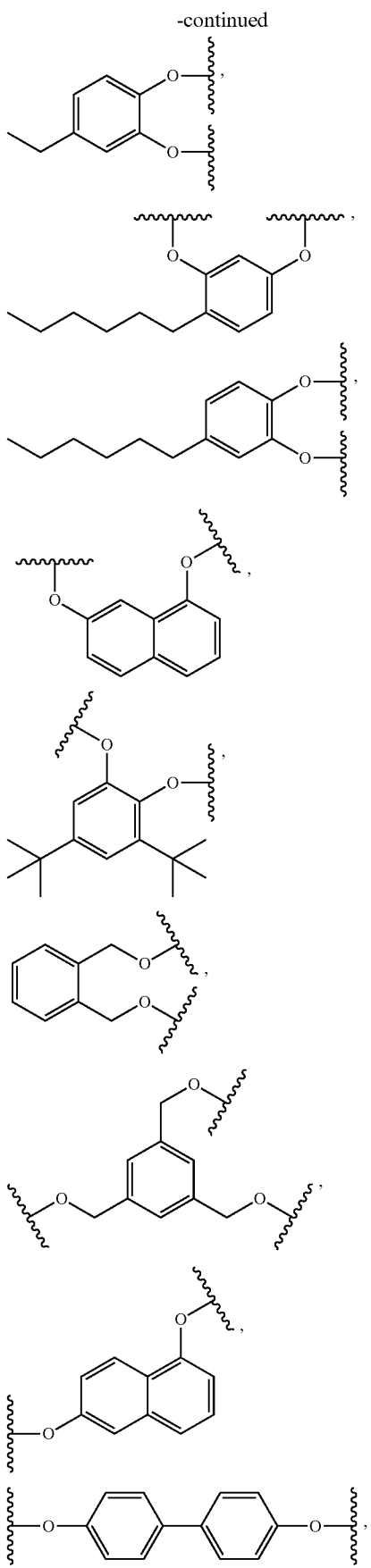

-continued

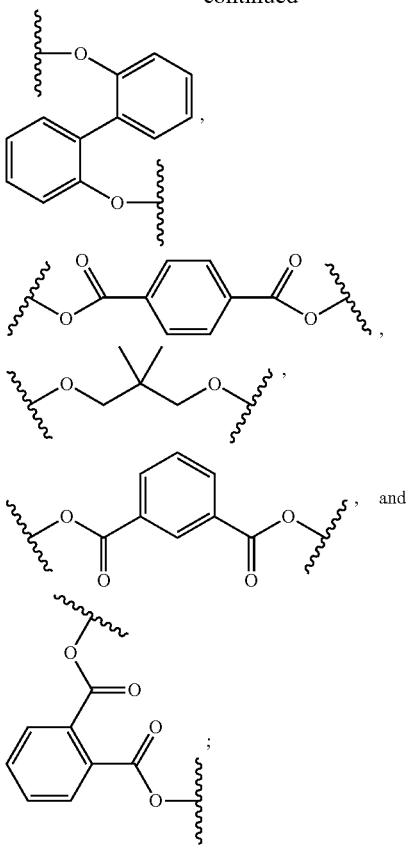

$R^4$ and $R^6$ are H or —CH$_3$ to give PEG or PPG chains;
n and m are integers between 2 and 12 in which n is the same or different from m;
p is an integer between 1 and 3 depending on $R^5$;
$R^3$ and $R^7$ are alkylic or alkenylic or aromatic hydrocarbon moieties with 2-40 carbon coupled to the PEG units or the PPG units by an ester or ether bond;
$R^2$ and $R^8$ are H;
$R^1$ and $R^9$ are sulfonic or phosphonic acid groups;
or salts, hydrates and solvates thereof; or
a compound selected from the group consisting of:
1,2-bis(2-(2-(2-(benzyloxy)ethoxy)ethoxy)ethoxy)benzene,
1,2-bis((1-phenyl-2,5,8,11-tetraoxatridecan-13-yl)oxy)benzene,
1,2-bis((1-phenyl-2,5,8,11,14-pentaoxahexadecan-16-yl)oxy)benzene,
1,2-bis((1-phenyl-2,5,8,11,14,17-hexaoxanonadecan-19-yl)oxy)benzene,
1,2-bis((1-phenyl-2,5,8,11,14,17,20,23-octaoxapentacosan-25-yl)oxy)benzene,
1,2-bis(2-(2-((4-methylbenzyl)oxy)ethoxy)ethoxy)benzene,
1,2-bis(2-(2-(2-((4-methylbenzyl)oxy)ethoxy)ethoxy)ethoxy)benzene,
1,2-bis((1-(p-tolyl)-2,5,8,11-tetraoxatridecan-13-yl)oxy)benzene,
1,2-bis((1-(p-tolyl)-2,5,8,11,14-pentaoxahexadecan-16-yl)oxy)benzene,
1,2-bis((1-(p-tolyl)-2,5,8,11,14,17-hexaoxanonadecan-19-yl)oxy)benzene,
1,2-bis((1-(4-(tert-butyl)phenyl)-2,5,8,11-tetraoxatridecan-13-yl)oxy)benzene,
1,2-bis((1-(4-(tert-butyl)phenyl)-2,5,8,11,14,17,20,23-octaoxapentacosan-25-yl)oxy)benzene,
1,2-bis(2-(2-(naphthalen-2-ylmethoxy)ethoxy)ethoxy)benzene,
1,2-bis((1-naphthalen-2-yl)-2,5,8,11,14,17-hexaoxanonadecan-19-yl)oxy)benzene,
1,3-bis((1-phenyl-2,5,8,11-tetraoxatridecan-13-yl)oxy)benzene,
(((((((4-methyl-1,2-phenylene)bis(oxy))bis(ethane-2,1-diyl))bis(oxy))bis(ethane-2,1-diyl))bis(oxy))bis(methylene))dibenzene,
(((((((((4-methyl-1,2-phenylene)bis(oxy))bis ethane-2,1-diyl))bis ox))bis ethane-2,1-diyl))bis(oxy))bis(ethane-2,1-diyl))bis(oxy))bis(methylene))dibenzene,
13,13'-((4-methyl-1,2-phenylene)bis(oxy))bis(1-phenyl-2,5,8,11-tetraoxatridecane),
16,16'-(4-methyl-1,2-phenylene)bis(oxy))bis(1-phenyl-2,5,8,11,14-pentaoxahexadecane),
19,19'-(4-methyl-1,2-phenylene)bis(oxy))bis(1-phenyl-2,5,8,11,14,17-hexaoxanonadecane),
25,25'-((4-methyl-1,2-phenylene)bis(oxy))bis(1-phenyl-2,5,8,11,14,17,20,23-octaoxapentacosane),
4,4'-((((((4-methyl-1,2-phenylene)bis(oxy))bis ethane-2,1-diyl))bis(oxy))bis ethane-2,1-diyl))bis(oxy))bis(methylene))bis(methylbenzene),
4,4'-(((((((((4-methyl-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))bis(methylbenzene),
13,13'-((4-methyl-1,2-phenylene)bis(oxy))bis(1-(p-tolyl)-2,5,8,11-tetraoxatridecane),
16,16'-(4-methyl-1,2-phenylene)bis(oxy))bis(1-(p-tolyl)-2,5,8,11,14-pentaoxahexadecane),
19,19'-((4-methyl-1,2-phenylene)bis(oxy))bis(1-(p-tolyl)-2,5,8,11,14,17-hexaoxanonadecane),
4,4'-((((((4-ethyl-1,3-phenylene)bis(oxy))bis(ethane-2,1-diyl))bis(oxy))bis(ethane-2,1-diyl))bis(oxy))bis(methylene))bis(methylbenzene),
13,13'-((4-ethyl-1,3-phenylene)bis(oxy))bis(1-(p-tolyl)-2,5,8,11-tetraoxatridecane),
19,19'-((4-ethyl-1,3-phenylene)bis(ox))bis(1-(p-tolyl)-2,5,8,11,14,17-hexaoxanonadecane),
(((((((4-(tert-butyl)-1,2-phenylene)bis(oxy))bis(ethane-2,1-diyl))bis(oxy))bis(ethane-2,1-diyl))bis(oxy))bis(methylene))dibenzene,
(((((((((4-(tert-butyl)-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))dibenzene,
13,13'-((4-(tert-butyl)-1,2-phenylene)bis(ox))bis(1-phenyl-2,5,8,11-tetraoxatridecane),
16,16'-((4-(tert-butyl)-1,2-phenylene)bis(oxy))bis(1-phenyl-2,5,8,11,14-pentaoxahexadecane),
19,19'-((4-(tert-butyl)-1,2-phenylene)bis(oxy))bis(1-phenyl-2,5,8,11,14,17-hexaoxanonadecane),
25,25'-((4-(tert-butyl)-1,2-phenylene)bis(ox))bis(1-phenyl-2,5,8,11,14,17,20,23-octaoxapentacosane),
4,4'-(((((4-(tert-butyl)-1,2-phenylene)bis(oxy))bis(ethane-2,1-diyl))bis(oxy))bis(ethane-2,1-diyl))bis(oxy))bis(methylene))bis(methylbenzene),
4,4'-((((((((4-(tert-butyl)-1,2-phenylene)bis(oxy))bis(ethane-2,1-diyl))bis(oxy))bis(ethane-2,1-diyl))bis(oxy))bis(ethane-2,1-diyl))bis(oxy))bis(methylene))bis(methylbenzene),
13,13'-((4-(tert-butyl)-1,2-phenylene)bis(oxy))bis(1-(p-tolyl)-2,5,8,11-tetraoxatridecane),
16,16'-((4-(tert-butyl)-1,2-phenylene)bis(oxy))bis(1-(p-tolyl)-2,5,8,11,14-pentaoxahexadecane),
19,19'-((4-(tert-butyl)-1,2-phenylene)bis(ox))bis(1-(p-tolyl)-2,5,8,11,14,17-hexaoxanonadecane), 25,25'-((4-(tert-butyl)-1,2-phenylene)bis(oxy))bis(1-(4-(tert-butyl)phenyl)-2,5,8,11,14,17,20,23-octaoxapentacosane),
19,19'-((4-(tert-butyl)-1,2-phenylene)bis(ox))bis(1-(naphthalen-2-yl)-2,5,8,11,14,17-hexaoxanonadecane),
(((((((3,5-di-tert-butyl-1,2-phenylene)bis(oxy))bis(ethane-2,1-diyl))bis(oxy))bis(ethane-2,1-diyl))bis(oxy))bis(methylene))dibenzene,
13,13'-((3,5-di-tert-butyl-1,2-phenylene)bis ox))bis(1-phenyl-2,5,8,11-tetraoxatridecane),
19,19'-((3,5-di-tert-butyl-1,2-phenylene)bis ox))bis(1-phenyl-2,5,8,11,14,17-hexaoxanonadecane),
25,25'-((3,5-di-tert-butyl-1,2-phenylene)bis(ox))bis(1-phenyl-2,5,8,11,14,17,20,23-octaoxapentacosane),
13,13'-((3,5-di-tert-butyl-1,2-phenylene)bis(oxy))bis(1-(4-(tert-butyl)phenyl)-2,5,8,11-tetraoxatridecane),
25,25'-((3,5-di-tert-butyl-1,2-phenylene)bis(oxy))bis(14-(tert-butyl)phenyl)-2,5,8,11,14,17,20,23-octaoxapentacosane),
1,2-bis(15-phenyl-2,5,8,11,14-pentaoxapentadecyl)benzene,
1,2-bis 27-phenyl-2,5,8,11,14,17,20,23,26-nonaoxaheptacosyl)benzene,
1,2-bis 15-(4-(tert-butyl)phenyl)-2,5,8,11,14-pentaoxapentadecyl)benzene,
4,4'-(((((((4-chloro-1,3-phenylene)bis(oxy))bis(ethane-2,1-diyl))bis(oxy))bis(ethane-2,1-diyl))bis(oxy))bis(methylene))bis(methylbenzene),
13,13'-(4-cloro-1,3-phenylene)bis ox))bis(1-(p-tolyl)-2,5,8,11-tetraoxatridecane),
1,5-bis((1-phenyl-2,5,8,11-tetraoxatridecan-13-yl)oxy)naphthalene,
2,3-bis(2-(2-(benzyloxy)ethoxy)ethoxy)naphthalene,
2,3-bis(2-(2-(2-(benzyloxy)ethoxy)ethoxy)ethoxy)naphthalene,
2,3-bis((1-phenyl-2,5,8,11-tetraoxatridecan-13-yl)oxy)naphthalene,
2,3-bis((1-phenyl-2,5,8,11,14-pentaoxahexadecan-16-yl)oxy)naphthalene,
2,3-bis((1-phenyl-2,5,8,11,14,17-hexaoxanonadecan-19-yl)oxy)naphthalene,
2,3-bis((1-phenyl-2,5,8,11,14,17,20,23-octaoxapentacosan-25-yl)oxy)naphthalene,
2,3-bis(2-(2-((4-methylbenzyl)oxy)ethoxy)ethoxy)naphthalene,
2,3-bis(2-(2-(2-((4-methylbenzyl)oxy)ethoxy)ethoxy)ethoxy)naphthalene,
2,3-bis((1-(p-tolyl)-2,5,8,11-tetraoxatridecan-13-yl)oxy)naphthalene,
2,3-bis((1-(p-tolyl)-2,5,8,11,14-pentaoxahexadecan-16-yl)oxy)naphthalene,
2,3-bis(1-(p-tolyl)-2,5,8,11,14,17-hexaoxanonadecan-19-yl)oxy)naphthalene,
13,13'-(propane-2,2-diylbis 4,1-phenylene))bis ox))bis(1-(p-tolyl)-2,5,8,11-tetraoxatridecane),
19,19'-((propane-2,2-diylbis(4,1-phenylene))bis(oxy))bis(1-(p-tolyl)-2,5,8,11,14,17-hexaoxanonadecane),
1,33-bis 4-tert-butyl)phenyl)-15,19-dimethyl-2,5,8,11,14,17,20,23,26,29,32-undecaoxatritriacontane,
1,56-diphenyl-2,5,8,11,14,17,20,23,26,31,34,37,40,43,46,49,52,55-octadecaoxahexapentacontane,
bis(1-phenyl-2,5,8,11-tetraoxatridecan-13-yl) succinate,
bis(1-(4-(tert-butyl)phenyl)-2,5,8,11-tetraoxatridecan-13-yl) succinate,
bis(1-(4-(tert-butyl)phenyl)-2,5,8,11,14,17,20,23-octaoxapentacosan-25-yl) succinate,
bis(1-phenyl-2,5,8,11-tetraoxatridecan-13-yl) glutarate,
bis(1-phenyl-2,5,8,11,14,17,20,23-octaoxapentacosan-25-yl) glutarate,
bis(1-(4-(tert-butyl)phenyl)-2,5,8,11-tetraoxatridecan-13-yl) glutarate,
bis(1-phenyl-2,5,8,11-tetraoxatridecan-13-yl) adipate,
1,3,5-tris((1-(4-tert-butyl)phenyl)-2,5,8,11-tetraoxatridecan-13-yl)oxy)benzene,
1,3,5-tris(1,5-phenyl-2,5,8,11,14-pentaoxapentadecyl)benzene,
1,3,5-tris(27-phenyl-2,5,8,11,14,17,20,23,26-nonaoxaheptacosyl)benzene,
tris(1-phenyl-2,5,8,11-tetraoxatridecan-13-yl) benzene-1,3,5-tricarboxylate,
25,25'-((4-ethyl-1,3-phenylene)bis(ox))bis(1-phenyl-2,5,8,11,14,17,20,23-octaoxapentacosane),
1,2-bis((1-(naphthalen-2-yl)-2,5,8,11-tetraoxatridecan-13-yl)oxy)benzene,
2,2'-(((((((4-(tert-butyl)-1,2-phenylene)bis(oxy))bis(ethane-2,1-diyl))bis(oxy))bis(ethane-2,1-diyl))bis(oxy))bis(methylene))dinaphthalene, and
13,13'-((4-(tert-butyl)-1,2-phenylene)bis(ox))bis(1-(naphthalen-2-yl)-2,5,8,11-tetraoxatridecane).

2. The compound according to claim 1, wherein n and m are integers between 3 and 12.

3. The compound according to claim 1, which is selected from the group consisting of:
potassium 3,3'-(((((1,2-phenylenebis(oxy))bis(ethane-21-diyl))bis(oxy))bis(ethane-2,1-diyl))bis(oxy))bis(propane-1-sulfonate),
potassium 3,3'-(((((((1,2-phenylenebis(oxy))bis(ethane-21-diyl))bis(oxy))bis(ethane-2,1-diyl))bis(oxy))bis(ethane-2,1-diyl))bis(oxy))bis(propane-1-sulfonate),
potassium 1,1'-(1,2-phenylenebis(oxy))bis(3,6,9,12-tetraoxapentadecane-15-sulfonate),
potassium 1,1'-(1,2-phenylenebis(oxy))bis(3,6,9,12,15,18-hexaoxahenicosane-21-sulfonate),
potassium 1,1'-(1,2-phenylenebis(oxy))bis(3,6,9,12,15,18,21,24-octaoxaheptacosane-27-sulfonate),
potassium 4,4'-(((((1,2-phenylenebis(ox))bis(ethane-2,1-diyl))bis(ox))bis(ethane-2,1-diyl))bis(oxy))bis(butane-1-sulfonate),
potassium 1,1'-(1,2-phenylenebis(oxy))bis(3,6,9,12-tetraoxahexadecane-16-sulfonate),
potassium 1,1'-(1,2-phenylenebis(ox))bis(3,6,9,12,15,18-hexaoxadocosane-22-sulfonate),
potassium 1,1'-(1,2-phenylenebis(oxy))bis(3,6,9,12,15,18,21,24-octaoxaoctacosane-28-sulfonate),
potassium 3,3'-((((((4-methyl-1,2-phenylene)bis(oxy))bis(ethane-2,1-diyl))bis(oxy))bis(ethane-2,1-diyl))bis(oxy))bis(propane-1-sulfonate),
potassium 1,1'-((4-methyl-1,2-phenylene)bis(ox))bis(3,6,9,12-tetraoxapentadecane-15-sulfonate),
potassium 1,1'-((4-methyl-1,2-phenylene)bis(oxy))bis(3,6,9,12,15,18-hexaoxahenicosane-21-sulfonate,
potassium 1,1'-((4-methyl-1,2-phenylene)bis ox))bis 3,6,9,12,15,18,21,24-octaoxaheptacosane-27-sulfonate),
potassium 4,4'-((((((4-methyl-1,2-phenylene)bis(oxy))bis(ethane-2,1-diyl))bis(oxy))bis(ethane-2,1-diyl))bis(oxy))bis(butane-1-sulfonate),
potassium 1,1'-((4-methyl-1,2-phenylene)bis(oxy))bis 3,6,9,12-tetraoxahexadecane-16-sulfonate),
potassium 1,1'-((4-methyl-1,2-phenylene)bis(oxy))bis(3,6,9,12,15,18-hexaoxadocosane-22-sulfonate,
potassium 1,1'-((4-methyl-1,2-phenylene)bis(oxy))bis 3,6,9,12,15,18,21,24-octaoxaoctacosane-28-sulfonate), potassium 1,1-((((((4-methyl-1,2-phenylene)bis(oxy))bis(ethane-2,1-diyl))bis(oxy))bis(ethane-2,1-diyl))bis(oxy))bis(pentane-3-sulfonate),
potassium 4,4'-((((((4-methyl-1,2-phenylene)bis(oxy))bis ethane-2,1-diyl))bis(oxy))bis ethane-2,1-diyl))bis(oxy))bis(1-phenylbutane-2-sulfonate),
potassium 1,1'-((4-methyl-1,2-phenylene)bis(oxy))bis(28-phenyl-3,6,9,12,15,18,21,24-octaoxaoctacosane-27-sulfonate),
potassium 3,3'-((((((4-ethyl-1,3-phenylene)bis(oxy))bis ethane-2,1-diyl))bis(oxy))bis ethane-2,1-diyl))bis(oxy))bis(propane-1-sulfonate),
potassium 1,1'-((4-ethyl-1,3-phenylene)bis(oxy))bis(3,6,9,12-tetraoxapentadecane-15-sulfonate),
potassium 1,1'-((4-ethyl-1,3-phenylene)bis(oxy))bis(3,6,9,12,15,18-hexaoxahenicosane-2,1-sulfonate),
potassium 1,1'-((4-ethyl-1,3-phenylene)bis(oxy))bis(3,6,9,12,15,18,21,24-octaoxaheptacosane-27-sulfonate),
potassium 4,4'-((((((4-ethyl-1,3-phenylene)bis(oxy))bis ethane-2,1-diyl))bis(oxy))bis ethane-2,1-diyl))bis(oxy))bis(butane-1-sulfonate),
potassium 1,1'-((4-ethyl-1,3-phenylene)bis(oxy))bis(3,6,9,12-tetraoxahexadecane-16-sulfonate),
potassium 1,1'-((4-ethyl-1,3-phenylene)bis(oxy))bis 3,6,9,12,15,18-hexaoxadocosane-22-sulfonate),
potassium 1,1'-((4-ethyl-1,3-phenylene)bis(oxy))bis(3,6,9,12,15,18,21,24-octaoxaoctacosane-28-sulfonate),
potassium 3,3'-((((((4-tert-butyl)-1,2-phenylene)bis(oxy))bis ethane-2,1-diyl))bis(oxy))bis(ethane-2,1-diyl))bis(oxy))bis propane-1-sulfonate),
potassium 1,1'-((4-(tert-butyl)-1,2-phenylene)bis(oxy))bis(3,6,9,12-tetraoxapentadecane-15-sulfonate),
potassium 1,1'-((4-(tert-butyl)-1,2-phenylene)bis(oxy))bis 3,6,9,12,15,18-hexaoxahenicosane-21-sulfonate),
potassium 1,1'-((4-(tert-butyl)-1,2-phenylene)bis(oxy))bis(3,6,9,12,15,18,21,24-octaoxaheptacosane-27-sulfonate),
potassium 4,4'-((((((4-tert-butyl)-1,2-phenylene)bis(oxy))bis ethane-2,1-diyl))bis(oxy))bis(ethane-2,1-diyl))bis(oxy))bis(butane-1-sulfonate),
potassium 1,1'-((4-(tert-butyl)-1,2-phenylene)bis(oxy))bis(3,6,9,12-tetraoxahexadecane-16-sulfonate),
potassium 1,1'-((4-(tert-butyl)-1,2-phenylene)bis(oxy))bis 3,6,9,12,15,18-hexaoxadocosane-22-sulfonate,
potassium 1,1'-((4-(tert-butyl)-1,2-phenylene)bis(oxy))bis(3,6,9,12,15,18,21,24-octaoxaoctacosane-28-sulfonate),
potassium 1,1'-((3,5-di-tert-butyl-1,2-phenylene)bis(oxy))bis 3,6,9,12-tetraoxapentadecane-15-sulfonate,
potassium 1,1'-((3,5-di-tert-butyl-1,2-phenylene)bis(oxy))bis(3,6,9,12,15,18-hexaoxahenicosane-21-sulfonate),
potassium 1,1'-((3,5-di-tert-butyl-1,2-phenylene)bis(oxy))bis(3,6,9,12-tetraoxahexadecane-16-sulfonate),
potassium 3,3'-((((((4-chloro-1,3-phenylene)bis(oxy))bis(ethane-2,1-diyl))bis(oxy))bis(ethane-2,1-diyl))bis(oxy))bis(propane-1-sulfonate),
potassium 1,1'-((4-chloro-1,3-phenylene)bis(oxy))bis(3,6,9,12-tetraoxapentadecane-15-sulfonate),
potassium 4,4'-((((((4-chloro-1,3-phenylene)bis(oxy))bis(ethane-2,1-diyl))bis(oxy))bis(ethane-2,1-diyl))bis(oxy))bis(butane-1-sulfonate),
potassium 1,1'-((4-chloro-1,3-phenylene)bis(oxy))bis(3,6,9,12-tetraoxahexadecane-16-sulfonate),
potassium 3,3'-(((((naphthalene-2,3-diylbis(oxy))bis(ethane-2,1-diyl))bis(oxy))bis(ethane-2,1-diyl))bis(oxy))bis(propane-1-sulfonate),
potassium 1,1'-(naphthalene-2,3-diylbis(oxy))bis(3,6,9,12-tetraoxapentadecane-15-sulfonate),
potassium 1,1'-(naphthalene-2,3-diylbis(oxy))bis(3,6,9,12,15,18-hexaoxahenicosane-21-sulfonate),
potassium 1,1'-(naphthalene-2,3-diylbis(ox))bis(3,6,9,12,15,18,21,24-octaoxaheptacosane-27-sulfonate),
potassium 4,4'-(((((naphthalene-2,3-diylbis(oxy))bis(ethane-2,1-diyl))bis(oxy))bis(ethane-2,1-diyl))bis(oxy))bis(butane-1-sulfonate),
potassium 1,1'-(naphthalene-2,3-diylbis(oxy))bis(3,6,9,12-tetraoxahexadecane-16-sulfonate),
potassium 1,1'-(naphthalene-2,3-diylbis(ox))bis(3,6,9,12,15,18-hexaoxadocosane-22-sulfonate),
potassium 1,1'-(naphthalene-2,3-diylbis(oxy))bis(3,6,9,12,15,18,21,24-octaoxaoctacosane-28-sulfonate),
1,1'-(1,2-phenylenebis(ox))bis(3,6,9,12,15,18,21,24-octaoxaoctacosane-28-sulfonic acid),
25,25'-((4-ethyl-1,3-phenylene)bis(ox))bis(1-phenyl-2,5,8,11,14,17,20,23-octaoxapentacosane), and
potassium 1,1'-((4-methyl-1,2-phenylene)bis(oxy))bis(3,6,9,12-tetraoxaheptadecane-15-sulfonate).

4. A compound according to claim 1, as tracers by LC-MS.

5. A composition comprising at least one compound according to claim 1 and at least one additional constituent selected from the group consisting of a solvent, a diluent, a surfactant, an absorbent and a stabilizer.

6. The composition according to claim 5, wherein the composition is formulated into a tablet, capsule, matrix or other geometric shape.

7. A method of using a compound according to claim 1 as a tracer, comprising injecting the compound into an oil and gas well and then later detecting the compound.

8. The method according to claim 7, wherein the compound is later detected topside after release from the oil and gas well.

9. The method according to claim 7, wherein the compound is later detected topside after release from the oil and gas well by LCMS, GCMS or a combination thereof.

10. A method of marking a fluid for permanent inflow monitoring, comprising implementing at least two compounds according to claim 1 into or onto a material.

11. The method according to claim 10, wherein the material is at least one material selected from the group consisting of a polymer, a ceramic, sand, shale, completion equipment, a tool and a pipe.

12. The method according to claim 10, further comprising implementing an additive into the material in combination with the at least two compounds.

13. A method of using 1,2-bis(2-(2-(benzyloxy)ethoxy)ethoxy)benzene as a tracer, comprising injecting 1,2-bis(2-(2-(benzyloxy)ethoxy)ethoxy)benzene into an oil and gas well and then later detecting the 1,2-bis(2-(2-(benzyloxy)ethoxy)ethoxy)benzene.

14. The method according to claim 13, wherein the 1,2-bis(2-(2-(benzyloxy)ethoxy)ethoxy)benzene is later detected topside after release from the oil and gas well.

15. The method according to claim 13, wherein the 1,2-bis(2-(2-(benzyloxy)ethoxy)ethoxy)benzene is later detected topside after release from the oil and gas well by LCMS, GCMS or a combination thereof.

16. A method of marking a fluid for permanent inflow monitoring, comprising implementing 1,2-bis(2-(2-(benzyloxy)ethoxy)ethoxy)benzene and at least one compound according to claim 1 into or onto a material.

17. The method according to claim 16, wherein the material is at least one material selected from the group consisting of a polymer, a ceramic, sand, shale, completion equipment, a tool and a pipe.

18. The method according to claim 16, further comprising implementing an additive into the material in combination with the 1,2-bis(2-(2-(benzyloxy)ethoxy)ethoxy)benzene and the at least one compound according to claim 1.

* * * * *